US006201002B1

(12) United States Patent
Beere et al.

(10) Patent No.: US 6,201,002 B1
(45) Date of Patent: Mar. 13, 2001

(54) METHOD FOR REDUCING MORTALITY WITH AN ANGIOTENSIN II ANTAGONIST

(75) Inventors: Polly A. Beere, Lahaska; Paul I. Chang, Doylestown, both of PA (US); Bertram Pitt, Ann Arbor, MI (US); Eva J. Rucinska, Blue Bell, PA (US); Robert Segal, Gwynedd Valley, PA (US); Divakar Sharma, Hatfield, PA (US); Duane B. Snavely, Chalfont, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/003,159

(22) Filed: Jan. 6, 1998

Related U.S. Application Data
(60) Provisional application No. 60/034,927, filed on Jan. 10, 1997.

(51) Int. Cl.$^7$ .................................................. A01N 43/50
(52) U.S. Cl. ..................... 514/397; 514/85; 514/86; 514/87; 514/88; 514/94; 514/235.8; 514/236.2; 514/252.13; 514/254.05; 514/255.05; 514/326; 514/381; 514/382; 514/396; 514/397; 514/398; 514/399; 514/400
(58) Field of Search ............................... 514/235.8, 236.2, 514/252.13, 254.05, 255.05, 326, 381, 382, 396, 397, 398, 399, 400, 85, 86, 87, 88, 94

(56) References Cited

U.S. PATENT DOCUMENTS

| | | | |
|---|---|---|---|
| 5,128,355 | 7/1992 | Carini et al. | 514/381 |
| 5,138,069 | 8/1992 | Carini et al. | 514/381 |
| 5,153,197 | 10/1992 | Carini et al. | 514/381 |
| 5,795,904 * | 8/1998 | Cohen et al. | 514/381 |

FOREIGN PATENT DOCUMENTS

WO 96/40257  12/1996  (WO) .

OTHER PUBLICATIONS

Chemical Abstract 119:173956, "Losartan's Protective Effects in Stroke–Prone Spontaneously Hypertensive Rats Persist Durably After Treatment Withdrawl", Feb. 1993.*
Lenz, O., et al., Eur. J. Pharmacol., vol. 294(1), pp. 17–27, 1995.
Awan, N.A., et al., Am. Heart Journal, vol. 131(1), pp. 177–185, 1996.
Drugs of the Future, vol. 21(7), pp. 738–739, 1996.
Lejemtel, T., et al., Circulation, vol. 94(8) Suppl., pp. 1622–1623, 1996.
Crozier, I., et al., Circulation, vol. 91(3), pp. 691–697, 1995.
Fujimori, A., et al., JPN. J. Pharmacol., vol. 67 (1) Suppl., ABS No. P1–155, 1995.
Kusayama, T., et al., JPN. J. Pharmacol., vol. 67(1) Suppl., ABS No. P1–154, 1995
Inada, Y., et al., Folia Pharmacol. JPN., vol. 104(3), pp. 217–228, 1994 (English Abstract on p. 228).
Buhlmayer, P., et al., Bioorg. Med. Chem. Lett., vol. 4(1), pp. 29–34, 1994.
Noel, B., et al., J. Cardiovasc. Pharmacol., vol. 28(2), pp. 252–258, 1996.
Drugs of the Future, vol. 20(7), pp. 740–742, 1995.
Pitt, B., et al., Cardiovasc. Drugs and Therapy, vol. 9, pp. 693–700, 1995.
Pitt, B., et al., Circulation. vol. 100(18), Abstract 4128, Supplement I, Nov. 1999.
Pitt, B., et al., American Heart Association, Scientific Session, Nov. 1999, Slide Presentation.

* cited by examiner

*Primary Examiner*—Frederick Krass
(74) *Attorney, Agent, or Firm*—Valerie J. Camara; Mark R. Daniel

(57) ABSTRACT

Angiotensin II receptor antagonists are useful in reducing and preventing mortality and sudden cardiac death in symptomatic heart failure patients. Losartan potassium has been shown to reduce mortality and sudden cardiac death in this patient population. Additionally, losartan potassium has been shown to reduce the need for hospitalization of symptomatic heart failure patients.

33 Claims, 5 Drawing Sheets

METHOD FOR REDUCING MORTALITY WITH AN ANGIOTENSIN II ANTAGONIST

This application claims the benefit of U.S. Provisional Application Ser. No. 60/034,927, filed Jan. 10, 1997.

BACKGROUND OF THE INVENTION

Angiotensin-converting-enzyme (ACE) inhibitors have been shown to reduce morbidity and mortality in patients with chronic heart failure and systolic left ventricular dysfunction as well as in patients post myocardial infarction. (See The CONSENSUS Trial Study Group. Effects of enalapril on mortality in severe congestive heart failure. Results of the Cooperative North Scandinavian Enalapril Survival Study (CONSENSUS). N Engl J Med 1997; 316: 1429–1435; The SOLVD Investigators. Effect of enalapril on survival in patients with reduced left ventricular ejection fractions and congestive heart failure. N Engl J Med 1991; 325: 293–302; The SOLVD Investigators. Effect of enalapril on mortality and the development of heart failure in asymptomatic patients with reduced left ventricular ejection fractions. N Engl J Med 1992; 327: 685–691; Cohn J N, Johnson G, Ziesche S, et al. A comparison of enalapril with hydralazine-isosorbide dinitrate in the treatment of chronic congestive heart failure. N Engl J Med 1991; 325: 303–310; Pfeffer MA, Braunwald E, Moye L A, et al. on behalf of the SAVE Investigators. Effect of captopril on mortality and morbidity in patients with left ventricular dysfunction after myocardial infarction. Results of the Survival and Ventricular Enlargement Trial. N Engl J Med 1992; 327: 669–677; The Acute Infarction Ramipril Efficacy (AIRE) Study Investigators. Effect of ramipril on mortality and morbidity of survivors of acute myocardial infarction with clinical evidence of heart failure. Lancet 1993; 342: 812–828; Fonarow GC, Chelimsky-Fallick C, Warner Stevenson L, et al. Effect of direct vasodilation with hydralazine versus angiotensin-converting enzyme inhibition with captopril on mortality in advanced heart failure: the Hy-C trial. J Am Coll Cardiol 1992; 19: 842–850; Gruppo Italiano per lo Studio delia Sopravvivenza nell'infarto Miocardico. GISSI-3: Effects of lisinopril and transdermal glyceryl trinitrate singly and together on 6-week mortality and ventricular function after acute myocardial infarction. Lancet 1994; 343: 1115–1122; ISIS Collaborative Group OU. ISIS-4: Randomized study of oral isosorbide mononitrate in over 50,000 patients with suspected acute myocardial infarction. Circulation 1993; 89: 1394.) The benefits of ACE inhibitors have been attributed to blockade of angiotensin II production and/or to a decrease in the breakdown of bradykinin. (See Pitt B, Chang P, Timmermans P. Angiotensin II receptor antagonists in heart failure: Rationale and design of the Evaluation of Losartan in the Elderly (ELITE) Trial. Cardiovascular Drugs and Therapy 1995; 9: 693–700; and Gavras I. Bradykinin-mediated effects of ACE inhibition. Kidney Int 1992; 42:1020–1029.) Bradykinin has been shown to have beneficial effects associated with the release of nitric oxide and prostacyclin which may contribute to the hemodynamic effects of ACE inhibition. Bradykinin may, however, also be responsible for certain adverse effects associated with use of ACE inhibitors, such as cough, angioedema, renal dysfunction, and hypotension. (See Pitt B, Chang P, Timmermans P. Angiotensin II receptor antagonists in heart failure: Rationale and design of the Evaluation of Losartan in the Elderly (ELITE) Trial. Cardiovascular Drugs and Therapy 1995; 9: 693–700; Gavras I. Bradykinin-mediated effects of ACE inhibition. Kidney int 1992; 42: 1020–1029; Israili Z H, Hall W D. Cough and angioneurotic edema associated with angiotensin-converting enzyme inhibitor therapy. A review of the literature and pathophysiology. Ann Intern Med 1992; 117: 234–242; Chalmers D, Dombey S L, Lawson D H. Post-marketing surveillance of captopril (for hypertension): a preliminary report. Br J Clin Pharmacol 1987; 24: 343–349; Lacourciere Y, Brunner H, Irwin R, et al. and the Losartan Cough Study Group. Effects of modulators of the renin-angiotensin-aldosterone system on cough. J Hypertension 1994; 12: 1387–1393.) These adverse effects may account in part for the fact that ACE inhibitors are used in less than 30 percent of patients with heart failure in spite of their proven clinical benefit. (See Stafford R S, Saglam D, Blumenthal D. Low rates of angiotensin-converting enzyme inhibitor use in congestive heart failure. Circulation 1996; 94: I-194(Abstract)).

The development of orally-active, nonpeptidic angiotensin II type 1 receptor antagonists such as losartan, has provided the opportunity to block the angiotensin II type 1 receptor specifically without increasing bradykinin levels. (See Timmermans P, Wong P C, Chiu A T, et al. Angiotensin II receptors and angiotensin II receptor antagonists. Pharmacol Reviews 1993; 45: 205–251.) Since angiotensin II may be produced by alternate pathways, losartan may offer additional advantages over treatment with ACE inhibitors where blockade of the effects of angiotensin II may be incomplete. (See Miura S, Ideishi M, Sakai T, et al. Angiotensin II formation by an alternative pathway during exercise in humans. J Hypertension 1994; 12: 1177–1181; Urata H, Kinoshita A, Misono K S, Bumpus F M, Husain A. Identification of a highly specific chymase as the major angiotensin II-forming enzyme in the human chymase. J Biol Chem 1990; 265: 22348–22357; Urata H, Strobel F, Ganten D. Widespread tissue distribution of human chymase. J Hypertension 1994; 12: S17–S22; Aldigier J C, Huang H, Dalmay F, et al. Angiotensin-converting enzyme inhibition does not suppress plasma angiotensin II increase during exercise in humans. J Cardiovasc Pharmacol 1993; 21: 289–295.) Losartan is indicated for the treatment of hypertension in many countries and in earlier studies in patients with symptomatic heart failure, oral losartan produced beneficial hemodynamic effects both acutely and with chronic dosing. (See Crozier I, Ikram H, Awan N, et al. Losartan in heart failure: Hemodynamic effects and tolerability. Circulation 1995; 91: 691–697; and Gottlieb S S, Dickstein K, Fleck E, et al. Hemodynamic and neurohormonal effects of the angiotensin II antagonist losartan in patients with congestive heart failure. Circulation 1993; 88: 1602–1609.)

The Evaluation of Losartan In The Elderly (ELITE) Study was conducted to compare effects on renal function, morbidity/mortality, and tolerability of long-term treatment with losartan versus captopril, in older patients with symptomatic heart failure.

SUMMARY OF THE INVENTION

A method for reducing mortality by administering to a symptomatic heart failure patient a therapeutically effective amount of an angiotensin II antagonist. A method for reducing sudden cardiac death by administering to a symptomatic heart failure patient a therapeutically effective amount of an angiotensin II antagonist. A method for reducing mortality and sudden cardiac death by administering to a symptomatic heart failure patient a therapeutically effective amount of an angiotensin II antagonist is disclosed. A method for preventing sudden cardiac death by administering to a symptomatic heart failure patient a therapeutically effective amount of an angiotensin II antagonist. A method for reducing hospitalization by administering to a symptomatic heart failure patient a therapeutically effective amount of an angiotensin 11 antagonist.

DETAILED DESCRIPTION OF THE INVENTION

Figure 1:
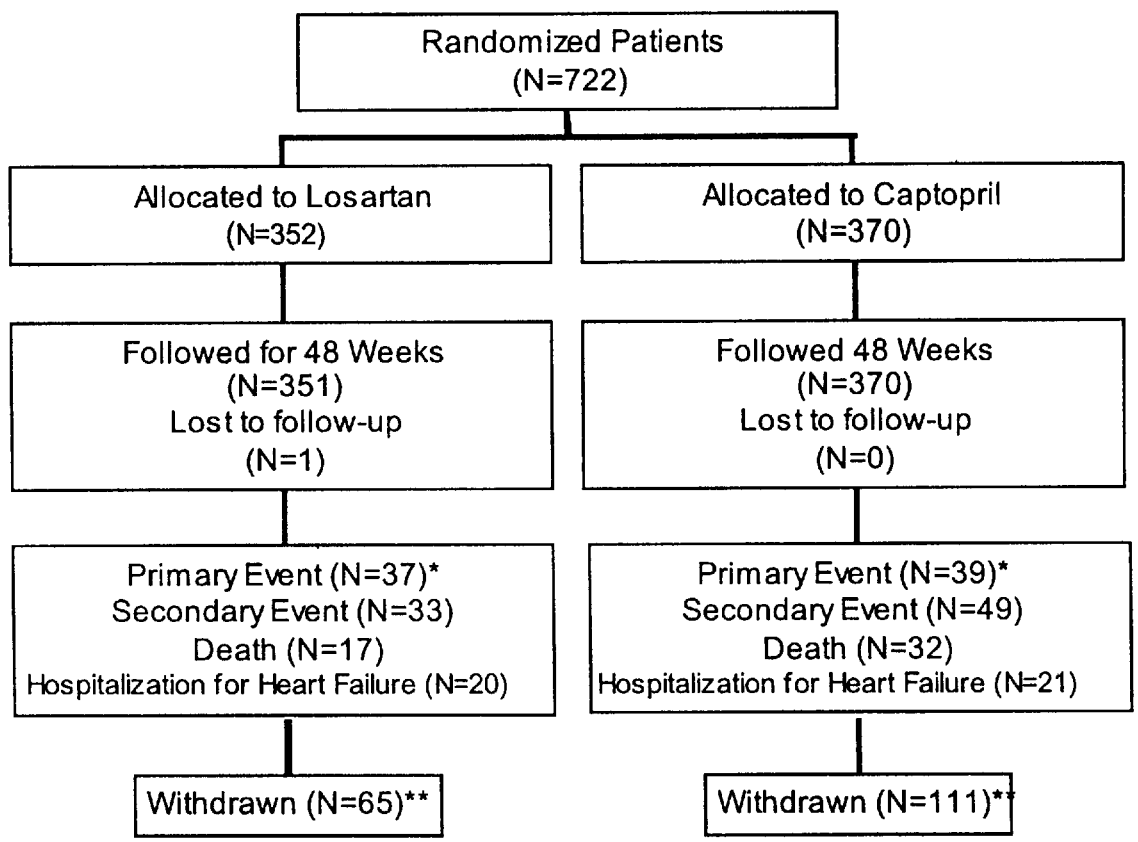
FIG. 1. ELITE Study Profile.
(* While on study therapy; and ** Withdrawn from assigned therapy, but still followed up for the intention-to-treat analysis of secondary endpoint.)

This invention concerns a method for reducing mortality by administering to a symptomatic heart failure patient a therapeutically effective amount of an angiotensin II antagonist.

An embodiment of this invention is the method for reducing mortality by administering to a symptomatic heart failure patient a therapeutically effective amount of an angiotensin II receptor antagonist selected from the group consisting of: candesartan cilexetil, eprosartan, irbesartan, losartan, tasosartan, telmisartan, valsartan, BMS-184699, 3-(2'-(tetrazol-5-yl)-1,1'-biphen-4-yl)methyl-5,7-dimethyl-2-ethyl-3H-imidazo[4,5-b]pyridine, BAY 106734, BIBR363, CL329167, E4177, EMD73495, HN65021, HR720, HOE720, LRB081, SC52459, SL910102, UP2696, YM358, EMD66397, ME3221, TAK536, BMS 184698, CGP42112A, CGP49870, CP 14R130, E4188, EMD666R4, EXP9954, FRI 153332, GA0050, KT3579, LF70156, LRB057, LY266099, LY301875, PD 123177, PD 126055, SC51757, SC54629, U96849, UK77778, WAY126227, WK1260, WK1492, YH1498, and YM31472. The preferred angiotensin II receptor antagonists useful in this method are: candesartan cilexetil, eprosartan, irbesartan, losartan, tasosartan, telmisartan, valsartan, BMS-194698 and 3-(2'-(tetrazol-5-yl)-1,1'-biphen-4-yl)methyl-5,7-dimethyl-2-ethyl-3H-imidazo[4,5-b]pyridine.

Another embodiment of the invention is the method for reducing mortality by administering to a symptomatic heart failure patient a therapeutically effective amount of an imidazole angiotensin II receptor antagonist of formula I

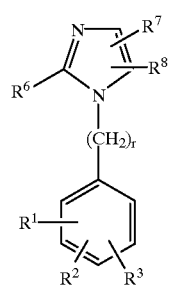

wherein:

$R^1$ is:

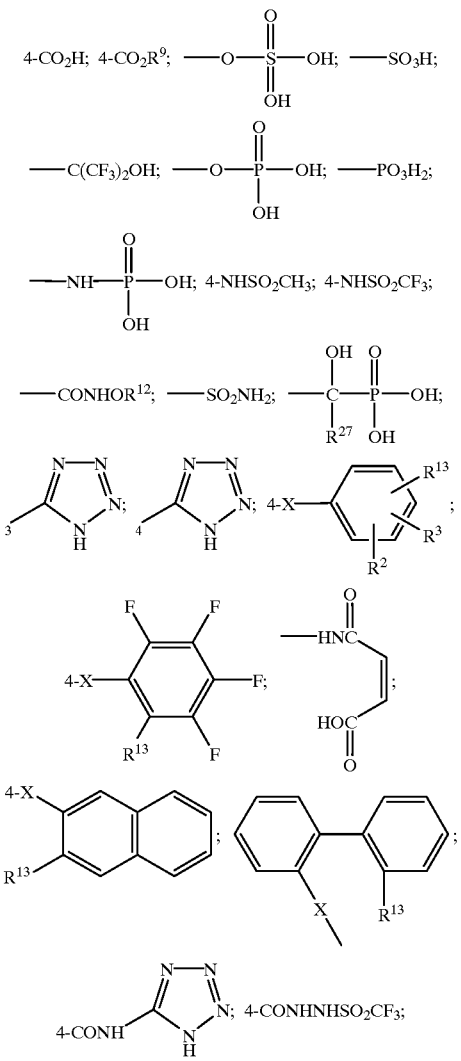

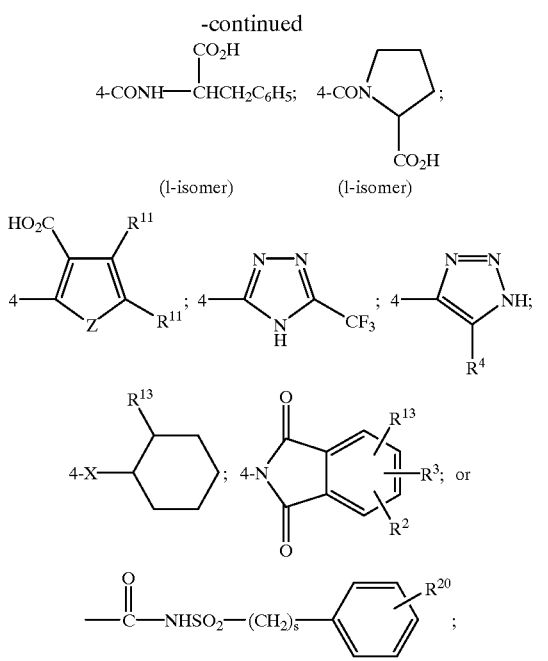

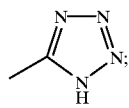

$R^2$ is H; Cl; Br; I; F; $NO_2$; CN; alkyl of 1 to 4 carbon atoms; acyloxy of 1 to 4 carbon atoms; alkoxy of 1 to 4 carbon atoms; $CO_2H$; $CO_2R^9$; $HNSO_2CH_3$; $NHSO_2CF_3$; $CONHOR^{12}$; $SO_2NH_2$;

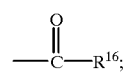

aryl; or furyl;

$R^3$ is H; Cl, Br, I or F; alkyl of 1 to 4 carbon atoms or alkoxy of 1 to 4 carbon atoms;

$R^4$ is CN, $NO_2$ or $CO_2R^{11}$;

$R^5$ is H, alkyl of 1 to 6 carbon atoms, cycloalkyl of 3 to 6 carbon atoms alkenyl or alkynyl of 2 to 4 carbon atoms;

$R^6$ is alkyl of 2 to 10 carbon atoms, alkenyl or alkynyl of 3 to 10 carbon atoms or the same groups substituted with F or $CO_2R^{14}$; cycloalkyl of 3 to 8 carbon atoms, cycloalkylalkyl, of 4 to 10 carbon atoms; cycloalkylalkenyl or cycloalkylalkynyl 5 to 10 carbon atoms; $CH_2)_sZ(CH_2)_mR^5$ optionally substituted with F or $CO_2R^{14}$; benzyl substituted on the phenyl ring with 1 or 2 halogens, alkoxy of 1 to 4 carbon atoms, alkyl of 1 to 4 carbon atoms or nitro;

$R^7$ is H, F, Cl, Br, I, $NO_2$, $C_vF_{2v+1}$, where v=1–6, $C_6F_5$; CN;

$$-\overset{O}{\underset{}{C}}-R^{16};$$

straight or branched alkyl of 1 to 6 carbon atoms; phenyl or phenylalkyl, where alkyl is 1 to 3 carbon atoms; or substituted phenyl or substituted phenylalkyl, where alkyl is 1 to 3 carbon atoms, substituted with one or two substituents selected from alkyl of 1 to 4 carbon atoms, F, Cl, Br, OH, $OCH_3$, $CF_3$, and COOR, where R is H, alkyl of 1 to 4 carbon atoms, or phenyl;

$R^8$ is H, CN, alkyl of 1 to 10 carbon atoms, alkenyl of 3 to 10 carbon atoms, or the same groups substituted with F; phenylalkenyl wherein the aliphatic portion is 2 to 6 carbon atoms; $-(CH_2)_m$-imidazol-1-yl; $-(CH_2)_m$-1,2,3-triazolyl optionally substituted with one or two group selected from $CO_2CH_3$ or alkyl of 1 to 4 carbon atoms; $-(CH_2)_s$ tetrazolyl;

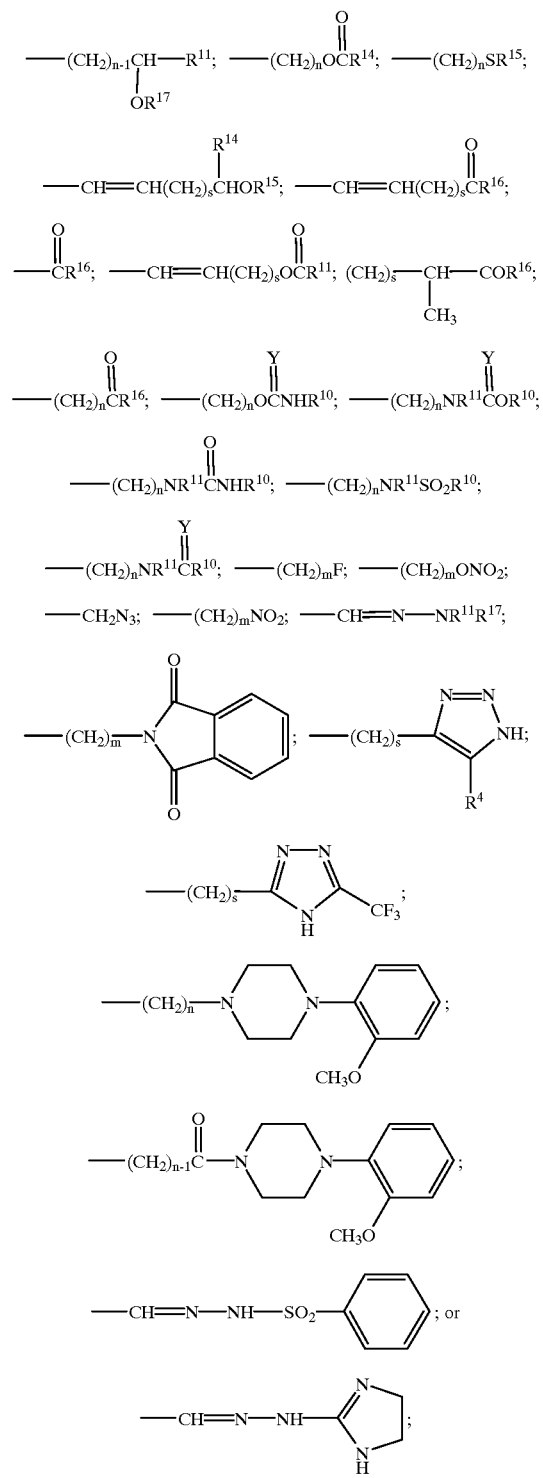

$R^9$ is

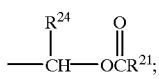

$R^{10}$ is alkyl of 1 to 6 carbon atoms or perfluoroalkyl of 1 to 6 carbon atoms, 1-adamantyl, 1-naphthyl, 1-(1-naphthyl)ethyl, or $(CH_2)_pC_6H_5$;

$R^{11}$ is H, alkyl of 1 to 6 carbon atoms, cycloalkyl of 3 to 6 carbon atoms, phenyl or benzyl;

$R^{12}$ is H, methyl or benzyl;

$R^{13}$ is

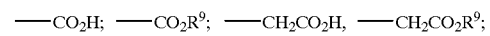
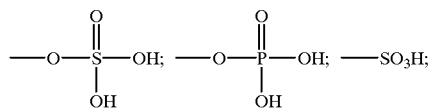
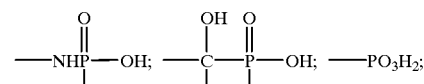
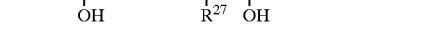
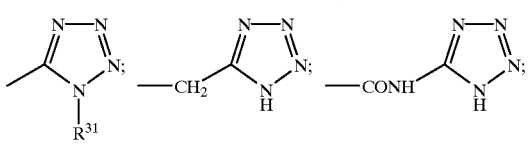
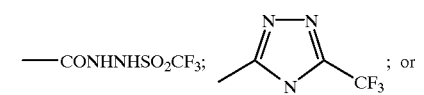
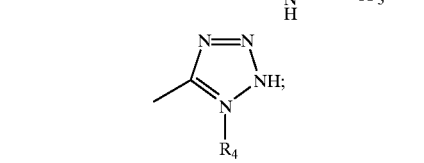

$R^{14}$ is H, alkyl or perfluoroalkyl of 1 to 9 carbon atoms, cycloalkyl of 3 to 6 carbon atoms, phenyl or benzyl;

$R^{15}$ is H, alkyl of 1 to 6 carbon atoms, cycloalkyl of 3 to 6 carbon atoms, phenyl, benzyl, acyl of 1 to 4 carbon atoms, phenacyl;

$R^{16}$ is H, alkyl of 1 to 6 carbon atoms, cycloalkyl of 3 to 6 carbon atoms, $(CH_2)_pC_6H_5$, $OR_{17}$, or $NR^{18}R^{19}$;

$R^{17}$ is H, alkyl of 1 to 6 carbon atoms, cycloalkyl of 3 to 6 carbon atoms, phenyl or benzyl;

$R^{18}$ and $R^{19}$ independently are H, alkyl of 1 to 4 carbon atoms, phenyl, benzyl, α-methylbenzyl, or taken together with the nitrogen form a ring of the formula

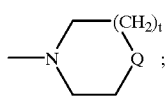

Q is $NR^{20}$, O or $CH_2$;

$R^{20}$ is H, alkyl of 1–4 carbon atoms, or phenyl;

$R^{21}$ is alkyl of 1 to 6 carbon atoms, $—NR^{22}R^{23}$, or

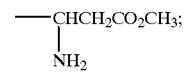

$R^{22}$ and $R^{23}$ independently are H, alkyl of 1 to 6 carbon atoms, benzyl, or are taken together as $(CH_2)_u$, where u is 3–6;

$R^{24}$ is H, $CH_3$ or $—C_6H_5$;

$R^{25}$ is $NR^{27}R^{28}$, $OR^{28}$, $NHCONH_2$, $NHCSNH_2$,

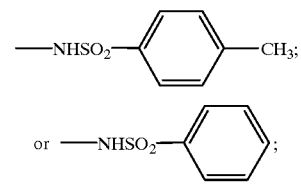

$R^{26}$ is hydrogen, alkyl with from 1 to 6 carbon atoms, benzyl, or allyl;

$R^{27}$ and $R^{28}$ are independently hydrogen, alkyl with from 1 to 5 carbon atoms, or phenyl;

$R^{29}$ and $R^{30}$ are independently alkyl of 1–4 carbon atoms or taken together are $—(CH_2)_q—$;

$R^{31}$ is H, alkyl or 1 to 4 carbon atoms, $—CH_2CH=CH_2$ or $—CH_2C_6H_4R^{32}$;

X is a carbon—carbon single bond,

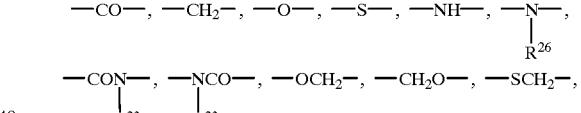
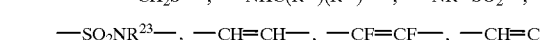
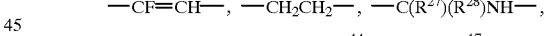
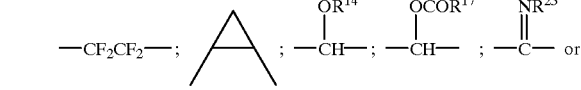

Y is 0 or S;

Z is 0, $NR^{11}$, or S;

m is 1 to 5;

n is 1 to 10;

p is 0 to 3;

q is 2 to 3;

r is 0 to 2;

s is 0 to 5;

t is 0 or 1;

and pharmaceutically acceptable salts of these compounds; provided that:

(1) the $R^1$ group is not in the ortho position;

(2) when $R^1$ is

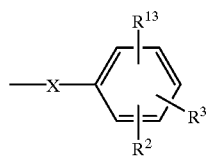

X is a single bond, and $R^{13}$ is $CO_2H$, or

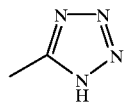

then $R^3$ must be in the ortho or meta position; or when $R^1$ and X are as above and $R^{13}$ is $NHSO_2CF_3$ or $NHSO_2CH_3$, $R^{13}$ must be ortho;

(3) when $R^1$ is

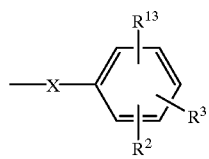

and X is other than a single bond, then $R^{13}$ must be ortho except when $X=NR^{23}CO$ and $R^{13}$ is $NHSO_2CF_3$ or $NHSO_2CH_3$, then $R^{13}$ must be ortho or meta;

(4) when $R^1$ is $4-CO_2H$ or a salt thereof, $R^6$ cannot be S-alkyl;

(5) when $R^1$ is $4-CO_2H$ or a salt thereof, the substituent on the 4-position of the imidazole cannot be $CH_2OH$, $CH_2OCOCH_3$, or $CH_2CO_2H$;

(6) when $R^1$ is

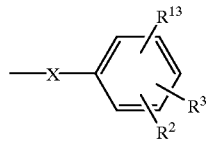

X is $-OCH_2-$, and $R^{13}$ is $2-CO_2H$, and $R^7$ is H then $R^6$ is not $C_2H_5S$;

(7) when $R^1$ is

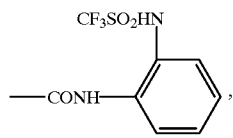

and $R^6$ is n-hexyl then $R^7$ and $R^8$ are not both hydrogen;

(8) when $R^1$ is

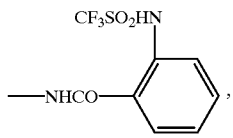

$R^6$ is not methoxybenzyl;

(9) the $R^6$ group is not

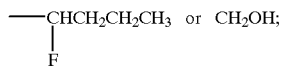

(10) when r=0, $R^1$ is

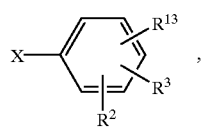

X is

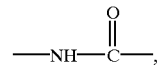

$R^{13}$ is $2-NHSO_2CF_3$, and $R^6$ is n-propyl, then $R^7$ and $R^8$ are not $-CO_2CH_3$;

(11) when r=0, $R^1$ is

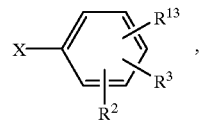

X is

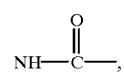

$R^{13}$ is 2-COOH, and $R^6$ is n-propyl, then $R^7$ and $R^8$ are not $-CO_2CH_3$;

(12) when r=1,

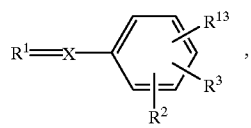

X is a single bond, $R^7$ is Cl, and $R^8$ is $-CHO$, then $R^{13}$ is not 3-(tetrazol-5-yl);

(13) when r=1,

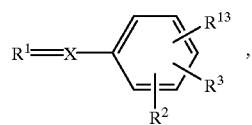

X is a single bond, $R^7$ is Cl, and $R^8$ is —CHO, then $R^{13}$ is not 4-(tetrazol-5-yl).

A preferred embodiment of the invention is the method as recited above, using the imidazole angiotensin II receptor antagonist of formula I:

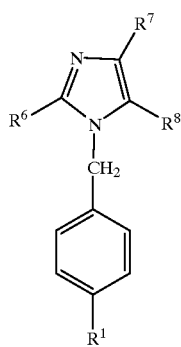

wherein:

$R^1$ is —$CO_2H$; —$NHSO_2CF_3$;

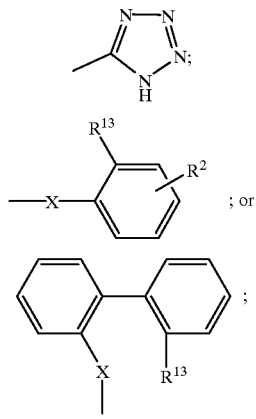

$R^6$ is alkyl of 3 to 10 carbon atoms, alkenyl of 3 to 10 carbon atoms, alkynyl of 3 to 10 carbon atoms, cycloalkyl of 3 to 8 carbon atoms, benzyl substituted on the phenyl ring with up to two groups selected from alkoxy of 1 to 4 carbon atoms, halogen, alkyl of 1 to 4 carbon atoms, and nitro;

$R^8$ is phenylalkenyl wherein the aliphatic portion is 2 to 4 carbon atoms, —$(CH_2)_m$-imidazol-1yl, —$(CH_2)_m$1,2,3-triazolyl optionally substituted with one or two groups selected from $CO_2CH_3$ or alkyl of 1 to 4 carbon atoms, $(CH_2)_m$-tetrazolyl, —$(CH_2)_nOR^{11}$; —$(CH_2)_nOCR^{14}$;

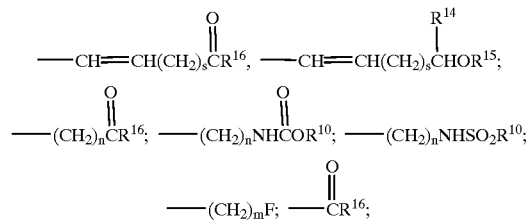

$R^{13}$ is —$CO_2H$, —$CO_2R^9$, $NHSO_2CF_3$; $SO_3H$; or

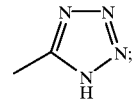

$R^{16}$ is H, alkyl of 1 to 5 carbon atoms, $OR^{17}$, or $NR^{18}R^{19}$;

X is carbon—carbon single bond,

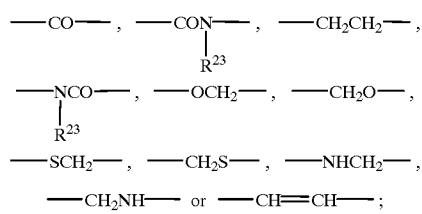

and pharmaceutically acceptable salts of these compounds.

A further preferred embodiment of the invention is the method as recited above, using the imidazole angiotensin II receptor antagonist of formula I:

$R^2$ is H, alkyl of 1 to 4 carbon atoms, halogen, or alkoxy of 1 to 4 carbon atoms;

$R^6$ is alkyl, alkenyl or alkynyl of 3 to 7 carbon atoms;

$R^7$ is H, Cl, Br, $C_vF_{2v+1}$ where v=1–3, or

$R^8$ is

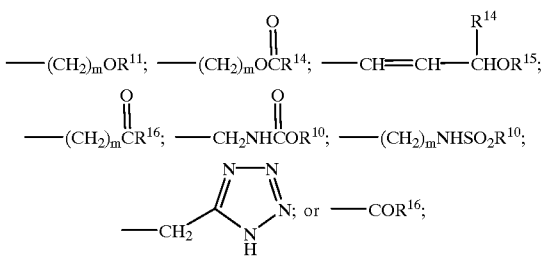

$R^{10}$ is $CF_3$, alkyl of 1 to 6 carbon atoms or phenyl;

$R^{11}$ is H, or alkyl of 1 to 4 carbon atoms;

$R^{13}$ is $CO_2H$; $CO_2CH_2OCOC(CH_3)_3$; $NHSO_2CF_3$; and

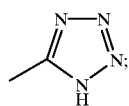

$R^{14}$ is H, or alkyl of 1 to 4 carbon atoms;
$R^{15}$ is H, alkyl of 1 to 4 carbon atoms, or acyl of 1 to 4 carbon atoms;
$R^{16}$ is H, alkyl of 1 to 5 carbon atoms; $OR^{17}$; or

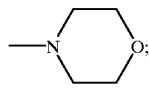

m is 1 to 5;
X is single bond, —O—; —CO—; —NHCO—; or —OCH$_2$—; and pharmaceutically acceptable salts.

A preferred embodiment of this invention is the method as recited above, using an imidazole angiotensin II receptor antagonist selected from the group consisting of:
2-Butyl-4-chloro-1-[(2'-(1H-tetrazol-5-yl)biphenyl-4-yl)methyl]-5-(hydroxymethyl)imidazole.
2-Butyl-4-chloro-1-[(2'-carboxybiphenyl-4-yl)methyl]-5-(hydroxymethyl)imidazole.
2-Butyl-4-chloro-1-[(2'-carboxybiphenyl-4-yl)methyl]-5-[(methoxycarbonyl)aminomethyl]imidazole.
2-Butyl-4-chloro-1-[(2'-carboxybiphenyl-4-yl)methyl]-5-[(propoxycarbonyl)aminomethyl]imidazole.
2-Butyl-4-chloro-1-[(2'-carboxybiphenyl-4-yl)methyl]imidazole-5-carboxaldehyde.
2-Butyl-1-[(2'-carboxybiphenyl-4-yl)methyl]-imidazole-5-carboxaldehyde.
2-(1E-Butenyl)-4-chloro-1-[(2'-carboxybiphenyl-4-yl)methyl]-5-(hydroxymethyl)imidazole.
2-(1E-Butenyl)-4-chloro-1-[(2'-carboxybiphenyl-4-yl)methyl]-imidazole-5-carboxaldehyde.
2-Propyl-4-chloro-1-[(2'-(1H-tetrazol-5-yl)biphenyl-4-yl)methyl]-5-(hydroxymethyl)imidazole.
2-Propyl-4-chloro-1[(2'-(1H-tetrazol-5-yl)biphenyl-4-yl)methyl]-imidazole-5-carboxaldehyde.
2-Butyl-4-chloro-1-[2'-(1H-tetrazol-5-yl)biphenyl-4-yl)methyl]-imidzole-5-carboxaldehyde.
2-(1E-Butenyl)-4-chloro-1-[(2'-(1H-tetrazol-5-yl)biphenyl-4-yl)methyl]-5-hydroxymethyl)imidazole.
2(1E-Butenyl)-4-chloro-1-[(2'-(1H-tetrazol-5-yl)biphenyl-4-yl)methyl]imidazole-5-carboxaldehyde.
2-Butyl-4-chloro-1-[(2'-(1H-tetrazol-5-yl)-biphenyl-4-yl)methyl]-imidazole-5-carboxylic acid.
2-Propyl-4-chloro-1-[(2-'(1H-tetrazol-5-yl)-biphenyl-4-yl)methyl]-imidazole-5-carboxylic acid. 2-Propyl-4-trifluoromethyl-1-[(2'-(1H-tetrazol-5-yl)biphenyl-4-yl)methyl]imidazole-5-carboxylic acid.
2-Propyl-4-trifluoromethyl-1-[(2'-(1H-tetrazol-5-yl)biphenyl-4-yl)methyl]-5-(hydroxylmethyl)imidazole.
2-Butyl-4-trifluoromethyl-1[(2'-(1H-tetrazol-5-yl)biphenyl-4-yl)methyl]imidazole-5-carboxylic acid.
2-Propyl-4-trifluoromethyl-1-[(2'-(carboxybiphenyl-4-yl)methyl]-imidazole-5-carboxaldehyde.
2-Propyl-4-pentafluoroethyl-1-[(2'-(1H-tetrazol-5-yl)biphenyl-4-yl)methyl]-5-(hydroxymethyl)imidazole.
2-Propyl-1-[(2-(1H-tetrazol-5-yl)biphenyl-4-yl)methyl]imidazole-4,5,-dicarboxylic acid.
2-Propyl-4-pentafluoroethyl-1-[(2'-(1H-tetrazol-5-yl)biphenyl-4-yl)methyl]imidazole-5-carboxylic acid.
2-Propyl-4-pentafluoroethyl-[(2'-(1H-tetrazol-5-yl)biphenyl-4-yl)methyl]imidazole-5-carboxaldehyde,
or its pharmaceutically acceptable salt thereof.

A more preferred embodiment of the invention is the method as recited above, using the imidazole angiotensin II receptor antagonist of formula I:
2-Butyl-4-chloro-1-[(2'-tetrazol-5-yl)biphenyl-4-yl]methyl]-5-(hydroxymethyl)imidazole (also known as losartan); and
2-Butyl-4-chloro-1-[(2'-tetrazol-5-yl)biphenyl-4-yl]methylimidazole-5-carboxylic acid (also known as EXP-3174) or its pharmaceutically acceptable salt thereof. The most preferrred embodiment is the method, as recited above, wherein the symptomatic heart failure patient is age 65 or older.

This invention also relates to a method for reducing sudden cardiac death by administering to a symptomatic heart failure patient a therapeutically effective amount of an angiotensin II antagonist.

An embodiment of this invention is the method for reducing sudden cardiac death by administering to a symptomatic heart failure patient a therapeutically effective amount of an angiotensin II receptor antagonist selected from the group consisting of: candesartan cilexetil, eprosartan, irbesartan, losartan, tasosartan, telmisartan, valsartan, BMS-184698, 3-(2'-(tetrazol-5-yl)-1,1'-biphen-4-yl)methyl-5,7-dimethyl-2-ethyl-3H-imidazo[4,5-b]pyridine, BAY106734, BIBR363, CL329167, E4177, EMD73495, HN65021, HR720, HOE720, LRB081, SC52458, SL910102, UP2696, YM358, EMD66397, ME3221, TAK536, BMS184698, CGP42112A, CGP49870, CP148130, E4188, EMD66684, EXP9954, FR1153332, GA0050, KT3579, LF70156, LRB057, LY266099, LY301875, PD123177, PD126055, SC51757, SC54629, U96849, UK77778, WAY126227, WK1260, WK1492, YH1498, and YM31472. The preferred angiotensin II receptor antagonists useful in this method are: candesartan cilexetil, eprosartan, irbesartan, losartan, tasosartan, telmisartan, valsartan, BMS-194698 and 3-(2'-(tetrazol-5-yl)-1,1'-biphen-4-yl)methyl-5,7-dimethyl-2-ethyl-3H-imidazo[4,5-b]pyridine.

Yet another embodiment of the invention is a method for reducing sudden cardiac death by administering to a symptomatic heart failure patient a therapeutically effective amount of an angiotensin II receptor antagonist of formula I

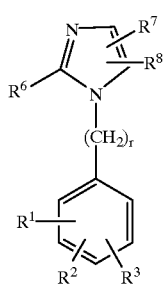

wherein:

$R^1$ is:

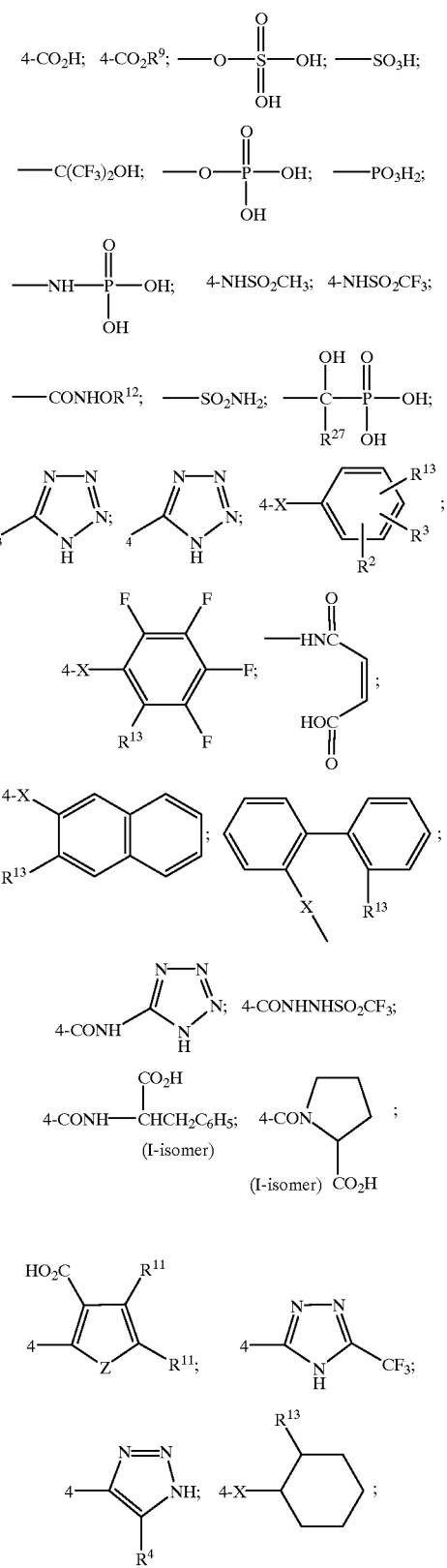

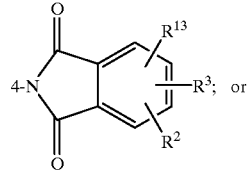

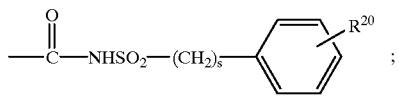

$R^2$ is H; Cl; Br; I; F; $NO_2$; CN; alkyl of 1 to 4 carbon atoms; acyloxy of 1 to 4 carbon atoms; alkoxy of 1 to 4 carbon atoms; $CO_2H$; $CO_2R^9$; $HNSO_2CH_3$; $NHSO_2CF_3$; $CONHOR^{12}$; $SO_2NH_2$;

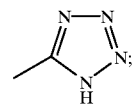

aryl; or furyl;

$R^3$ is H; Cl, Br, I or F; alkyl of 1 to 4 carbon atoms or alkoxy of 1 to 4 carbon atoms;

$R^4$ is CN, $NO_2$ or $CO_2R^{11}$;

$R^5$ is H, alkyl of 1 to 6 carbon atoms, cycloalkyl of 3 to 6 carbon atoms alkenyl or alkynyl of 2 to 4 carbon atoms;

$R^6$ is alkyl of 2 to 10 carbon atoms, alkenyl or alkynyl of 3 to 10 carbon atoms or the same groups substituted with F or $CO_2R^{14}$; cycloalkyl of 3 to 9 carbon atoms, cycloalkylalkyl, of 4 to 10 carbon atoms; cycloalkylalkenyl or cycloalkylalkynyl 5 to 10 carbon atoms; $(CH_2)_sZ(CH_2)_mR^5$ optionally substituted with F or $CO_2R^{14}$; benzyl substituted on the phenyl ring with 1 or 2 halogens, alkoxy of 1 to 4 carbon atoms, alkyl of 1 to 4 carbon atoms or nitro;

$R^7$ is H, F, Cl, Br, I, $NO_2$, $C_vF_{2v+1}$, where v=1–6, $C_6F_5$; CN;

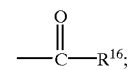

straight or branched alkyl of 1 to 6 carbon atoms; phenyl or phenylalkyl, where alkyl is 1 to 3 carbon atoms; or substituted phenyl or substituted phenylalkyl, where alkyl is 1 to 3 carbon atoms, substituted with one or two substituents selected from alkyl of 1 to 4 carbon atoms, F, Cl, Br, OH, $OCH_3$, $CF_3$, and COOR, where R is H, alkyl of 1 to 4 carbon atoms, or phenyl;

$R^8$ is H, CN, alkyl of 1 to 10 carbon atoms, alkenyl of 3 to 10 carbon atoms, or the same groups substituted with F; phenylalkenyl wherein the aliphatic portion is 2 to 6 carbon atoms; —$(CH_2)_m$-imidazol-1-yl; —$(CH_2)_m$-1,2,3-triazolyl optionally substituted with one or two group selected from $CO_2CH_3$ or alkyl of 1 to 4 carbon atoms; —$(CH_2)_s$ tetrazolyl;

$—(CH_2)_{n-1}CH—R^{11}$;  $—(CH_2)_nOCR^{14}$;  $—(CH_2)_nSR^{15}$;
        |
        $OR^{17}$ $—CH=CH(CH_2)_sCHOR^{15}$;  $—CH=CH(CH_2)_sCR^{16}$;
            |
            $R^{14}$ $—CR^{16}$;  $—CH=CH(CH_2)_sOCR^{11}$;

$(CH_2)_s—CH—COR^{16}$;  $—(CH_2)_nCR^{16}$;
         |
         $CH_3$ $—(CH_2)_nOCNHR^{10}$;  $—(CH_2)_nNR^{11}COR^{10}$;  (Y above C=)

$—(CH_2)_nNR^{11}CNHR^{10}$;  $—(CH_2)_nNR^{11}SO_2R^{10}$;

$—(CH_2)_nNR^{11}CR^{10}$ (Y);  $—(CH_2)_mF$;  $—(CH_2)_mONO_2$;

$—CH_2N_3$;  $—(CH_2)_mNO_2$;  $—CH=N—NR^{11}R^{17}$;

$—(CH_2)_m$-phthalimide;

$—(CH_2)_s$-triazole($R^4$, NH);  $—(CH_2)_s$-triazole($CF_3$, H);

$—(CH_2)_n$-piperazinyl-(2-methoxyphenyl);

$—(CH_2)_{n-1}C(O)$-piperazinyl-(2-methoxyphenyl);

$—CH=N—NH—SO_2$-phenyl; or $—CH=N—NH$-imidazoline;

$R^9$ is:

$—CH—OCR^{21}$
  |
  $R^{24}$  (C=O)

$R^{10}$ is alkyl of 1 to 6 carbon atoms or perfluoroalkyl of 1 to 6 carbon atoms, 1-adamantyl, 1-naphthyl, 1-(1-naphthyl)ethyl, or $(CH_2)_pC_6H_5$;

$R^{11}$ is H, alkyl of 1 to 6 carbon atoms, cycloalkyl of 3 to 6 carbon atoms, phenyl or benzyl;

$R^{12}$ is H, methyl or benzyl;

$R^{13}$ is $—CO_2H$;  $—CO_2R^9$;  $—CH_2CO_2H$;  $—CH_2CO_2R^9$;

$—O—S(=O)_2—OH$ (OH);  $—O—P(=O)(OH)—OH$;  $—SO_3H$;

$—NHP(=O)(OH)—OH$;  $—C(R^{27})(OH)—P(=O)(OH)—OH$;  $—PO_3H_2$;

$—C(CF_3)_2OH$;  $—NHSO_2CH_3$;  $—NHSO_2CF_3$;

$—NHCOCF_3$;  $—CONHOR^{12}$;  $—SO_2NH_2$;

methyl-tetrazole-$R^{31}$;  $—CH_2$-tetrazole;  $—CONH$-tetrazole;

$—CONHNHSO_2CF_3$;  methyl-triazole-$CF_3$; or methyl-tetrazole-$R_4$;

$R^{14}$ is H, alkyl or perfluoroalkyl of 1 to 8 carbon atoms, cycloalkyl of 3 to 6 carbon atoms, phenyl or benzyl;

$R^{15}$ is H, alkyl of 1 to 6 carbon atoms, cycloalkyl of 3 to 6 carbon atoms, phenyl, benzyl, acyl of 1 to 4 carbon atoms, phenacyl;

$R^{16}$ is H, alkyl of 1 to 6 carbon atoms, cycloalkyl of 3 to 6 carbon atoms, $(CH_2)_pC_6H_5$, $OR^{17}$, or $NR^{18}R^{19}$;

$R^{17}$ is H, alkyl of 1 to 6 carbon atoms, cycloalkyl of 3 to 6 carbon atoms, phenyl or benzyl;

$R^{18}$ and $R^{19}$ independently are H, alkyl of 1 to 4 carbon atoms, phenyl, benzyl, α-methylbenzyl, or taken together with the nitrogen form a ring of the formula;

$—N$-ring-$(CH_2)_t$-Q;

Q is $NR_{20}$, O or $CH_2$;

$R^{20}$ is H, alkyl of 1–4 carbon atoms, or phenyl;

$R^{21}$ is alkyl of 1 to 6 carbon atoms, —$NR^{22}R^{23}$, or

$R^{22}$ and $R^{23}$ independently are H, alkyl of 1 to 6 carbon atoms, benzyl, or are taken together as $(CH_2)_u$, where u is 3–6;

$R^{24}$ is H, $CH_3$ or —$C_6H_5$;

$R^{25}$ is $NR^{27}R^{28}$, $OR^{28}$, $NHCONH_2$, $NHCSNH_2$,

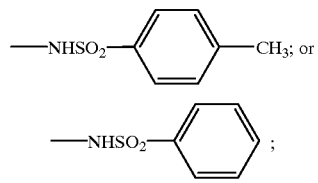

$R^{26}$ is hydrogen, alkyl with from 1 to 6 carbon atoms, benzyl, or allyl;

$R^{27}$ and $R^{28}$ are independently hydrogen, alkyl with from 1 to 5 carbon atoms, or phenyl;

$R^{29}$ and $R^{30}$ are independently alkyl of 1–4 carbon atoms or taken together are —$(CH_2)_q$—;

$R^{31}$ is H, alkyl or 1 to 4 carbon atoms, —$CH_2CH=CH_2$ or —$CH_2C_6H_4R^{32}$;

X is a carbon—carbon single bond,

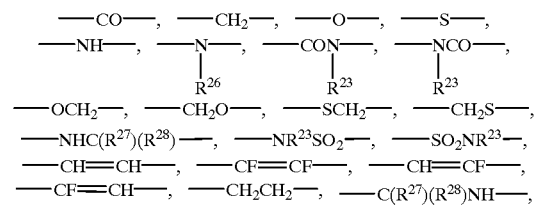
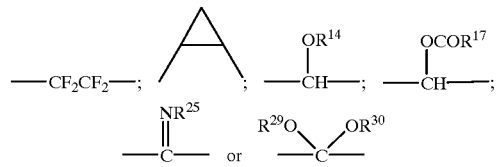

Y is O or S;

Z is O, $NR^{11}$, or S;

m is 1 to 5;

n is 1 to 10;

p is 0 to 3;

q is 2 to 3;

r is 0 to 2;

s is 0 to 5;

t is 0 or 1;

and pharmaceutically acceptable salts of these compounds; provided that:

(1) the $R^1$ group is not in the ortho position;

(2) when $R^1$ is

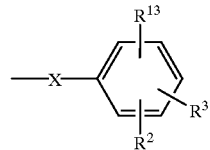

X is a single bond, and $R^{13}$ is $CO_2H$, or

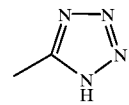

then $R^{13}$ must be in the ortho or meta position; or when $R^1$ and X are as above and $R^{13}$ is $NHSO_2CF_3$ or $NHSO_2CH_3$, $R^{13}$ must be ortho;

(3) when $R^1$ is

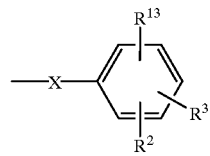

and X is other than a single bond, then $R^{13}$ must be ortho except when X=$NR^{23}CO$ and $R^{13}$ is $NHSO_2CF_3$ or $NHSO_2CH_3$, then $R^{13}$ must be ortho or meta;

(4) when $R^1$ is 4-$CO_2H$ or a salt thereof, $R^6$ cannot be S-alkyl;

(5) when $R^1$ is 4-$CO_2H$ or a salt thereof, the substituent on the 4-position of the imidazole cannot be $CH_2OH$, $CH_2OCOCH_3$, or $CH_2CO_2H$;

(6) when $R^1$ is

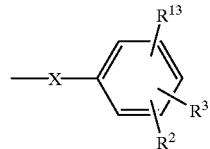

X is —$OCH_2$—, and $R^{13}$ is 2-$CO_2H$, and $R^7$ is H then $R^6$ is not $C_2H_5S$;

(7) when $R^1$ is

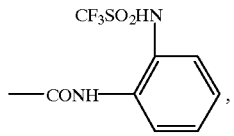

and $R^6$ is n-hexyl then $R^7$ and $R^8$ are not both hydrogen;

(8) when $R^1$ is

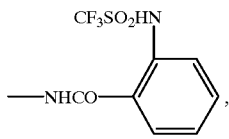

$R^6$ is not methoxybenzyl;

(9) the $R^6$ group is not

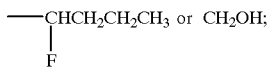

(10) when r=0, $R^1$ is

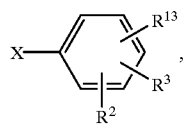

X is

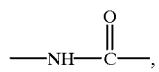

$R^{13}$ is 2-NHSO$_2$CF$_3$, and $R^6$ is n-propyl, then $R^7$ and $R^8$ are not —CO$_2$CH$_3$;

(11) when r=0, $R^1$ is

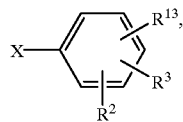

X is

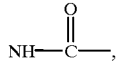

$R^{13}$ is 2-COOH, and $R^6$ is n-propyl, then $R^7$ and $R^8$ are not —CO$_2$CH$_3$;

(12) when r=1,

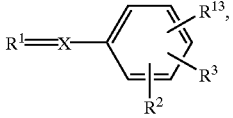

X is a single bond, $R^7$ is Cl, and $R^8$ is —CHO, then $R^{13}$ is not 3-(tetrazol-5-yl);

(13) when r=1,

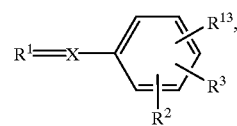

X is a single bond, $R^7$ is Cl, and $R^8$ is —CHO, then $R^{13}$ is not 4-(tetrazol-5-yl).

A preferred embodiment of the method as recited above, wherein the angiotensin II receptor antagonist is losartan or EXP-3174 or a pharmaceutically acceptable salt thereof. The most preferred embodiment is the method, as recited above, wherein the symptomatic heart failure patient is age 65 or older.

This invention also concerns a method for reducing mortality and sudden cardiac death by administering to a symptomatic heart failure patient a therapeutically effective amount of an angiotensin II receptor antagonist.

An embodiment of this invention is the method for reducing mortality and sudden cardiac death by administering to a symptomatic heart failure patient a therapeutically effective amount of an angiotensin II receptor antagonist selected from the group consisting of: candesartan cilexetil, eprosartan, irbesartan, losartan, tasosartan, telmisartan, valsartan, BMS-184698, 3-(2'-(tetrazol-5-yl)-1,1'-biphen-4-yl)methyl-5,7-dimethyl-2-ethyl-3H-imidazo[4,5-b]pyridine, BAY106734, BIBR363, CL329167, E4177, EMD73495, HN65021, HR720, HOE720, LRB081, SC52458, SL910102, UP2696, YM358, EMD66397, ME3221, TAK536, BMS184698, CGP42112A, CGP49870, CP148130, E4188, EMD66684, EXP9954, FR1153332, GA0050, KT3579, LF70156, LRB057, LY266099, LY301875, PD123177, PD126055, SC51757, SC54629, U96849, UK77778, WAY126227, WK1260, WK 1492, YH1498, and YM31472. The preferred angiotensin II receptor antagonists useful in this method are: candesartan cilexetil, eprosartan, irbesartan, losartan, tasosartan, telmisartan, valsartan, BMS-184698 and 3-(2'-(tetrazol-5-yl)-1,1'-biphen-4-yl)methyl-5,7-dimethyl-2-ethyl-3H-imidazo[4,5-b]pyridine.

Yet another embodiment of the invention is a method for reducing mortality and sudden cardiac death by administering to a symptomatic heart failure patient a therapeutically effective amount of an angiotensin II antagonist formula I

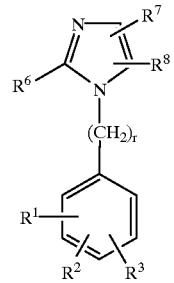

I wherein:

$R^1$ is:

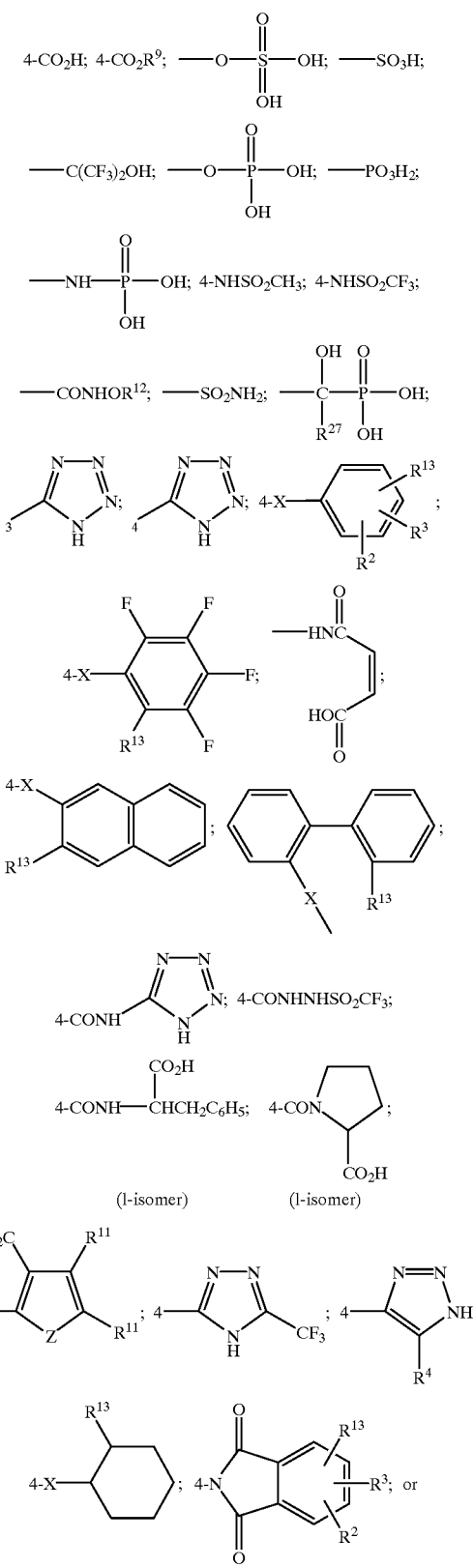

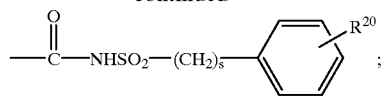

$R^2$ is H; Cl; Br; I; F; $NO_2$; CN; alkyl of 1 to 4 carbon atoms; acyloxy of 1 to 4 carbon atoms; alkoxy of 1 to 4 carbon atoms; $CO_2H$; $CO_2R^9$; $HNSO_2CH_3$; $NHSO_2CF_3$; $CONHOR^{12}$; $SO_2NH_2$;

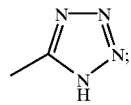

aryl; or furyl;

$R^3$ is H; Cl, Br, I or F; alkyl of 1 to 4 carbon atoms or alkoxy of 1 to 4 carbon atoms;

$R^4$ is CN, $NO_2$ or $CO_2R^{11}$;

$R^5$ is H, alkyl of 1 to 6 carbon atoms, cycloalkyl of 3 to 6 carbon atoms alkenyl or alkynyl of 2 to 4 carbon atoms;

$R^6$ is alkyl of 2 to 10 carbon atoms, alkenyl or alkynyl of 3 to 10 carbon atoms or the same groups substituted with F or $CO_2R^{14}$; cycloalkyl of 3 to 8 carbon atoms, cycloalkylalkyl, of 4 to 10 carbon atoms; cycloalkylalkenyl or cycloalkylalkynyl 5 to 10 carbon atoms; $(CH_2)_sZ(CH_2)_mR^5$ optionally substituted with F or $CO_2R^{14}$; benzyl substituted on the phenyl ring with 1 or 2 halogens, alkoxy of 1 to 4 carbon atoms, alkyl of 1 to 4 carbon atoms or nitro;

$R^7$ is H, F, Cl, Br, I, $NO_2$, $C_vF_{2v+1}$, where v=1–6, $C_6F_5$; CN;

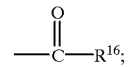

straight or branched alkyl of 1 to 6 carbon atoms; phenyl or phenylalkyl, where alkyl is 1 to 3 carbon atoms; or substituted phenyl or substituted phenylalkyl, where alkyl is 1 to 3 carbon atoms, substituted with one or two substituents selected from alkyl of 1 to 4 carbon atoms, F, Cl, Br, OH, $OCH_3$, $CF_3$, and COOR, where R is H, alkyl of 1 to 4 carbon atoms, or phenyl;

$R^8$ is H, CN, alkyl of 1 to 10 carbon atoms, alkenyl of 3 to 10 carbon (atoms, or the same groups substituted with F; phenylalkenyl wherein the aliphatic portion is 2 to 6 carbon atoms; $-(CH_2)_m$-imidazol-1-yl; $-(CH_2)_m$ -1,2,3-triazolyl optionally substituted with one or two group selected from $CO_2CH_3$ or alkyl of 1 to 4 carbon atoms; $-(CH_2)_s$ tetrazolyl;

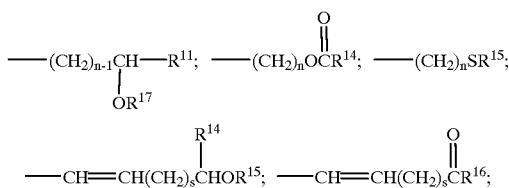

-continued

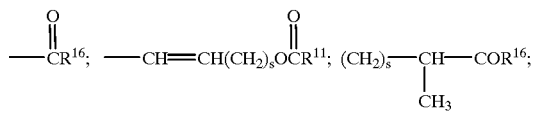

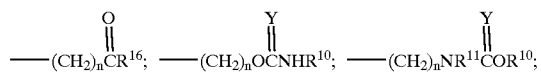

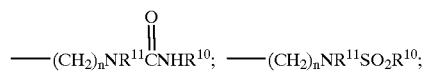

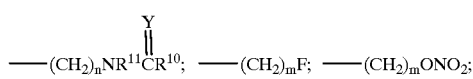

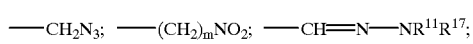

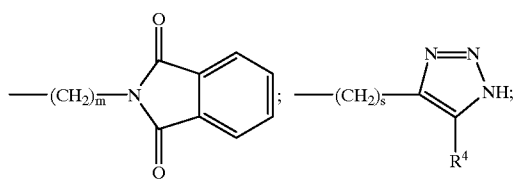

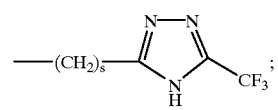

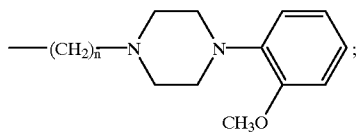

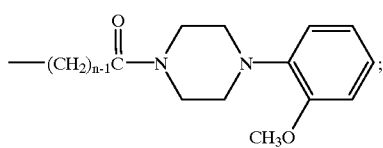

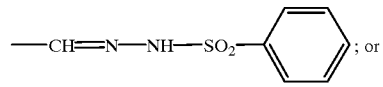

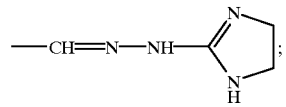

$R^9$ is:

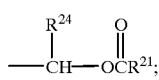

$R^{10}$ is alkyl of 1 to 6 carbon atoms or perfluoroalkyl of 1 to 6 carbon atoms, 1-adamantyl, 1-naphthyl, 1-(1-naphthyl)ethyl, or $(CH_2)_pC_6H_5$;

$R^{11}$ is H, alkyl of 1 to 6 carbon atoms, cycloalkyl of 3 to 6 carbon atoms, phenyl or benzyl;

$R^{12}$ is H, methyl or benzyl;

$R^{13}$ is

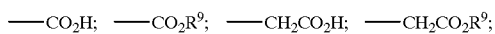

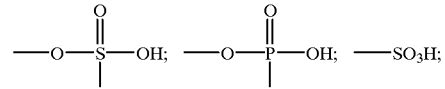

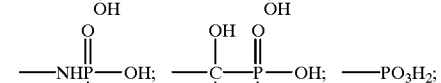

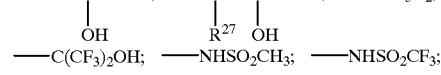

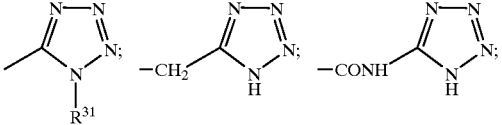

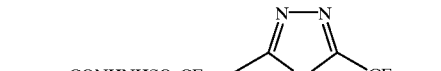

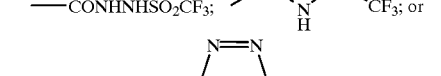

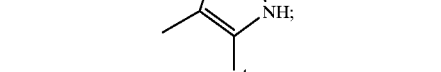

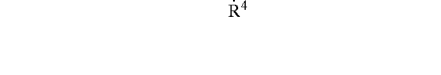

$R^{14}$ is H, alkyl or perfluoroalkyl of 1 to 8 carbon atoms, cycloalkyl of 3 to 6 carbon atoms, phenyl or benzyl;

$R^{15}$ is H, alkyl of 1 to 6 carbon atoms, cycloalkyl of 3 to 6 carbon atoms, phenyl, benzyl, acyl of 1 to 4 carbon atoms, phenacyl;

$R^{16}$ is H, alkyl of 1 to 6 carbon atoms, cycloalkyl of 3 to 6 carbon atoms, $(CH_2)_pC_6H_5$, $OR^{17}$, or $NR^{18}R^{19}$;

$R^{17}$ is H, alkyl of 1 to 6 carbon atoms, cycloalkyl of 3 to 6 carbon atoms, phenyl or benzyl;

$R^{18}$ and $R^{19}$ independently are H, alkyl of 1 to 4 carbon atoms, phenyl, benzyl, α-methylbenzyl, or taken together with the nitrogen form a ring of the formula

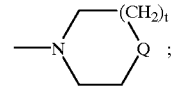

Q is $NR^{20}$, O or $CH_2$;

$R^{20}$ is H, alkyl of 1–4 carbon atoms, or phenyl;

$R^{21}$ is alkyl of 1 to 6 carbon atoms, $-NR^{22}R^{23}$, or

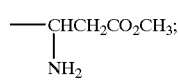

$R^{22}$ and $R^{23}$ independently are H, alkyl of 1 to 6 carbon atoms, benzyl, or are taken together as $(CH_2)_u$, where u is 3–6;

$R^{24}$ is H, $CH_3$ or $—C_6H_5$;

$R^{25}$ is $NR^{27}R^{28}$, $OR^{28}$, $NHCONH_2$, $NHCSNH_2$,

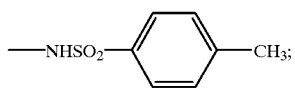

or

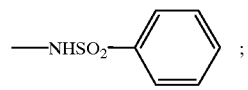

;

$R^{26}$ is hydrogen, alkyl with from 1 to 6 carbon atoms, benzyl, or allyl;

$R^{27}$ and $R^{28}$ are independently hydrogen, alkyl with from 1 to 5 carbon atoms, or phenyl;

$R^{29}$ and $R^{30}$ are independently alkyl of 1–4 carbon atoms or taken together are $—(CH_2)_q—$;

$R^{31}$ is H, alkyl or 1 to 4 carbon atoms, $—CH_2CH=CH_2$ or $—CH_2C_6H_4R^{32}$;

X is a carbon—carbon single bond,

—CO—, —CH$_2$—, —O—, —S—, —NH—,

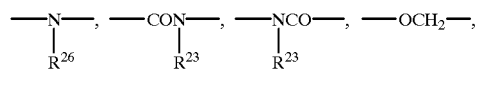

—CH$_2$O—, —SCH$_2$—, —CH$_2$S—,

—NHC(R$^{27}$)(R$^{28}$)—, —NR$^{23}$SO$_2$—, —SO$_2$NR$^{23}$—,

—CH=CH—, —CF=CF—, —CH=CF—,

—CF=CH—, —CH$_2$CH$_2$—, —C(R$^{27}$)(R$^{28}$)NH—,

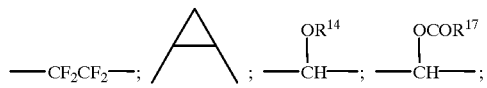

Y is O or S;

Z is O, $NR^{11}$, or S;

m is 1 to 5;

n is 1 to 10;

p is 0 to 3;

q is 2 to 3;

r is 0 to 2;

s is 0 to 5;

t is 0 or 1;

and pharmaceutically acceptable salts of these compounds; provided that:

(1) the $R^1$ group is not in the ortho position;

(2) when $R^1$ is

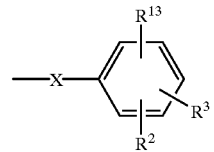

X is a single bond, and $R^{13}$ is $CO_2H$, or

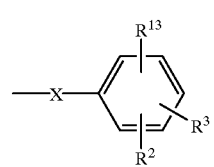

then $R^{13}$ must be in the ortho or meta position; or when $R^1$ and X are as above and $R^{13}$ is $NHSO_2CF_3$ or $NHSO_2CH_3$, $R^{13}$ must be ortho;

(3) when $R^1$ is

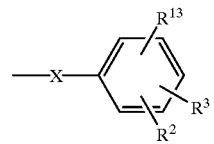

and X is other than a single bond, then $R^{13}$ must be-ortho except when X=$NR^{23}CO$ and $R^{13}$ is $NHSO_2CF_3$ or $NHSO_2CH_3$, then $R^{13}$ must be ortho or meta;

(4) when $R^1$ is 4-$CO_2H$ or a salt thereof, $R^6$ cannot be S-alkyl;

(5) when $R^1$ is 4-$CO_2H$ or a salt thereof, the substituent on the 4-position of the imidazole cannot be $CH_2OH$, $CH_2OCOCH_3$, or $CH_2CO_2H$;

(6) when $R^1$ is

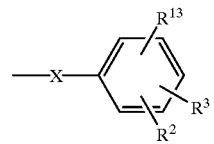

X is $—OCH_2—$, and $R^{13}$ is 2-$CO_2H$, and $R^7$ is H then $R^6$ is not $C_2H_5S$;

(7) when $R^1$ is

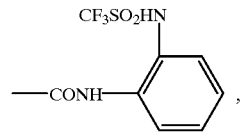

and $R^6$ is n-hexyl then $R^7$ and $R^8$ are not both hydrogen;

(8) when $R^1$ is

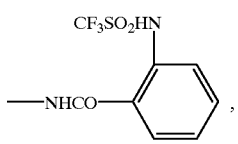

$R^6$ is not methoxybenzyl;

(9) the $R^6$ group is not

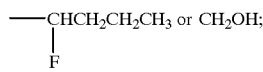

(10) when r=0, $R^1$ is

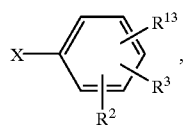

X is

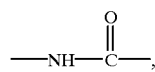

$R^{13}$ is 2-NHSO$_2$CF$_3$, and $R^6$ is n-propyl, then $R^7$ and $R^8$ are not —CO$_2$CH$_3$;

(11) when r=0, $R^1$ is

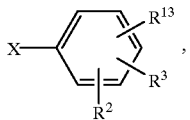

X is

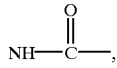

$R^{13}$ is 2-COOH, and $R^6$ is n-propyl, then $R^7$ and $R^8$ are not —CO$_2$CH$_3$;

(12) when r=1,

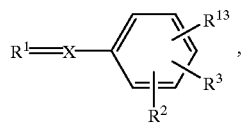

X is a single bond, $R^7$ is Cl, and $R^8$ is —CHO, then $R^{13}$ is not 3-(tetrazol-5-yl);

(13) when r=1,

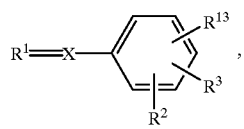

X is a single bond, $R^7$ is Cl, and $R^8$ is —CHO, then $R^{13}$ is not 4-(tetrazol-5-yl).

A preferred embodiment of the invention is the method as recited above, wherein the angiotensin II receptor antagonist is losartan or EXP-3174 or a pharmaceutically acceptable salt thereof. The most preferred embodiment is the method, as recited above, wherein the symptomatic heart failure patient is age 65 or older.

Additionally, the invention concerns a method for preventing sudden cardiac death by administering to a symptomatic heart failure patient a therapeutically effective amount of an angiotensin II receptor antagonist.

An embodiment of this invention is the method for preventing sudden cardiac death by administering to a symptomatic heart failure patient a therapeutically effective amount of an angiotensin II receptor antagonist selected from the group consisting of: candesartan cilexetil, eprosartan, irbesartan, losartan, tasosartan, telmisartan, valsartan, BMS-184699, 3-(2'-(tetrazol-5-yl)-1,1'-biphen-4-yl)methyl-5,7-dimethyl-2-ethyl-3H-imidazo[4,5-b]pyridine, BAY106734, BIBR363, CL329167, E4177, EMD73495, HN65021, HR720, HOE720, LRB081, SC52458, SL910102, UP2696, YM358, EMD66397, ME3221, TAK536, BMS184698, CGP42112A, CGP49870, CP148130, E4188, EMD66684, EXP9954, FRI 153332, GA0050, KT3579, LF70156, LRB057, LY266099, LY301875, PD123177, PD126055, SC51757, SC54629, U96849, UK77778, WAY126227, WK1260, WK1492, YH1498, and YM31472. The preferred angiotensin II receptor antagonists useful in this method are: candesartan cilexetil, eprosartan, irbesartan, losartan, tasosartan, telmisartan, valsartan, BMS-184698 and 3-(2'-(tetrazol-5-yl)-1,1'-biphen-4-yl)methyl-5,7-dimethyl-2-ethyl-3H-imidazo[4,5-b]pyridine.

Yet another embodiment of the invention is a method for preventing sudden cardiac death by administering to a symptomatic heart failure patient a therapeutically effective amount of an angiotensin II receptor antagonist of formula I

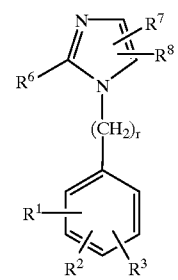

wherein:

R¹ is:

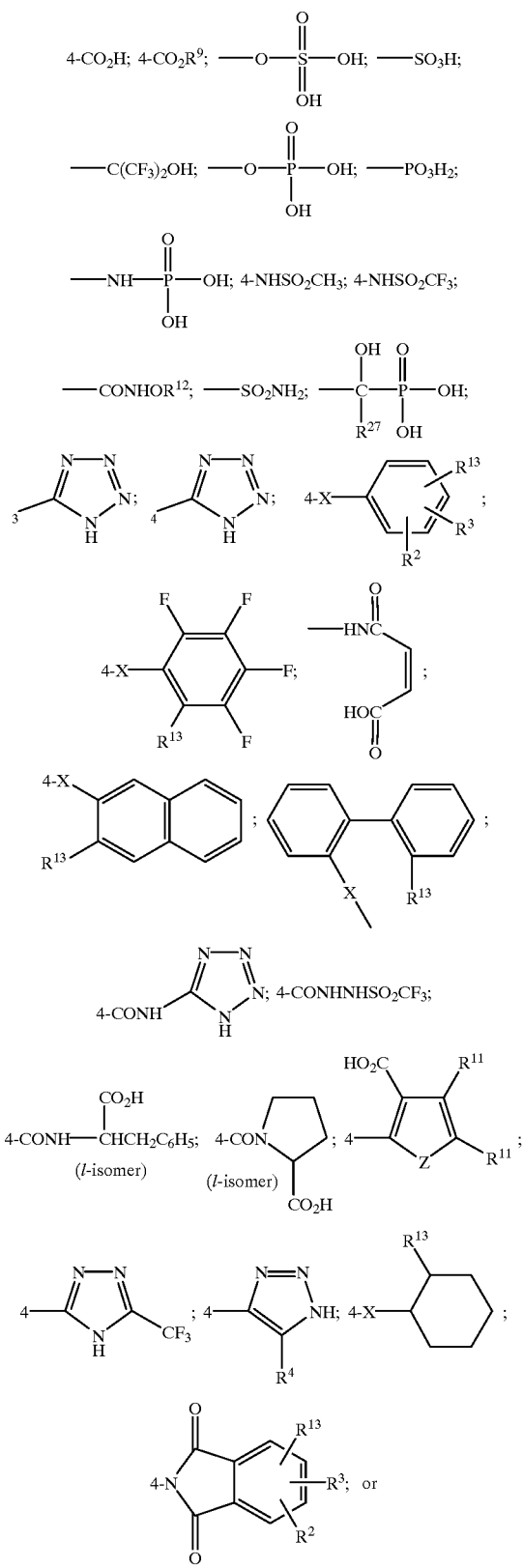

R² is H; Cl; Br; I; F; $NO_2$; CN; alkyl of 1 to 4 carbon atoms; acyloxy of 1 to 4 carbon atoms; alkoxy of 1 to 4 carbon atoms; $CO_2H$; $CO_2R^9$; $HNSO_2CH_3$; $NHSO_2CF_3$; $CONHOR^{12}NH_2$;

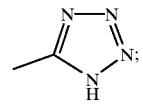

aryl; or furyl;

R³ is H; Cl, Br, I or F; alkyl of 1 to 4 carbon atoms or alkoxy of 1 to 4 carbon atoms;

R⁴ is CN, $NO_2$ or $CO_2R^{11}$;

R⁵ is H, alkyl of 1 to 6 carbon atoms, cycloalkyl of 3 to 6 carbon atoms alkenyl or alkynyl of 2 to 4 carbon atoms;

R⁶ is alkyl of 2 to 10 carbon atoms, alkenyl or alkynyl of 3 to 10 carbon atoms or the same groups substituted with F or $CO_2R^{14}$; cycloalkyl of 3 to 8 carbon atoms, cycloalkylalkyl, of 4 to 10 carbon atoms; cycloalkylalkenyl or cycloalkylalkynyl 5 to 10 carbon atoms; $(CH_2)_sZ(CH_2)_mR^5$ optionally substituted with F or $CO_2R^{14}$; benzyl substituted on the phenyl ring with 1 or 2 halogens, alkoxy of 1 to 4 carbon atoms, alkyl of 1 to 4 carbon atoms or nitro;

R⁷ is H, F, Cl, Br, I, $NO_2$, $C_vF_{2v+1}$, where v=1–6, $C_6F_5$; CN;

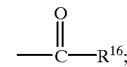

straight or branched alkyl of 1 to 6 carbon atoms; phenyl or phenylalkyl, where alkyl is 1 to 3 carbon atoms; or substituted phenyl or substituted phenylalkyl, where alkyl is 1 to 3 carbon atoms, substituted with one or two substituents selected from alkyl of 1 to 4 carbon atoms, F, Cl, Br, OH, $OCH_3$, $CF_3$, and COOR, where R is H, alkyl of 1 to 4 carbon atoms, or phenyl;

R⁸ is H, CN, alkyl of 1 to 10 carbon atoms, alkenyl of 3 to 10 carbon atoms, or the same groups substituted with F; phenylalkenyl wherein the aliphatic portion is 2 to 6 carbon atoms; $-(CH_2)_m$-imidazol-1-yl; $-(CH_2)_m$-1,2,3-triazolyl optionally substituted with one or two group selected from $CO_2CH_3$ or alkyl of 1 to 4 carbon atoms; $-(CH_2)_s$ tetrazolyl;

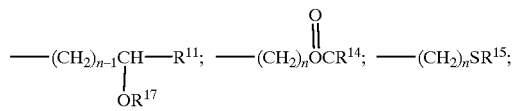

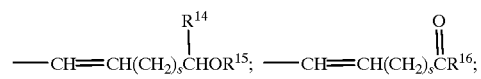

-continued

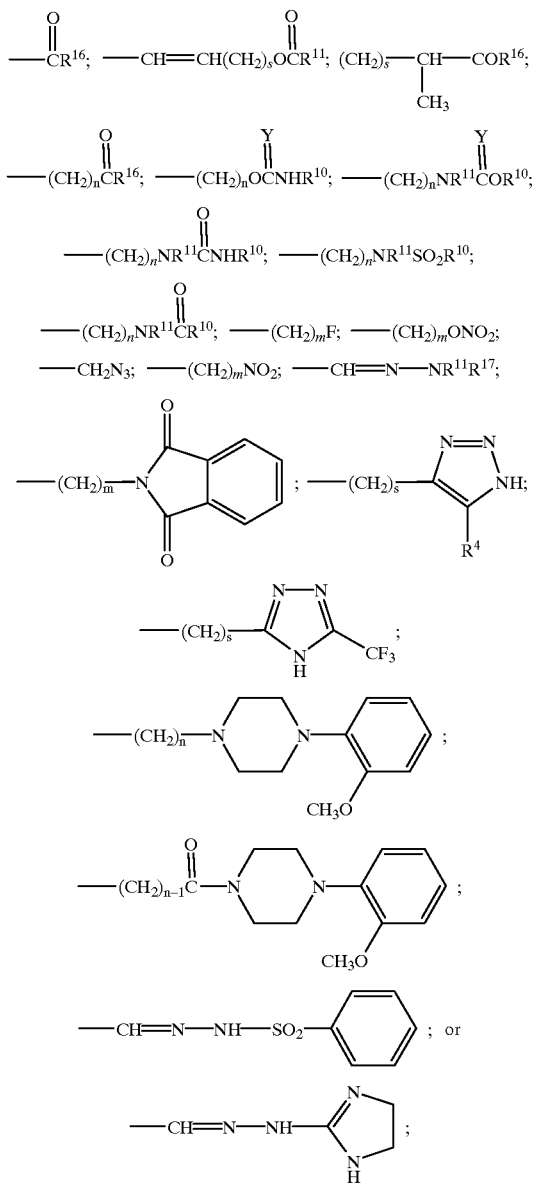

$R^9$ is:

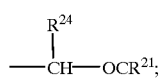

$R^{10}$ is alkyl of 1 to 6 carbon atoms or perfluoroalkyl of 1 to 6 carbon atoms, 1-adamantyl, 1-naphthyl, 1-(1-naphthyl)ethyl, or $(CH_2)_pC_6H_5$;

$R^{11}$ is H, alkyl of 1 to 6 carbon atoms, cycloalkyl of 3 to 6 carbon atoms, phenyl or benzyl;

$R^{12}$ is H, methyl or benzyl;

$R^{13}$ is

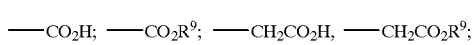

-continued

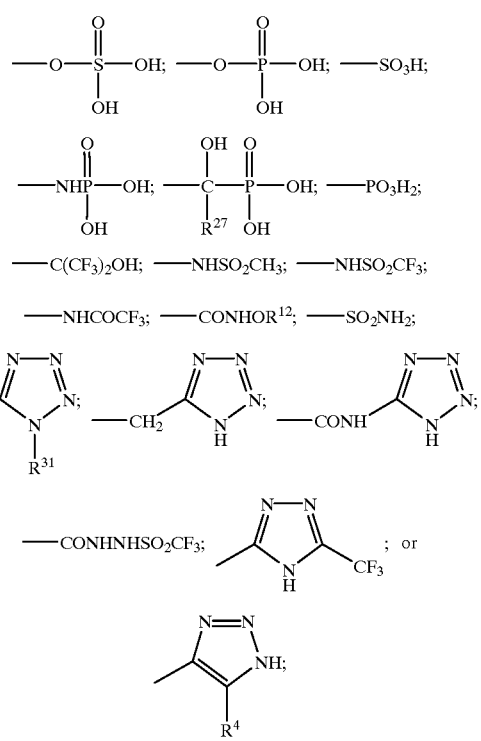

$R^{14}$ is H, alkyl or perfluoroalkyl of 1 to 9 carbon atoms, cycloalkyl of 3 to 6 carbon atoms, phenyl or benzyl;

$R^{15}$ is H, alkyl of 1 to 6 carbon atoms, cycloalkyl of 3 to 6 carbon atoms, phenyl, benzyl, acyl of 1 to 4 carbon atoms, phenacyl;

$R^{16}$ is H, alkyl of 1 to 6 carbon atoms, cycloalkyl of 3 to 6 carbon atoms, $(CH_2)_pC_6H_5$, $OR^{17}$, or $NR^{18}R^{19}$;

$R^{17}$ is H, alkyl of 1 to 6 carbon atoms, cycloalkyl of 3 to 6 carbon atoms, phenyl or benzyl;

$R^{18}$ and $R^{19}$ independently are H, alkyl of 1 to 4 carbon atoms, phenyl, benzyl, α-methylbenzyl, or taken together with the nitrogen form a ring of the formula

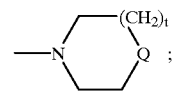

Q is $NR^{20}$, O or $CH_2$;

$R^{20}$ is H, alkyl of 1–4 carbon atoms, or phenyl;

$R^{21}$ is alkyl of 1 to 6 carbon atoms, $-NR^{22}R^{23}$, or

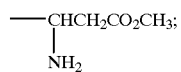

$R^{22}$ and $R^{23}$ independently are H, alkyl of 1 to 6 carbon atoms, benzyl, or are taken together as $(CH_2)_u$, where u is 3–6;

$R^{24}$ is H, $CH_3$ or $-C_6H_5$;

$R^{25}$ is $NR^{27}R^{28}$, $OR^{28}$, $NHCONH_2$, $NHCSNH_2$,

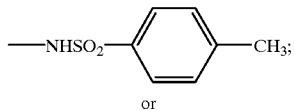

or

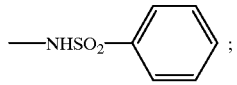

;

$R^{26}$ is hydrogen, alkyl with from 1 to 6 carbon atoms, benzyl, or allyl;

$R^{27}$ and $R^{28}$ are independently hydrogen, alkyl with from 1 to 5 carbon atoms, or phenyl;

$R^{29}$ and $R^{30}$ are independently alkyl of 1–4 carbon atoms or taken together are $-(CH_2)_q-$;

$R^{31}$ is H, alkyl or 1 to 4 carbon atoms, $-CH_2CH=CH_2$ or $-CH_2C_6H_4R^{32}$;

X is a carbon—carbon single bond,

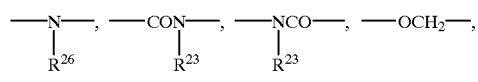

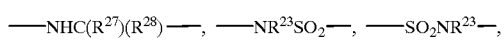

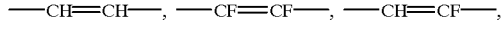

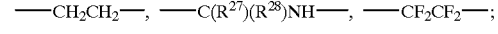

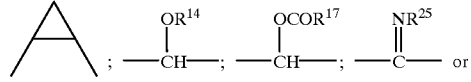

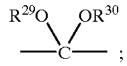

Y is O or S;
Z is O, $NR^{11}$, or S;
m is 1 to 5;
n is 1 to 10;
p is 0 to 3;
q is 2 to 3;
r is 0 to 2;
s is 0 to 5;
t is 0 or 1;
and pharmaceutically acceptable salts of these compounds; provided that:

(1) the $R^1$ group is not in the ortho position;

(2) when $R^1$ is

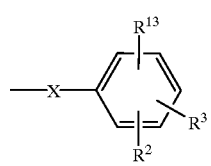

X is a single bond, and $R^{13}$ is $CO_2H$, or

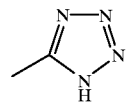

then $R^{13}$ must be in the ortho or meta position; or when $R^1$ and X are as above and $R^{13}$ is $NHSO_2CF_3$ or $NHSO_2CH_3$, $R^{13}$ must be ortho;

(3) when $R^1$ is

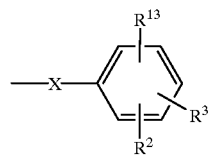

and X is other than a single bond, then $R^{13}$ must be ortho except when $X=NR^{23}CO$ and $R^{13}$ is $NHSO_2CF_3$ or $NHSO_2CH_3$, then $R^{13}$ must be ortho or meta;

(4) when $R^1$ is 4-$CO_2H$ or a salt thereof, $R^6$ cannot be S-alkyl;

(5) when R 1 is 4-$CO_2H$ or a salt thereof, the substituent on the 4-position of the imidazole cannot be $CH_2OH$, $CH_2OCOCH_3$, or $CH_2CO_2H$;

(6) when $R^1$ is

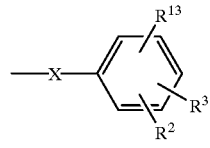

X is $-OCH_2-$, and $R^{13}$ is 2-$CO_2H$, and $R^7$ is H then $R^6$ is not $C_2H_5S$;

(7) when $R^1$ is

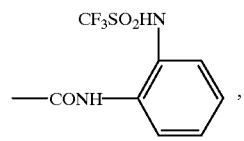

and $R^6$ is n-hexyl then $R^7$ and $R^8$ are not both hydrogen;

(8) when $R^1$ is

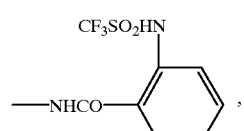

$R^6$ is not methoxybenzyl;

(9) the $R^6$ group is not

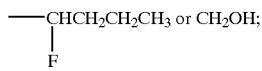
—CHCH$_2$CH$_2$CH$_3$ or CH$_2$OH;
    |
    F

(10) when r=0, $R^1$ is

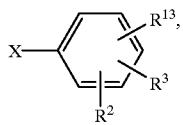

X is

$R^{13}$ is 2-NHSO$_2$CF$_3$, and $R^6$ is n-propyl, then $R^7$ and $R^8$ are not —CO$_2$CH$_3$;

(11) when r=0, $R^1$ is

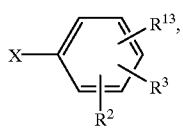

X is

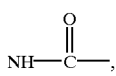

$R^{13}$ is 2-COOH, and $R^6$ is n-propyl, then $R^7$ and $R^8$ are not —CO$_2$CH$_3$;

(12) when r=1,

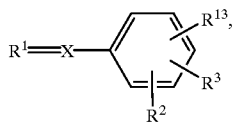

X is a single bond, $R^7$ is Cl, and $R^8$ is —CHO, then $R^{13}$ is not 3-(tetrazol-5-yl);

(13) when r=1,

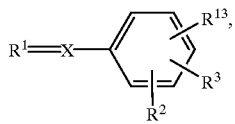

X is a single bond, $R^7$ is Cl, and $R^8$ is —CHO, then $R^{13}$ is not 4-(tetrazol-5-yl).

A preferred embodiment of the invention is the method as recited above, wherein the angiotensin II receptor antagonist is losartan or EXP-3174 or a pharmaceutically acceptable salt thereof. The most preferred embodiment is the method, as recited above, wherein the symptomatic heart failure patient is age 65 or older.

EXAMPLE 1

ELITE Study

Patients and methods

The ELITE study was a prospective double-blind, randomized, parallel, captopril-controlled clinical trial conducted at 125 centers in the United States, Europe and South America. The study was approved by institutional review boards at each site; all patients gave written informed consent. An independent Data and Safety Monitoring Committee monitored the progress of the study. See Pitt B, Chang P, Timmermans P. Angiotensin II receptor antagonists in heart failure: Rationale and design of the Evaluation of Losartan in the Elderly (ELITE) Trial. Cardiovascular Drugs and Therapy 1995; 9: 693–700.

Patient Population

Patients were 65 years or older (two thirds 70 years or older) with symptomatic heart failure (New York Heart Association Class II-IV), decreased left ventricular ejection fraction of 40 percent or less, and had no history of prior ACE inhibitor therapy. A detailed description of enrollment and exclusion criteria and study design has been presented previously. See Pitt B, Chang P, Timmermans P. Angiotensin II receptor antagonists in heart failure: Rationale and design of the Evaluation of Losartan in the Elderly (ELITE) Trial. Cardiovascular Drugs and Therapy 1995; 9: 693–700.

Randomization and Study Therapy

Following a two-week placebo run-in, patients were randomized to 48 weeks of active therapy, either to captopril 6.25 mg titrated to 12.5 mg, 25 mg and then 50 mg three times daily (plus placebo for losartan) or to losartan 12.5 mg, titrated to 25 mg and then 50 mg once daily (plus placebo for captopril). Titration generally occurred at 7-day intervals as tolerated. Treatment with all other concomitant cardiovascular therapies was permitted with the exception of open-label ACE inhibitors. Randomized patients were stratified by age (less than 70 and 70 years or greater).

Evaluation of Patients

Clinical assessments were performed weekly during titration and at three-month intervals thereafter. Laboratory evaluations were performed at weeks three, six, and twelve, and at three month intervals thereafter.

Study Endpoints

The primary endpoint of the study was a safety measure of the development of renal dysfunction, defined as an increase in serum creatinine $\geq 0.3$ mg/dL from baseline that was confirmed by a repeat measurement in 5 to 14 days of the first determination, during continued treatment. All-cause mortality and heart failure hospitalizations were each prespecified endpoints, and the composite of death and/or heart failure hospitalizations was added as the secondary endpoint by protocol amendment based on data from two placebo-controlled 12 week exercise studies (of approximately 350 patients each), demonstrating a beneficial effect on this endpoint. (See Example 2) Hypotension-related symptoms, clinically important serum potassium increases ($\geq 0.5$ mEq/L), and cough, all originally secondary endpoints, were moved to tertiary endpoints. All deaths (including cause of death) and hospitalizations were adjudicated by an independent Clinical Endpoint Adjudication Committee, blinded to study treatment (see panel for mortality classification). Other prospectively-defined measures included myocardial infarction/hospitalization for unstable angina, worsening of heart failure, New York Heart Association functional classification, discontinuation from the study due to study drug intolerance, changes in neurohormonal profile.

Panel: Mortality Classification

Sudden Cardiac Death: Death occurring without warning or within 1 hour of symptoms Death due to Progressive Heart Failure: Death preceded by worsening signs and/or symptoms of heart failure, including cardiogenic shock Fatal Myocardial Infarction: Death associated with autopsy-verified myocardial infarction or death within 28 days of a hospital-verified acute myocardial infarction provided no other cardiac or non-cardiac cause of death is found Death due to Other Cardiac Causes: Death due to other cardiac causes, such as arrhythmia Death due to Other Vascular Causes: Death due to vascular events such as stroke, pulmonary embolus, ruptured aneurysm, etc.

Death due to non-cardiovascular causes: Death not due to any cardiac or vascular events Statistical Methods The power and sample-size estimates for this study have been described. See Pitt B, Chang P, Timmermans P. Angiotensin II receptor antagonists in heart failure: Rationale and design of the Evaluation of Losartan in the Elderly (ELITE) Trial. Cardiovascular Drugs and Therapy 1995; 9: 693–700. Analysis of renal dysfunction (increases in serum creatininie) was based upon a modified intent-to-treat population; i.e., all patients were analyzed according to their randomization group, and an endpoint was declared only if initial and confirmatory elevations occurred while on double-blind therapy. Patients who discontinued from the study without meeting this endpoint were censored in the time-to-event analysis at the time of study discontinuation.

Analyses of deaths and heart failure hospitalizations (adjudicated endpoints) were based on an intent-to-treat population; all patients discontinued prematurely were followed through the specified 48-week period of the study. Patients not meeting the endpoint were censored in the time-to-event analysis either at the time of study completion (for patients who completed) or at the end of the 48-week follow-up period (for patients who discontinued).

For all time-to-event data, survival analyses were based upon the log-rank test. The effect of treatment group in the model was tested controlling for the stratification factor (age category [less than 70 or 70 years and older]). The time to first event was used for each endpoint. Risk reductions were based upon Mantel-Haenszel adjusted (for age catagory) relative risk estimates.

The primary endpoint was tested at the 5% level of significance. No multiplicity adjustments were made for the test of the secondary endpoint or for other tests of interest; unadjusted p-values are presented.

Over approximately a two-year recruitment period, 722 patients enrolled, 352 were randomized to losartan and 370 to captopril (FIG. 1). The two treatment groups were similar with respect to all baseline characteristics (Table 1). Concomitant therapies during the study were similar between the two treatment groups; diuretics were used in over 70 percent of patients, digitalis in over 55% of patients and non-ACE inhibitor vasodilatory drugs (including hydralazine and nitrates) in over 50 percent of patients in both treatment groups. Three hundred patients (85 percent) were titrated to the target dose of losartan 50 mg once daily, and 321 patients (84 percent) in the captopril group were titrated to the target dose of 50 mg three times a day. Seventy-five percent of losartan-treated patients remained on the targeted dose of 50 mg daily (mean daily dose 42.6 mg per day), and 71 percent of captopril patients remained on the targeted dose of 50 mg three times a day (mean daily dose 122.7 mg per day).

TABLE 1

Baseline Clinical Characteristics and Drug Therapy, According to Treatment Group

| CHARACTERISTIC | LOSARTAN (n = 352) | | CAPTOPRIL (n = 370) | |
|---|---|---|---|---|
| | number (percent) of patients | | | |
| Sex | | | | |
| Male | 234 | (66.5) | 248 | (67.0) |
| Female | 118 | (33.5) | 122 | (33.0) |
| Age (years) | | | | |
| <70 | 95 | (27.0) | 119 | (32.2) |
| ≧70 | 257 | (73.0) | 251 | (67.8) |
| Mean (S.D.) | 74 | (5.8) | 73 | (6.1) |
| Race | | | | |
| Caucasian | 320 | (90.9) | 326 | (88.1) |
| Black | 16 | (4.6) | 18 | (4.9) |
| Other | 16 | (4.6) | 26 | (7.0) |
| Etiology of Heart Failure[†] | | | | |
| Ischemic Heart Disease | 242 | (68.8) | 250 | (67.6) |
| Non-Ischemic Heart Disease | 110 | (31.3) | 120 | (32.4) |
| NYHA Functional Class[††] | | | | |
| II | 231 | (65.6) | 237 | (64.1) |
| III | 116 | (33.0) | 126 | (34.1) |
| IV | 5 | (1.4) | 7 | (1.9) |
| Drug Therapy | | | | |
| Diuretics | 260 | (73.9) | 275 | (74.3) |
| Digitalis | 199 | (56.5) | 209 | (56.5) |
| Hydralazine | 12 | (3.4) | 12 | (3.2) |
| Nitrates | 180 | (51.1) | 191 | (51.6) |
| Calcium Channel Blockers | 123 | (34.9) | 121 | (32.7) |
| Potassium Supplement | 91 | (25.9) | 89 | (24.1) |
| Anticoagulants | 60 | (17.0) | 69 | (18.6) |
| Beta-Blockers | 55 | (15.6) | 63 | (17.0) |
| Antiarrhythmics | 37 | (10.5) | 39 | (10.5) |
| Secondary Diagnoses[†] | | | | |
| Myocardial Infarction | 184 | (52.3) | 177 | (47.8) |
| Hypertension | 201 | (57.1) | 212 | (57.3) |
| Atrial Fibrillation | 86 | (24.4) | 82 | (22.2) |
| Diabetes mellitus | 94 | (26.7) | 89 | (24.1) |
| Renal Insufficiency | 21 | (6.0) | 26 | (7.0) |
| Stroke | 32 | (9.1) | 37 | (10.0) |
| Current smoker (cigarettes) | 39 | (11.1) | 45 | (12.2) |
| | mean (S.D.) | | | |
| Ejection Fraction (%) | 31 | (7.2) | 30 | (7.6) |
| Serum Creatinine (mg/dl)[†††] | 1.2 | (0.4) | 1.2 | (0.4) |
| Serum Potassium (mEq/L)[†††] | 4.3 | (0.4) | 4.3 | (0.5) |
| Heart Rate (beats per minute) | 73 | (11.7) | 74 | (10.4) |
| Blood Pressure | | | | |
| Systolic (mmHg) | 137 | (17.6) | 137 | (19.1) |
| Diastolic (mmHg) | 79 | (9.4) | 79 | (10.6) |
| Weight (kg) | 76 | (33.1) | 74 | (33.8) |

Key to Table 1:
[†]Based on patient history.
[††]NYHA denotes New York Heart Association.
[†††]To convert to micromoles per liter, multiply by 88.4; mEq/L is the equivalent of millimoles per liter.

Renal Dysfunction

There was no significant difference between losartan and captopril in terms of persistent increases (i.e., confirmed by a repeat measurement during continued treatment) in serum creatinine ≧0.3 mg/dL from baseline (10.5 percent versus 10.5 percent, p=0.629; Table 2). Single rises of serum creatinine ≧0.3 mg/dL were documented in 92 losartan-treated patients (26.1 percent) and 110 captopril-treated patients (29.7 percent), with a trend towards fewer events occuring in losartan-treated patients (14 percent risk reduction, 95 percent confidence intervals −0.09 to 0.32; p=0.060). Of these patients with single rises of serum creatinine ≧0.3 mg/dL, 68 percent had confirmation measurements performed while on active therapy per protocol; 55 percent of the patients who had these confirmation measurements met the endpoint.

Death and/or Heart Failure Hospitalizations

Figure 2:
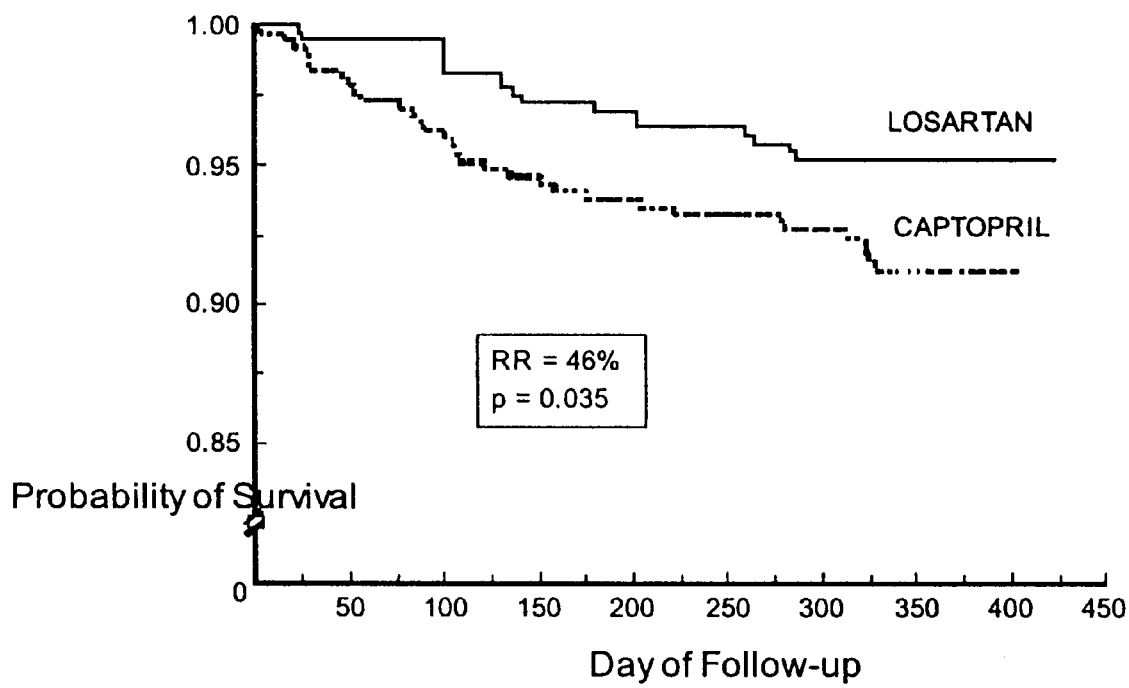
FIG. 2. Kaplan-Meier Survival Curves among Patients with Chronic Heart Failure in the Losartan and Captopril Groups.
(Patients in the losartan group had a 46 percent lower risk of death (RR=risk reduction) than patients in the captopril group (P=0.035). Patients were followed for 48 weeks.)
Figure 3:
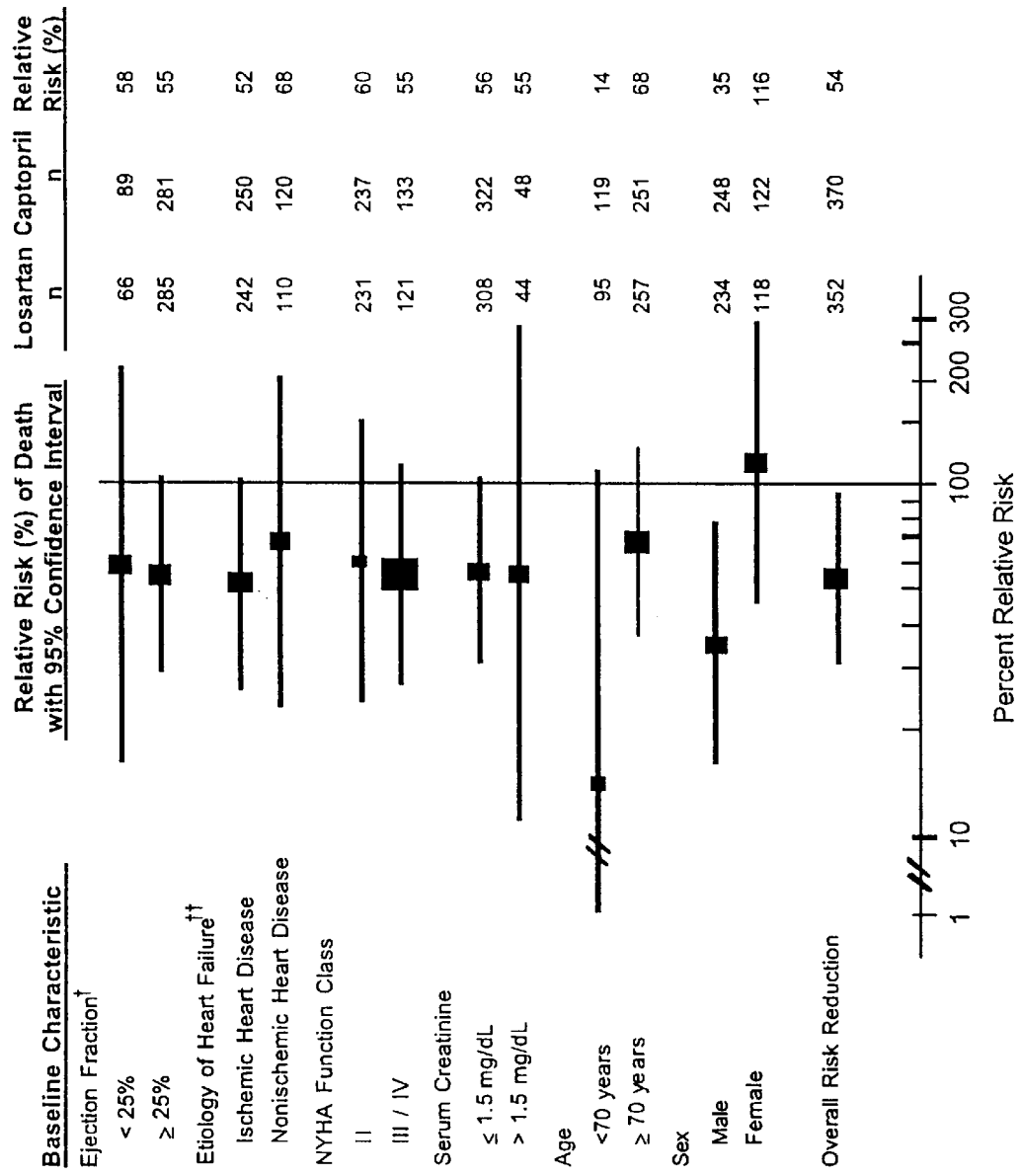
FIG. 3. Effect of Losartan on Death in Various Subgroups.
(⁻ One losartan-treated patient did not have EF measured; and⁼ Based on patient history. For each subgroup, the percentage of risk reduction (RR) with losartan is plotted (solid squares). Horizontal lines represent 95 percent confidence intervals. The size of each square is proportional to the percentage of events in the subgroup. The light square at the bottom of the panel represents the overall result for death. The bold vertical line corresponds to a finding of no effect. The RRs in individual subgroups are generally consistent with the overall RR, except for females. Interaction tests for the effect of losartan on mortality in gender was significant at the 10 percent level (p=0.053). Tests for interaction in the other subgroups were not significant. NYHA denotes New York Heart Association.)

Follow-up data on death and hospitalizations were complete except for one losartan-treated patient who was discontinued after one dose of study medication. During the course of the study, death and/or heart failure hospitalizations occurred in 33 of 352 losartan-treated patients (9.4 percent) compared to 49 of 370 captopril-treated patients (13.2 percent) (p=0.075). This decrease in death and/or heart failure hospitalizations observed with losartan versus captopril was entirely due to a 46 percent decrease in total mortality (17 versus 32 patients [p=0.035]; Table 3). The cumulative survival curves (intent-to-treat) separated early and remained so throughout the 48-week study period (FIG. 2). The observed decrease in total mortality was primarily due to a reduction in sudden cardiac death (five versus 14 patients, p=0.043); only one patient died of progressive heart failure in each treatment group (Table 3). Fatal myocardial infarction occurred in one losartan-treated patient versus four in the captopril arm. The effect of losartan versus captopril on mortality was generally a consistent observation across the different subgroups (FIG. 3), except in a subpopulation of female patients (9 of 118 losartan-treated versus 8 of 122 captopril-treated female patients died).

Fewer losartan-treated patients were hospitalized overall for any reason during the 48-week study observation period than captopril-treated patients (86 [24.4 percent] versus 119 [32.2 percent]; p=0.018). The incidence of heart failure hospitalizations however was not different between treatment groups (both 5.7 percent) (Table 3).

Functional Status and Norepinephrine Levels

Figure 4:
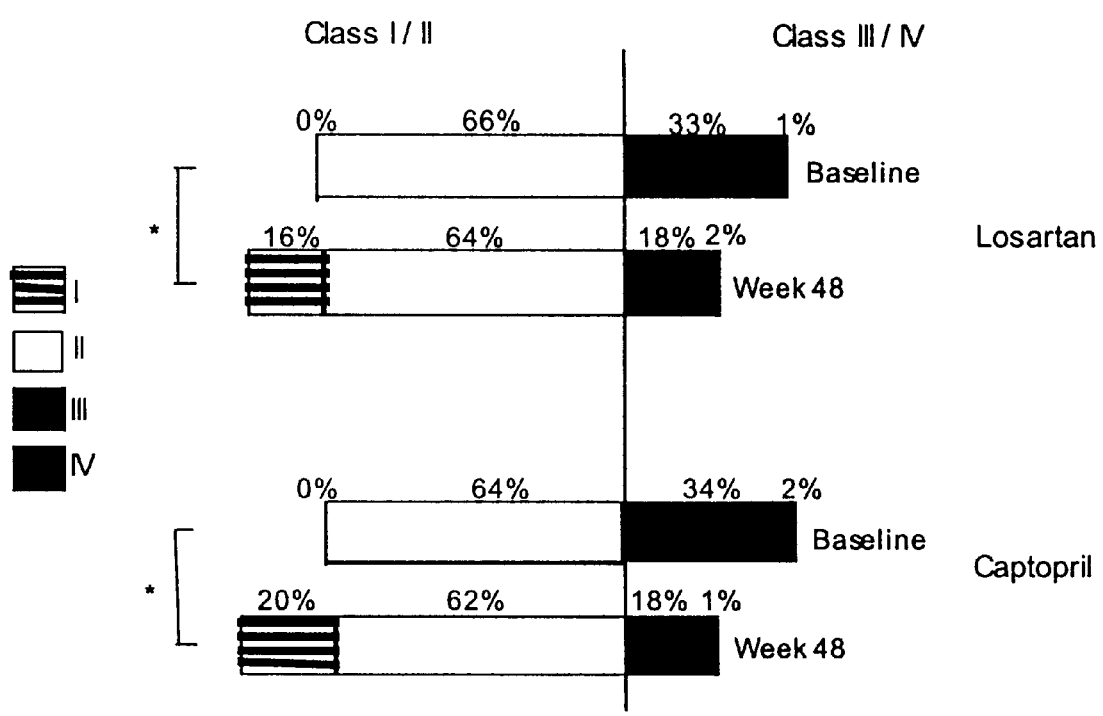
FIG. 4. Changes in New York Heart Association Functional Class. (*P≦0.001. Percent of patients with change in New York Heart Association (NYHA) Functional Class at week 48 versus Baseline.)

New York Heart Association functional class improved similarly with losartan and captopril treatment (p≦0.001 versus baseline for each treatment group); 80 percent of losartan-treated patients and 82 percent of captopril-treated patients were classified as New York Heart Association Class I or II at the end of the study versus 66 percent of losartan-treated patients 1nd 64 percent of captopril-treated patients at baseline (FIG. 4). With regard to plasm-a norepinephrine levels, a three percent decrease from a geometric mean baseline of 469 pg/mL was observed at 48 weeks with losartan treatment, as compared to a five percent increase from a geometric mean baseline of. 424 pg/mL with captopril (p=NS between treatment groups).

TABLE 2

Frequency of Increases in Serum Creatinine in All Patients and by Age

| EVENT | AGE CATEGORY[†] | TREATMENT | N | CRUDE EVENT RATE number (percent) of patients | | RISK REDUCTION (95% CI)[††] | P-VALUE[†††] |
|---|---|---|---|---|---|---|---|
| ≧0.3 mg/dl Increase (confirmed within 5–14 Days) | Overall | Losartan | 352 | 37 | (10.5) | 0.02 (−0.51, 0.36) | 0.629 |
| | | Captopril | 370 | 39 | (10.5) | | |
| | <70 years | Losartan | 95 | 8 | (8.4) | 0.00 (−1.44, 0.59) | |
| | | Captopril | 119 | 10 | (8.4) | | |
| | ≧70 years | Losartan | 257 | 29 | (11.3) | 0.02 (−0.59, 0.40) | |
| | | Captopril | 251 | 29 | (11.6) | | |

[†]Treatment comparisons were performed for overall group only.
[††]Risk Reduction is the reduced risk of experiencing the related endpoint on losartan compared to captopril (a negative number denotes an increase in riskl); overall estimates control for age category; CI denotes confidence interval.
[†††]P-value based upon log-rank test (survival analysis) with age category included as a stratification factor in the model.

TABLE 3

Mortality/Heart Failure Hospitalizations and Cause of Death

| | number (percent) of patients | | | | | |
|---|---|---|---|---|---|---|
| VARIABLE | LOSARTAN n = 352 | | CAPTOPRIL n = 370 | | RISK REDUCTION (95% CI)[†] | P-VALUE[††] |
| Death and/or Hospitalization for Heart Failure | 33 | (9.4) | 49 | (13.2) | 0.32 (−0.04, 0.55) | 0.075 |
| Total Mortality Cardiovascular | 17 | (4.8) | 32 | (8.7) | 0.46 (0.05, 0.69) | 0.035 |
| Sudden Death | 5 | (1.4) | 14 | (3.8) | 0.64 (0.03, 0.86) | 0.043 |
| Progressive Heart Failure | 1 | (0.3) | 1 | (0.3) | −0.11 (−20.23, 0.94) | 0.930 |
| Fatal Myocardial | 1 | (0.3) | 4 | (1.1) | 0.76 (−0.83, 0.97) | 0.172 |

TABLE 3-continued

Mortality/Heart Failure Hospitalizations and Cause of Death number (percent) of patients

| VARIABLE | LOSARTAN n = 352 | | CAPTOPRIL n = 370 | | RISK REDUCTION (95% CI)[†] | | P-VALUE[††] |
|---|---|---|---|---|---|---|---|
| Infarction | | | | | | | |
| Other Vascular | 5 | (1.4) | 5 | (1.4) | −0.03 | (−2.63, 0.71) | 0.958 |
| Non-cardiovascular | 5 | (1.4) | 8 | (2.2) | 0.35 | (−0.94, 0.78) | 0.434 |
| Hospitalization for Heart Failure | 20 | (5.7) | 21 | (5.7) | 0.04 | (−0.74, 0.47) | 0.894 |

[†]Risk Reduction is the reduced risk of the related endpoint on losartan compared to captopril (a negative number denotes an increase in risk); estimates control for age category; CI denotes confidence interval.
[††]P-value based upon log-rank test (survival analysis) with age category included as a stratification factor in the model.

ELITE is the first long-term (48 weeks) study to compare the effect of treatment with losartan, an angiotensin II type I receptor antagonist, to an ACE inhibitor (captopril) in patients with symptomatic heart failure and systolic left ventricular dysfunction. Captopril was chosen as the comparative ACE inhibitor in this study because it had been suggested to have less adverse renal effects than longer-acting ACE inhibitors. (See Packer, M., Lee, W. H., Yushak, M., Medina, N.: Comparison of Captopril and Enalapril in patients with severe chronic heart failure. N Engl J Med; 315: 847–853.) The incidence of persistent renal dysfunction, as defined by a persisting increase in serum creatinine of 0.3 mg/dL (the primary endpoint), was not different between losartan- and captopril-treated patients (both 10.5%). The observation overall that both losartan and captopril were relatively well tolerated with regard to renal function was evident, given that less than 2% of patients discontinued for this reason in either group. This is of clinical relevance for treating older patients with heart failure.

The results of this study demonstrate that treatment with losartan resulted in a 46% reduction in all-cause mortality compared to captopril, a drug with demonstrated survival benefit in several studies. (See Pfeffer M A, Braunwald E, Moye L A, et al. on behalf of the SAVE Investigators. Effect of captopril on mortality and morbidity in patients with left ventricular dysfunction after myocardial infarction. Results of the Survival and Ventricular Enlargement Trial. N Engl J Med 1992; 327: 669–677; Fonarow G C, Chelimsky-Fallick C, Warner Stevenson L, et al. Effect of direct vasodilation with hydralazine versus angiotensin-converting enzyme inhibition with captopril on mortality in advanced heart failure: the Hy-C trial. J Am Coll Cardiol 1992; 19: 842–850; and ISIS Collaborative Group OU. ISIS-4: Randomized study of oral isosorbide mononitrate ill over 50,000 patients with suspected acute myocardial infarction. Circulation 1993; 88: 1394.) The cumulative survival benefit of losartan was observed early during the study, persisted throughout the 48-week treatment period, and was consistent among all subgroups except in female patients. It should be noted that the number of female patients enrolled in this study was relatively small; and the mortality benefit could not be demonstrated in this study. The greater drop-out rate in the captopril-treated patients did not account for the beneficial effects of losartan on total mortality; the treatment difference in total mortality was primarily due to those who remained on active therapy.

Figure 5:
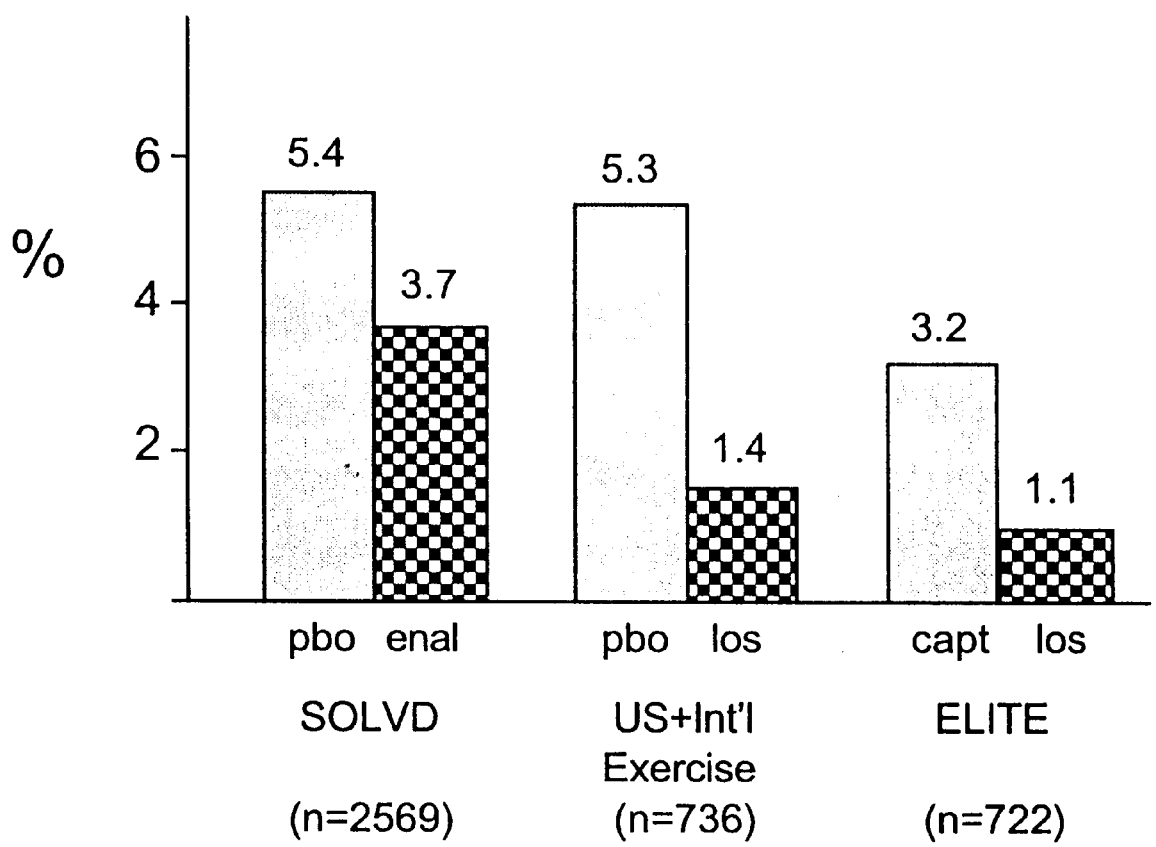
FIG. 5. Comparison of twelve-week mortality data from the SOLVD study, the losartan exercise studies (U.S. and international combined), and the ELITE study.
(pbo=placebo; enal=enalapril; los=losartan; capt=captopril).

An improvement in survival with losartan of similar magnitude has also been observed in two placebo-controlled 12-week exercise studies. See Klinger G, Jaramillo N, Ikram H, et al. Effects of losartan on exercise capacity, morbidity and mortality in patients with symptomatic heart failure. J Am Coll Cardiol 1996 (in press); (Abstract). The three-month control group mortality rates in the exercise studies and the present study were comparable to the placebo and enalapril mortality rates respectively in the Studies of Left Ventricular Dysfunction (SOLVD) trial (FIG. 5). See The SOLVD Investigators. Effect of enalapril on survival in patients with reduced left ventricular ejection fractions and congestive heart failure. N Engl J Med 1991; 325: 293–302. Despite the limitations of cross-study comparisons, treatment with losartan in the exercise studies and the present study was associated with comparably low mortality rates which were less than the observed mortality rates for both placebo and enalapril in SOLVD.

Prior to the use of ACE inhibitors, progressive heart failure accounted for approximately 50% of deaths due to heart failure. See Applefield M M. Chronic congestive heart failure: Where have we been? Where are we heading? Am J Med 1986; 80: 73–77. In patients with mild to moderate heart failure treated with an ACE inhibitor, death due to progressive heart failure has diminished so that sudden cardiac death is currently the predominant mode of death. For example, in the recently discontinued Survival With Oral d-Sotalol (SWORD) trial, in which patients with mild to moderate heart failure or left ventricular dysfunction were randomized to d-Sotalol or placebo on a background of usual therapy including an ACE inhibitor, arrhythmic death accounted for approximately two-thirds of total mortality in the placebo group, while progressive heart failure for only one-sixth. See Waldo A L, Camm A J, deRuyter H, et al. for the SWORD Investigators. Effect of d-sotalol on mortality in patients with left ventricular dysfunction after recent and remote myocardial infarction. Lancet 1996; 349: 7–12. In the present study, sudden cardiac death was also the most prominent cause of death in the captopril-treated patients. Of interest, the observed reduction in mortality on losartan compared to captopril-treated patients in the present study was primarily died due to a reduction in sudden cardiac death (see Table 3). Few patients died due to progressive heart failure or to fatal myocardial infarction in either treatment group, although numerically, fatal myocardial infarction deaths occurred less with losartan.

The mechanism by which losartan reduces sudden cardiac death in comparison to captopril is uncertain. Whether the reduction in sudden cardiac death was due to more complete blockade of angiotensin II effects or an intrinsic antiarrhythmic/antifibrillatory property of losartan remains to be determined. ACE activity may not be completely suppressed by the presently studied captopril dosing regimen (target dose of 50 mg three times daily), which is a regimen considered to have a mortality benefit. See Cohn J N. The management of chronic heart failure. N Engl J Med 1996; 335: 490–499. In addition angiotensin II may also be formed by non-ACE-dependent pathways. (See Miura S, Ideishi M, Sakai T, et al. Angiotensin II formation by an alternative pathway during exercise in humans. J Hypertension 1994; 12: 1177–1181; Urata H, Kinoshita A, Misono KS, Bumpus FM, Husain A. Identification of a highly specific chymase as the major angiotensin II-forming enzyme in the human chymase. J Biol Chem 1990; 265: 22349–22357; Urata H, Strobel F, Ganten D. Widespread tissue distribution of human chymase. J Hypertension 1994; 12: S17–S22; and Aldigier J C, Huang H, Dalmay F, et al. Angiotensin-converting enzyme inhibition does not suppress plasma angiotensin II increase during exercise in humans. J Cardiovasc Pharmacol 1993; 21: 289–295.) It is possible that more complete blockade of angiotensin II effects by losartan may result in more complete suppression of catecholamines at the tissue level. See Brasch H, Sieroslawski L, Dominiak P. Angiotensin II increases norepinephrine release from atria by acting on angiotensin subtype 1 receptors. Hypertension 1993; 22: 699–704. Furthermore, bradykinin, which is known to release norepinephrine, is not elevated with direct angiotensin II blockade compared with ACE inhibitor therapy. (See Minisi A J, Thames M D. Distribution of left ventricular sympathetic afferents demonstrated by reflex responses to transmural myocardial ischemia and to intracoronaly and epicardial bradykinin. Circulation 1993; 87: 240–246; and Timmermans, P, Wong P C, Chiu A T, et al. Angiotensin II receptors and angiotensin II receptor antagonists. Pharmacol Reviews 1993; 45: 205–251.) A small decrease in mean plasma norepinephrine was observed in the present study with losartan compared to captopril. Plasma catecholamine levels may not, however, reflect local cardiac tissue levels, and resting values may not reflect transient increases during stress or ischemia.

In this study, heart failure status appeared to improve to a similar degree in both treatment groups. New York Heart Association functional class improved significantly and to a comparable extent from baseline following long-term treatment with both losartan and captopril (FIG. 4). The rate of hospitalization for heart failure in patients treated with losartan was also similar to that observed in patients treated with captopril. Another similarity was the low incidence of death due to progressive heart failure (less thin one percent for both losartan and captopril-treated patients), suggesting a similar beneficial effect for both treatments. Overall hospitalizations were however less frequent with losartan treatment versus captoril.

In conclusion, in older patients with symptomatic heart failure, losartan was better tolerated compared to captopril, with fewer patients discontinuing therapy due to adverse effects or being hospitalized, but was not different from captopril in causing persistent renal dysfunction defined as a sustained increase in serum creatinine. The effects on progressive heart failure hospitalization and improvement in New York Heart Association functional class were similar in the two treatment groups. There was, however, a decrease in all-cause mortality observed with losartan compared to captopril treatment, mainly due to a reduction in sudden cardiac death. These findings suggest that treatment with losartan may offer important therapeutic benefits compared to an ACE inhibitor, and may have far reaching implications for the treatment of patients with heart failure.

EXAMPLE 2

Exercise Study-Protocols A & B

Protocols A & B were, multicenter, double-blind, randomized, parallel, placebo-controlled studies to investigate the effects of losartan on the exercise capacity and clinical status of patients over the age of 18 with symptomatic heart failure.

Approximately three hundred and fifty (350) patients with symptomatic heart failure (NYHA Functional Class II-IV, at least 50% Class III-IV) and left ventricular ejection fraction $\leq 40\%$ were randomized to receive either losartan or placebo once daily for 12 weeks in each study. Following a minimum 15-day baseline placebo period, during which a minimum of 5 and maximum of 8 sets of baseline exercise tests (treadmill exercise test and 6-minute walk test) were performed, patients were randomized to treatment with losartan or placebo in a 2:1 ratio, respectively. According to the protocol's, patients must not have received an ACE-inhibitor for at least 6 weeks prior to the third baseline exercise test visit. Treatment with an ACE-inhibitor was not allowed at any time during these studies.

This report summarizes the results of the Meta-analysis performed (as proposed in the Data Analysis Plan) on the observed mortality and congestive heart failure (CHF) hospitalization across these two studies. The mortality and CHF hospitalization were not predefined endpoints in the protocols but it was intended that they be analyzed as a part of safety. Thus results from these analyses should not be interpreted as a test of significance as there were no predefined hypotheses corresponding to these safety parameters. However, these results can simply be regarded as a measure of the disparity between the losartan and placebo groups with respect to the observed results across the two studies. Odds ratio's with 95% confidence intervals have been provided for these variables.

Peto-modified Manltel-Haenszel (Fleiss, J. L., Statistical Methods for Rates and Proportions, Wiley, N.Y., 1981.) method was used to carry out the Meta-analysis of death and CHF hospitalization rates in the two 12 week exercise studies. This method assumes homogeneity across the studies and provides ai test for heterogeneity. Results of the Meta-analysis are displayed in Tables 4–6.

A total of three hundred and fifty one (351) patients were enrolled in the protocol A study; 237 patients were randomized to receive losartan and 114 patients were randomized to receive placebo. There were 4 (3.5%) deaths in the placebo group as compared to 4 (1.7%) in the losartan group during the double-blind therapy or as related to serious adverse events (AE) during double-blind. Additionally there were 10 (8.8%) CHF hospitalizations in the placebo group as compared to 10 (4.2%) in the losartan group during the double-blind therapy or as related to serious AE during double-blind. One patient included in the losartan group discontinued due to worsening HF and was hospitalized 2 days after discontinuation from double-blind period.

Table 4 provides the odds ratio for the Death and CHF hospitalization in the protocol A exercise study. The odds of dying in the placebo group are 2.1 times the odds of dying in the losartan group while the odds of CHF hospitalization in the placebo group are 2.2 times the odds of CHF hospitalization in the losartan group. However, since 1.0 is included in both the 95% confidence intervals the possibility that the odds of dying (or CHF hospitalization) in the placebo group is the same as odds of dying (or CHF hospitalization) in the losartan group can not be excluded (see Table 4).

A total of three hundred and eighty five (385) patients were enrolled in the protocol B exercise study; 254 patients were randomized to receive losartan and 131 patients were randomized to receive placebo. There were 9 (6.9%) deaths in the placebo group as compared to 3 (1.2%) in the losartan group during the double-blind therapy or as related to serious AE during double-blind. Additionally there were 7 (5.3%) CHF hospitalizations in the placebo group as compared to 5 (2.0%) in the losartan group during the double-blind therapy or as related to serious AE during double-blind.

Table 5 provides the odds ratio for the Death and CHF hospitalization in the protocol B exercise study. The odds of dying in the placebo group are 5.6 times the odds of dying in the losartan group while the odds of CHF hospitalization in the placebo group are 2.7 times the odds of CHF hospitalization in the losartan group. The 95% confidence interval for odds ratio of death was (1.61, 19.34). This implies that the odds of dying in the placebo group are greater than the odds of dying in the losartan group. However, since 1.0 is included in the 95% confidence interval for odds ratio of CHF hospitalization, the possibility that the odds of CHF hospitalization in the placebo group is same as the odds of CHF hospitalization in the losartan group can not be excluded (see Table 5).

Since the results from protocols A and B are consistent, a safety Meta-analysis as proposed in the Data Analysis Plan has been performed. Homogeneity between the two studies with respect to odds ratio's for death and CHF hospitalization was found.

Table 6 provides the results of the Meta-analysis of the two 12 week exercise studies. The odds of dying in the placebo group are 3.5 times the odds of dying in the losartan group while the odds of CHF hospitalization in the placebo group ale 2.4 times the odds of CHF hospitalization in the losartan group. The 95% confidence intervals for odds ratio's with respect to death and CHF hospitalization are (1.43, 8.77) and (1.19, 4.76), respectively. Thus the odds of dying in the placebo group are significantly greater than the odds of dying in the losartan group. Similarly the odds of CHF hospitalization in the placebo group are significantly greater than the odds of CHF hospitalization in the losartan group.

TABLE 4

CLINICAL EVENTS-PROTOCOL A

| | PBO (N= 131) | Losartan (N = 254) | Odds Ratio | 95% Confidence Intervals Lower | Upper |
|---|---|---|---|---|---|
| Death[b] | 3.5% | 1.7% | 2.1 | 0.56 | 7.96 |
| CHF Hospitalization (during DB) | 8.8% | 4.2%[a] | 2.2 | 0.90 | 5.28 |

[b]during double-blind therapy or was related to SAE during double-blind
[a]one patient discontinued due to worsening HF and was hospitalized 2 days after discontinuation from double-blind.

TABLE 5

CLINICAL EVENTS-PROTOCOL B

| | PBO (N= 131) | Losartan (N = 254) | Odds Ratio | 95% Confidence Intervals Lower | Upper |
|---|---|---|---|---|---|
| Death[b] | 6.9% | 1.2% | 5.6* | 1.61 | 19.34 |
| CHF Hospitalization (during DB) | 5.3% | 2.0% | 2.7 | 0.89 | 8.39 |

[b]during double-blind therapy or was related to Serious AE during double-blind
*odds are greater for placebo group as compared to losartan group

TABLE 6

Meta-Analysis@
CLINICAL EVENTS-PROTOCOLS A & B

| | PBO (N = 245) | Losartan (N = 491) | Odds Ratio | 95% Confidence Intervals Lower | Upper |
|---|---|---|---|---|---|
| Death[b] | 5.3% | 1.4% | 3.5* | 1.43 | 8.77 |
| CHF Hospitalization (during double-blind | 6.9% | 3.1%[a] | 2.4* | 1.19 | 4.76 |

@Peto-modified Mantel-Haenszel method
[b]during double-blind therapy or was related to Serious AE during double-blind
[a]one patient discontinued due to worsening HF and was hospitalized 2 days after discontinuation from double-blind.
*odds are greater for placebo group as compared to losartan group

What is claimed is:

1. A method for reducing mortality rates by administering to chronic symptomatic heart failure patients a therapeutically effective amount of an angiotensin II receptor antagonist.

2. A method for reducing mortality rates by administering to chronic symptomatic heart failure patients a therapeutically effective amount of an angiotensin II receptor antagonist selected from the group consisting of: candesartan cilexetil, eprosartan, irbesartan, losartan, tasosartan, telmisartan, valsartan, 3-(2'-(tetrazol-5-yl)-1,1'-biphen-4-yl)methyl-5,7-dimethyl-2-ethyl-3H-imidazo[4,5-b]pyridine, 4'[2-ethyl-4-methyl-6-(5,6,7,8-tetrahydroimidazo[1,2-a]pyridin-2-yl]-benzimidazol-1-yl]-methyl]-1,1'-biphenyl]-2-carboxylic acid, 2-butyl-6-(1-methoxy-1-methylethyl)-2-[2'-(1H-tetrazol-5-yl)biphenyl-4-ylmethyl]guinazolin-4(3H)-one, 3-[(2'-carboxybiphenyl-4-yl)methyl]-2-cyclopropyl-7-methyl-3H-imidazo[4,5-b]pyridine, 2-butyl-4-chloro-1-[(2'-tetrazol-5-yl)biphenyl-4-yl)methyl] imidazole-carboxylic acid, 2-butyl-4-chloro-1-[[2'-(1H-tetrazol-5-yl)[1,1'-biphenyl]-4-yl]methyl]-1H-imidazole-5-carboxylic acid-1-(ethoxycarbonyl-oxy)ethyl ester potassium salt, dipotassium 2-butyl-4-(methylthio)-1-[[2-[[[(propylamino)carbonyl]amino]-sulfonyl](1,1'-biphenyl)-4-yl]methyl]-1H-imidazole-5-carboxylate, methyl-2-[[4-butyl-2-methyl-6-oxo-5-[[2'-(1H-tetrazol-5-yl)-[1,1'-biphenyl]-4-yl]methyl]-1-(6H)-pyrimidinyl]methyl]-3-thiophencarboxylate, 5-[(3,5-dibutyl-1H-1,2,4-triazol-1-yl)methyl]-2-[2-(1H-tetrazol-5-ylphenyl)]pyridine, 6-butyl-2-(2-phenylethyl)-5-[[2'-(1H-tetrazol-5-yl)[1,1'-biphenyl]-4-methyl]pyrimidin-4-(3H)-one D,L lysine salt, 5-methyl-7-n-propyl-8-[[2'-(1H-tetrazol-5-yl)biphenyl-4-yl]methyl]-[1,2,4]-triazolo[1,5-c]pyrimidin-2(3H)-one, 2,7-diethyl-5-[[2'-(5-tetrazolyl)biphenyl-4-yl]methyl]-5H-pyrazolo[1,5-b][1,2,4]triazole potassium salt, 2-[2-butyl-4,5-dihydro-4-oxo-3-

[2'-(1H-tetrazol-5-yl)-4-biphenylmethyl]-3 H-imidazol[4,5-c]pyridine-5-ylmethyl]-benzoic acid, ethyl ester, potassium salt, 3-methoxy-2,6-dimethyl-4-[[2'-(1H-tetrazol-5-yl)-1,1'-biphenyl-4-yl]methoxy]pyridine, 2-ethoxy-1-[[2'-(5-oxo-2,5-dihydro-1,2,4-oxadiazol-3-yl)biphenyl-4-yl]methyl]-1H-benzimidazole-7-carboxylic acid, 1-[N-(2'-(1H-tetrazol-5-yl)biphenyl-4-yl-methyl)-N-valerolylaminomethyl)cyclopentane-1-carboxylic acid, 7-methyl-2n-propyl-3-[[2'1H-tetrazol-5-yl)biphenyl-4-yl]methyl]-3H-imidazo[4,5-6]pyridine, 2-[5-[(2-ethyl-5,7-dimethyl-3H-imidazo[4,5-b]pyridine-3-yl)methyl]-2-quinolinyl]sodium benzoate, 2-butyl-6-chloro-4-hydroxymethyl-5-methyl-3-[[2'-(1H-tetrazol-5-yl)biphenyl-4-yl]methyl]pyridine, 2-[[[2-butyl-1-[(4-carboxyphenyl)methyl]-1H-imidazol-5-yl]methyl]amino]benzoic acid tetrazol-5-yl)biphenyl-4-yl]methyl] pyrimidin-6-one, 4(S)-[4-(carboxymethyl)phenoxy]-N-[2(R)-[4-(2-sulfobenzamido)imidazol-1-yl]octanoyl]-L-proline, 1-(2,6-dimethylphenyl)-4-butyl-1,3-dihydro-3-[[6-[2-(1H-tetrazol-5-yl)phenyl]-3-pyridinyl]methyl]-2H-imidazol-2-one, 5,8-ethano-5,8-dimethyl-2-n-propyl-5,6,7,8-tetrahydro-1-[[2'-(1H-tetrazol-5-yl)biphenyl-4-yl]methyl]-1H,4H-1,3,4a, 8a-tetrazacyclopentanaphthalene 9 one, 4-[1-[2'-(1,2,3,4-tetrazol-5-yl)biphen-4-yl)methylamino]-5,6,7,8-tetrahydro-2-trifylquinazoline, 2-(2-chlorobenzoyl)imino-5-ethyl-3-[2'-(1H-tetrazole-5-yl)biphenyl-4-yl)methyl-1,3,4-thiadiazoline, 2-[5-ethyl-3-[2-(1H-tetrazole-5-yl)biphenyl-4-yl]methyl-1,3,4-thiazoline-2-ylidene]aminocarbonyl-1-cyclopentencarboxylic acid dipotassium salt, and 2-butyl-4-[N-methyl-N-(3-methylcrotonoyl)amino]-1-[[2'-(1H-tetrazol-5-yl)biphenyl-4-yl]methyl]-1H-imidazole-5-carboxylic acid 1-ethoxycarbonyloxyethyl ester.

3. The method as recited in claim 2, wherein the angiotensin II receptor antagonist is selected from the group consisting of: candesartan cilexetil, eprosartan, irbesartan, losartan, tasosartan, telmisartan, valsartan, and 3-(2'-(tetrazol-5-yl)-1,1'-biphen-4-yl)methyl-5,7-dimethyl-2-ethyl-3H-imidazo[4,5-b]pyridine.

4. A method for reducing mortality rates by administering to chronic symptomatic heart failure patients at therapeutically effective amount of an angiotensin II receptor antagonist of formula I

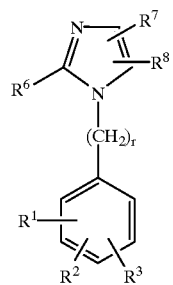

I wherein:

$R^1$ is:

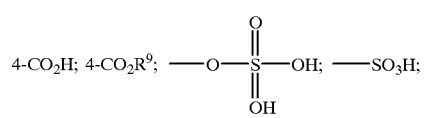

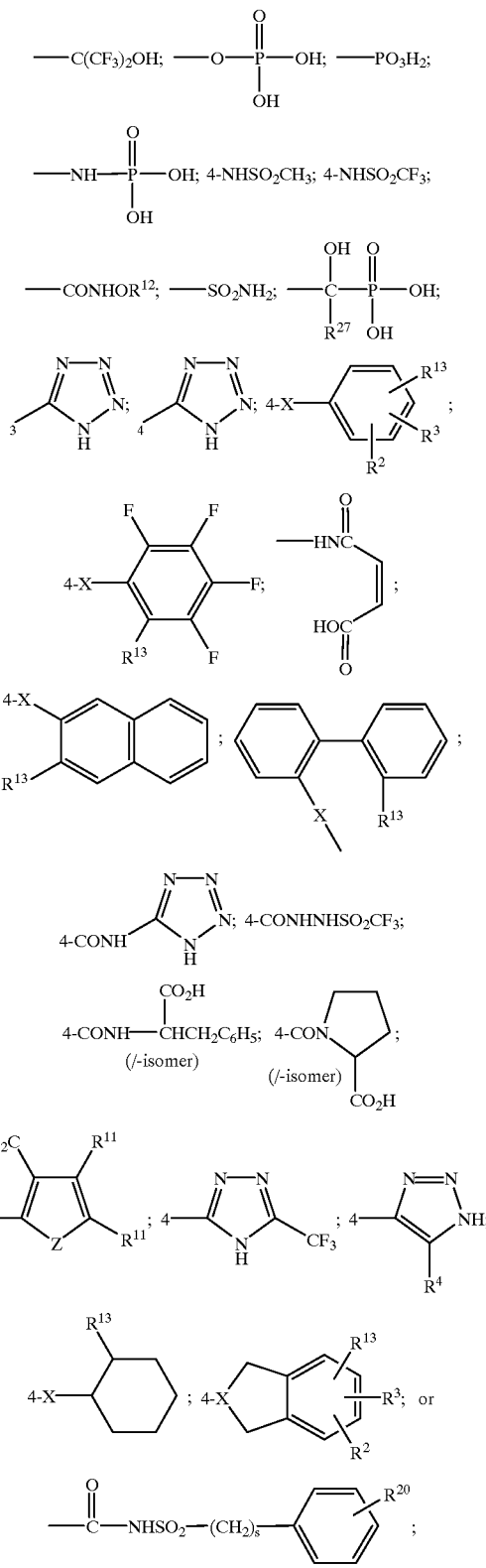

$R^2$ is H; Cl; Br; I; F; $NO_2$; CN; alkyl of 1 to 4 carbon atoms; acyloxy of 1 to 4 carbon atoms; alkoxy of 1 to 4 carbon atoms; $CO_2H$; $CO_2R^9$; $HNSO_2CH_3$; $NHSO_2CF_3$; $CONHOR^{12}$; $SO_2NH_2$;

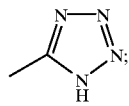

aryl; or furyl;

$R^3$ is H; Cl, Br, I or F; alkyl of 1 to 4 carbon atoms or alkoxy of 1 to 4 carbon atoms;

$R^4$ is CN, $NO_2$ or $CO_2R^{11}$;

$R^5$ is H, alkyl of 1 to 6 carbon atoms, cycloalkyl of 3 to 6 carbon atoms alkenyl or alkynyl of 2 to 4 carbon atoms;

$R^6$ is alkyl of 2 to 10 carbon atoms, alkenyl or alkynyl of 3 to 10 carbon atoms or the same groups substituted with F or $CO_2R^{14}$; cycloalkyl of 3 to 8 carbon atoms, cycloalkylalkyl, of 4 to 10 carbon atoms; cycloalkylalkenyl or cycloalkylalkynyl 5 to 10 carbon atoms; $(CH_2)_sZ(CH_2)_mR^5$ optionally substituted with F or $CO_2R^{14}$; benzyl substituted on the phenyl ring with 1 or 2 halogens, alkoxy of 1 to 4 carbon atoms, alkyl of 1 to 4 carbon atoms or nitro;

$R^7$ is H, F, Cl, Br, I, $NO_2$, $C_vF_{2v+1}$ where v=1–6, $C_6F_5$; CN;

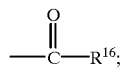

straight or branched alkyl of 1 to 6 carbon atoms; phenyl or phenylalkyl, where alkyl is 1 to 3 carbon atoms; or substituted phenyl or substituted phenylalkyl, where alkyl is 1 to 3 carbon atoms, substituted with one or two substituents selected from alkyl of 1 to 4 carbon atoms, F, Cl, Br, OH, $OCH_3$, $CF_3$, or COOR, where R is H, alkyl of 1 to 4 carbon atoms, or phenyl;

$R^8$ is H, CN, alkyl of 1 to 10 carbon atoms, alkenyl of 3 to 10 carbon atoms, or the same groups substituted with F; phenylalkenyl wherein the aliphatic portion is 2 to 6 carbon atoms; —$(CH_2)_m$-imidazol-1-yl; —$(CH_2)_m$-1,2,3-triazolyl optionally substituted with one or two group selected from $CO_2CH_3$ or alkyl of 1 to 4 carbon atoms; —$(CH_2)_s$ tetrazolyl;

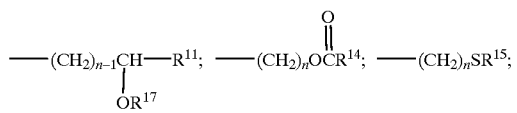

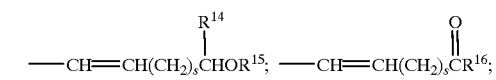

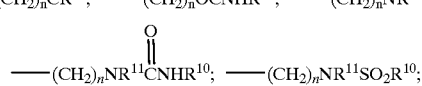

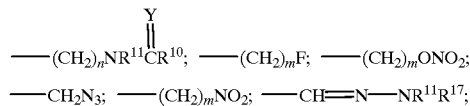

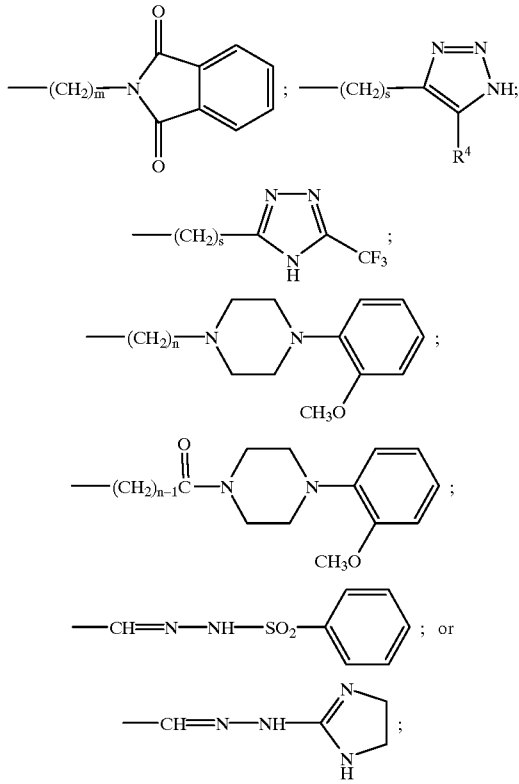

$R^9$ is:

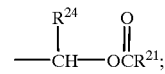

$R^{10}$ is alkyl of 1 to 6 carbon atoms or perfluoroalkyl of 1 to 6 carbon atoms, 1-adamantyl, 1-naphthyl, 1-(1-naphthyl)ethyl, or $(CH_2)_pC_6H_5$;

$R^{11}$ is H, alkyl of 1 to 6 carbon atoms, cycloalkyl of 3 to 6 carbon atoms, phenyl or benzyl;

$R^{12}$ is H, methyl or benzyl;

$R^{13}$ is

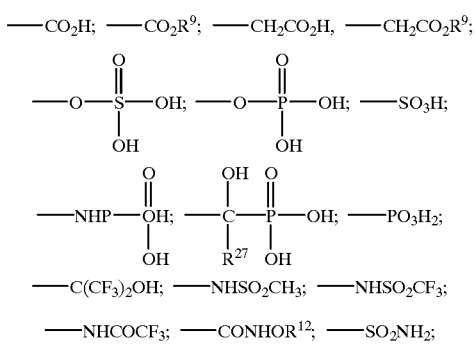

-continued

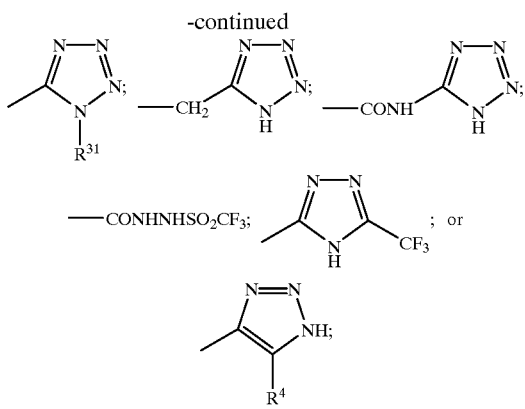

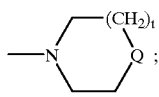

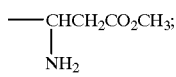

- $R^{14}$ is H, alkyl or perfluoroalkyl of 1 to 8 carbon atoms, cycloalkyl of 3 to 6 carbon atoms, phenyl or benzyl;
- $R^{15}$ is H, alkyl of 1 to 6 carbon atoms, cycloalkyl of 3 to 6 carbon atoms, phenyl, benzyl, acyl of 1 to 4 carbon atoms, or phenacyl;
- $R^{16}$ is H, alkyl of 1 to 6 carbon atoms, cycloalkyl of 3 to 6 carbon atoms, $(CH_2)_pC_6H_5$, $OR^{17}$, or $NR^{18}R^{19}$;
- $R^{17}$ is H, alkyl of 1 to 6 carbon atoms, cycloalkyl of 3 to 6 carbon atoms, phenyl or benzyl;
- $R^{18}$ and $R^{19}$ independently are H, alkyl of 1 to 4 carbon atoms, phenyl, benzyl, (x-methylbenzyl, or taken together with the nitrogen form a ring of the formula

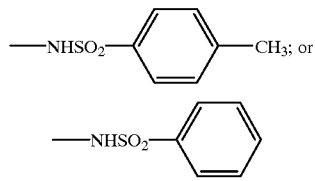

- Q is $NR^{20}$, O or $CH_2$;
- $R^{20}$ is H, alkyl of 1–4 carbon atoms, or phenyl;
- $R^{21}$ is alkyl of 1 to 6 carbon atoms, $-NR^{22}R^{23}$, or $$-\underset{NH_2}{\underset{|}{C}}HCH_2CO_2CH_3;$$

- $R^{22}$ and $R^{23}$ independently are H, alkyl of 1 to 6 carbon atoms, benzyl, or are taken together as $(CH_2)_u$, where u is 3–6;
- $R^{24}$ is H, $CH_3$ or $-C_6H_5$;
- $R^{25}$ is $NR^{27}R^{28}$, $OR^{28}$, $NHCONH_2$, $NHCSNH_2$,

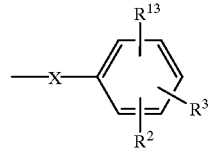

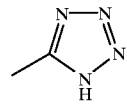

- $R^{26}$ is hydrogen, alkyl with from 1 to 6 carbon atoms, benzyl, or allyl;
- $R^{27}$ and $R^{28}$ are independently hydrogen, alkyl with from 1 to 5 carbon atoms, or phenyl;
- $R^{29}$ and $R^{30}$ are independently alkyl of 1–4 carbon atoms or taken together are $-(CH_2)_q-$;

- $R^{31}$ is H, alkyl or 1 to 4 carbon atoms, $-CH_2CH=CH_2$ or $-CH_2C_6H_4R^{32}$;
- X is a carbon—carbon single bond,

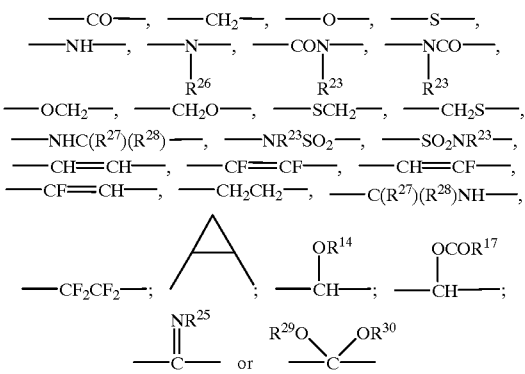

- Y is O or S;
- Z is O, $NR^{11}$, or S;
- m is 1 to 5;
- n is 1 to 10;
- p is 0 to 3;
- q is 2 to 3;
- r is 0 to 2;
- s is 0 to 5;
- t is 0 or 1;

or pharmaceutically acceptable salts of these compounds; provided that:

(1) the $R^1$ group is not in the ortho position;
(2) when $R^1$ is

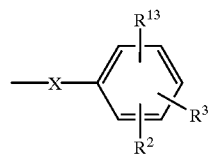

X is a single bond, and $R^{13}$ is $CO_2H$, or

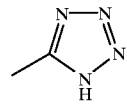

then $R^{13}$ must be in the ortho or meta position; or when $R^1$ and X are as above and $R^{13}$ is $NHSO_2CF_3$ or $NHSO_2CH_3$, $R^{13}$ must be ortho;

(3) when $R^1$ is

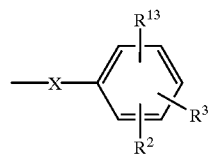

and X is other than a single bond, then $R^{13}$ must be ortho except when $X=NR^{23}CO$ and $R^{13}$ is $NHSO_2CF_3$ or $NHSO_2CH_3$, then $R^{13}$ must be ortho or meta;

(4) when $R^1$ is 4-$CO_2H$ or a salt thereof, $R^6$ cannot be S-alkyl;

(5) when $R^1$ is 4-$CO_2H$ or a salt thereof, the substituent on the 4-position of the imidazole cannot be $CH_2OH$, $CH_2OCOCH_3$, or $CH_2CO_2H$;

(6) when $R^1$ is

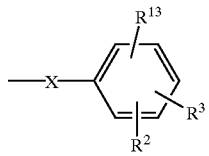

X is —$OCH_2$—, and $R^{13}$ is 2-$CO_2H$, and $R^7$ is H then $R^6$ is not $C_2H_5S$;

(7) when $R^1$ is

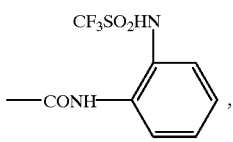

and $R^6$ is n-hexyl then $R^7$ and $R^8$ are not both hydrogen;

(8) when $R^1$ is

$R^6$ is not methoxybenzyl;

(9) the $R^6$ group is not

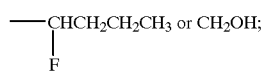

(10) when r=0, $R^1$ is

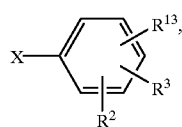

X is

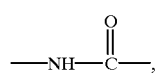

$R^{13}$ is 2-$NHSO_2CF_3$, and $R^6$ is n-propyl, then $R^7$ and $R^8$ are not —$CO_2CH_3$;

(11) when r=0, $R^1$ is

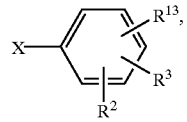

X is

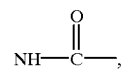

$R^{13}$ is 2-COOH, and $R^6$ is n-propyl, then $R^7$ and $R^8$ are not —$CO_2CH_3$;

(12) when r=1,

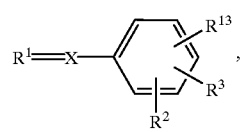

X is a single bond, $R^7$ is Cl, and $R^8$ is —CHO, then $R^{13}$ is not 3-(tetrazol-5-yl);

(13) when r=1,

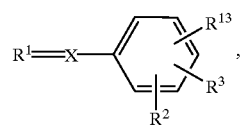

X is a single bond, $R^7$ is Cl, and $R^8$ is —CHO, then $R^{13}$ is not 4-(tetrazol-5-yl).

5. The method as recited in claim 4, wherein the angiotensin II receptor antagonist is of formula I:

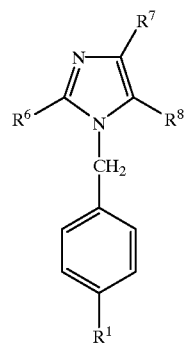

wherein:
$R^1$ is —$CO_2H$; —$NHSO_2CF_3$;

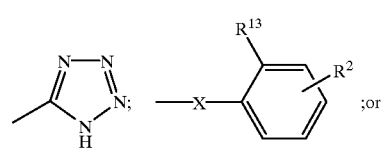

-continued

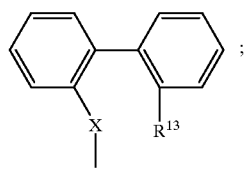

$R^6$ is alkyl of 3 to 10 carbon atoms, alkenyl of 3 to 10 carbon atoms, alkynyl of 3 to 10 carbon atoms, cycloalkyl of 3 to 8 carbon atoms, benzyl substituted on the phenyl ring with up to two groups selected from alkoxy of 1 to 4 carbon atoms, halogen, alkyl of 1 to 4 carbon atoms, or nitro;

$R^8$ is phenylalkenyl wherein the aliphatic portion is 2 to 4 carbon atoms, —$(CH_2)_m$-imidazol-1yl, —$(CH_2)_m$1,2,3-triazolyl optionally substituted with one or two groups selected from $CO_2CH_3$ or alkyl of 1 to 4 carbon atoms,

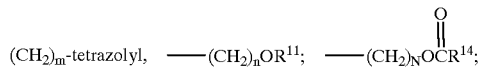

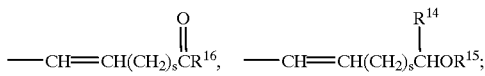

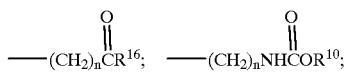

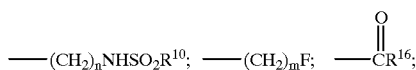

$R^{13}$ is —$CO_2H$, —$CO_2R^9$, $NHSO_2CF_3$; $SO_3H$; or

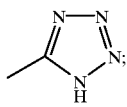

$R^{16}$ is H, alkyl of 1 to 5 carbon atoms, $OR^{17}$, or $NR^{18}R^{19}$;

X is carbon—carbon single bond,

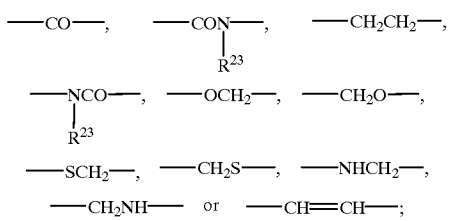

or pharmaceutically acceptable salts of these compounds.

6. The method as recited in claim 5, wherein the angiotensin II receptor antagonist is of formula I wherein:

$R^2$ is H, alkyl of 1 to 4 carbon atoms, halogen, or alkoxy of 1 to 4 carbon atoms;

$R^6$ is alkyl, alkenyl or alkynyl of 3 to 7 carbon atoms;
$R^7$ is H, Cl, Br, $C_vF_{2v+1}$, where v=1–3, or

$R^8$ is

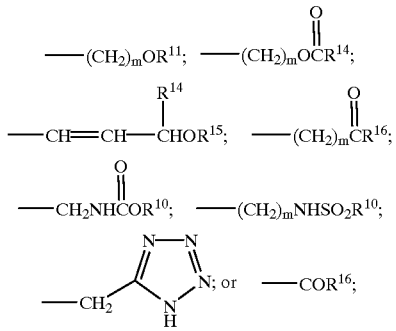

$R^{10}$ is $CF_3$, alkyl of 1 to 6 carbon atoms or phenyl;
$R^{11}$ is H, or alkyl of 1 to 4 carbon atoms;
$R^{13}$ is $CO_2H$; $CO_2CH_2OCOC(CH_3)_3$; $NHSO_2CF_3$; or

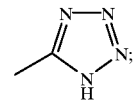

$R^{14}$ is H, or alkyl of 1 to 4 carbon atoms;
$R^{15}$ is H, alkyl of 1 to 4 carbon atoms, or acyl of 1 to 4 carbon atoms;
$R^{16}$ is H, alkyl of 1 to 5 carbon atoms; $OR_{17}$; or

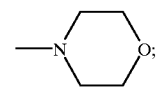

m is 1 to 5;
X is single bond, —O—; —CO—; —NHCO—; or —OCH$_2$—; or pharmaceutically acceptable salts thereof.

7. The method as recited in claim 4, wherein the angiotensin II receptor antagonist of formula I is selected from the group consisting of:
2-Butyl-4-chloro-1-[(2'-(1H-tetrazol-5-yl)biphenyl-4-yl)methyl]-5-(hydroxymethyl)imidazole.
2-Butyl-4-chloro-1-[(2'-carboxybiphenyl-4-yl)methyl]-5-(hydroxymethyl)imidazole.
2-Butyl-4-chloro-1-[(2'-carboxybiphenyl-4-yl)methyl]-5-[(methoxycarbonyl)aminomethyl]imidazole.
2-Butyl-4-chloro-1-[(2'-carboxybiphenyl-4-yl)methyl]-5-[(propoxycarbonyl)aminomethyl]imidazole.
2-Butyl-4-chloro-1-[(2'-carboxybiphenyl-4-yl)methyl]imidazole-5-carboxaldehyde.
2-Butyl-1-[(2'-carboxybiphenyl-4-yl)methyl]-imidazole-5-carboxaldehyde.
2-(1E-Butenyl)-4-chloro-1-[(2'-carboxybiphenyl-4-yl)methyl]-5-(hydroxymethyl)imidazole.
2-(1E-Butenyl)-4-chloro-1-[(2'-carboxybiphenyl-4-yl)methyl]-imidazole-5-carboxaldehyde.

2-Propyl-4-chloro-1-[(2'-(1H-tetrazol-5-yl)biphenyl-4-yl) methyl]-5-(hydroxymethyl)imidazole.

2-Propyl-4-chloro-1-[(2'-(1H-tetrazol-5-yl)biphenyl-4-yl) methyl]-imidazole-5-carboxaldehyde.

2-Butyl-4-chloro-1-[(2'-(1H-tetrazol-5-yl)biphenyl-4-yl) methyl]-imidzole-5-carboxaldehyde.

2-(1E-Butenyl)-4-chloro-1-[(2'-(1H-tetrazol-5-yl)biphenyl-4-yl)methyl]-5-hydroxymethyl)imidazole.

2(1E-Butenyl)-4-chloro-1-[(2'-(1H-tetrazol-5-yl)biphenyl-4-yl)methyl]imidazole-5-carboxaldehyde.

2-Butyl-4-chloro-1-[(2'-(1H-tetrazol-5-yl)-biphenyl-4-yl) methyl]-imidazole-5-carboxylic acid.

2-Propyl-4-chloro-1-[(2-'(1H-tetrazol-5-yl)-biphenyl-4-yl) methyl]-imidazole-5-carboxylic acid.

2-Propyl-4-trifluoromethyl-1-[(2'-(1H-tetrazol-5-yl) biphenyl-4-yl)methyl]imidazole-5-carboxylic acid.

2-Propyl-4-trifluoromethyl-1-[(2'-(1H-tetrazol-5-yl) biphenyl-4-yl)methyl]-5-(hydroxylmethyl)imidazole.

2-Butyl-4-trifluoromethyl-1-[(2'-(1H-tetrazol-5-yl) biphenyl-4-yl)methyl]imidazole-5-carboxylic acid.

2-Propyl-4-trifluoromethyl-1[(2'-(carboxybiphenyl-4-yl) methyl]-imidazole-5-carboxaldehyde. 2-Propyl-4-pentafluoroethyl-1-[(2'-(1H-tetrazol-5-yl)biphenyl-4-yl) methyl]-5-(hydroxymethyl)imidazole.

2-Propyl-1-[(2-(1H-tetrazol-5-yl)biphenyl-4-yl)methyl] imidazole-4,5,-dicarboxylic acid.

2-Propyl-4-pentafluoroethyl-1-[(2'-(1H-tetrazol-5-yl) biphenyl-4-yl)methyl]imidazole-5-carboxylic acid, and 2-Propyl-4-pentafluoroethyl-[(2'-(1H-tetrazol-5-yl) biphenyl-4-yl)methyl]imidazole-5-carboxaldehyde, or a pharmaceutically acceptable salt thereof.

8. The method as recited in claim 7, wherein the angiotensin II receptor antagonist of formula I is:

2-Butyl-4-chloro-1-[(2'-tetrazol-5-yl)biphenyl-4-yl] methyl]-5-(hydroxymethyl)imidazole; or 2-Butyl-4-chloro-1-[(2'-tetrazol-5-yl)biphenyl-4-yl] methylimidazole-5-carboxylic acid or a pharmaceutically acceptable salt thereof.

9. The method as recited in claim 8, wherein the symptomatic heart failure patient is 65 years of age or older.

10. A method for reducing sudden cardiac death rates by administering to chronic symptomatic heart failure patients a therapeutically effective amount of an angiotensin II receptor antagonist.

11. A method for reducing sudden cardiac death rates by administering to chronic symptomatic heart failure patients a therapeutically effective amount of an angiotensin II receptor antagonist selected from the group consisting of: candesartan cilexetil, eprosartan, irbesartan, losartan, tasosartan, telmisartan, valsartan, 3-(2'-(tetrazol-5-yl)-1,1'-biphen-4-yl)methyl-5,7-dimethyl-2-ethyl-3H-imidazo[4,5-b]pyridine, 4'[2-ethyl-4-methyl-6-(5,6,7,8-tetrahydroimidazo[1,2-a]pyridin-2-yl]-benzimidazol-1-yl]-methyl]-1,1'-biphenyl]-2-carboxylic acid, 2-butyl-6-(1-methoxy-1-methylethyl)-2-[2'-(1H-tetrazol-5-yl)biphenyl-4-ylmethyl]guinazolin-4(3H)-one, 3-[(2'-carboxybiphenyl-4-yl)methyl]-2-cyclopropyl-7-methyl-3H-imidazo[4,5-b] pyridine, 2-butyl-4-chloro-1-[(2'-tetrazol-5-yl)biphenyl-4-yl)methyl]imidazole-carboxylic acid, 2-butyl-4-chloro-1-[[2'-(1H-tetrazol-5-yl)[1,1'-biphenyl]-4-yl]methyl]-1H-imidazole-5-carboxylic acid-1-(ethoxycarbonyl-oxy)ethyl ester potassium salt, dipotassium 2-butyl-4-(methylthio)-1-[[2-[[[(propylamino)carbonyl]amino]sulfonyl](1,1'-biphenyl)-4-yl]methyl]-1H-imidazole-5-carboxylate, methyl-2-[[4-butyl-2-methyl-6-oxo-5-[[2'-(1H-tetrazol-5-yl)-[1,1'-biphenyl]-4-yl]methyl]-1-(6H)-pyrimidinyl] methyl]3-thiophencarboxylate, 5-[(3,5-dibutyl-1H-1,2,4-triazol-1-yl)methyl]-2-[2-(1H-tetrazol-5-ylphenyl)] pyridine, 6-butyl-2-(2-phenylethyl)-5-[[2'-(1H-tetrazol-5-yl)[1,1'-biphenyl]-4-methyl]pyrimidin-4-(3H)-one D,L lysine salt, 5-methyl-7-n-propyl-8-[[2'-(1H-tetrazol-5-yl) biphenyl-4-yl]methyl]-[1,2,4]-triazolo[1,5-c]pyrimidin - 2(3H)-one, 2,7-diethyl-5-[[2'-(5-tetrazolyl)biphenyl-4-yl] methyl]-5H-pyrazolo[1,5-b][1,2,4]triazole potassium salt, 2-[2-butyl-4,5-dihydro-4-oxo-3-[2'-(1H-tetrazol-5-yl)-4-biphenylmethyl]-3H-imidazol[4,5-c]pyridine-5-ylmethyl]-benzoic acid, ethyl ester, potassium salt, 3-methoxy-2,6-dimethyl-4-[[2'-(1H-tetrazol-5-yl)-1,1'-biphenyl-4-yl] methoxy]pyridine, 2-ethoxy-1-[[2'-(5-oxo-2,5-dihydro-1,2,4-oxadiazol-3-yl)biphenyl-4-yl]methyl]-1H-benzimidazole-7-carboxylic acid, 1-[N-(2'-(1H-tetrazol-5-yl)biphenyl-4-yl-methyl)-N-valerolylaminomethyl)cyclopentane-1-carboxylic acid, 7-methyl-2n-propyl-3-[[2'1H-tetrazol-5-yl) biphenyl-4-yl]methyl]-3H-imidazo[4,5-6]pyridine, 2-[5-[(2-ethyl-5,7-dimethyl-3H-imidazo[4,5-b]pyridine-3-yl) methyl]-2-quinolinyl]sodium benzoate, 2-butyl-6-chloro-4-hydroxymethyl-5-methyl-3-[[2'-(1H-tetrazol-5-yl)biphenyl-4-yl]methyl]pyridine, 2-[[[2-butyl-1-[(4-carboxyphenyl) methyl]-1H-imidazol-5-yl]methyl]amino]benzoic acid tetrazol-5-yl)biphenyl-4-yl]methyl]pyrimidin-6-one, 4(S)-[4-(carboxymethyl)phenoxy]-N-[2(R)-[4-(2-sulfobenzamido)imidazol-1-yl]octanoyl]-L-proline, 1-(2,6-dimethylphenyl)-4-butyl-1,3-dihydro-3-[[6-[2-(1H-tetrazol-5-yl)phenyl]-3-pyridinyl]methyl]-2H-imidazol-2-one, 5,8-ethano-5,8-dimethyl-2-n-propyl-5,6,7,8-tetrahydro-1-[[2'-(1H-tetrazol-5-yl)biphenyl-4-yl]methyl]-1H,4H-1,3,4a,8a-tetrazacyclopentanaphthalene-9-one, 4-[1-[2'-(1,2,3,4-tetrazol-5-yl)biphen-4-yl)methylamino]-5,6,7,8-tetrahydro-2-trifylquinazoline, 2-(2-chlorobenzoyl)imino-5-ethyl-3-[2'-(1H-tetrazole-5-yl)biphenyl-4-yl)methyl-1,3,4-thiadiazoline, 2-[5-ethyl-3-[2-(1H-tetrazole-5-yl)biphenyl-4-yl]methyl-1,3,4-thiazoline-2-ylidene]aminocarbonyl-1-cyclopentencarboxylic acid dipotassium salt, and 2-butyl-4-N-methyl-N-(3-methylcrotonoyl)amino]-1-[[2'-(1H-tetrazol-5-yl)biphenyl-4-yl]methyl]-1H-imidazole-5-carboxylic acid 1-ethoxycarbonyloxyethyl ester.

12. The method as recited in claim 11, wherein the angiotensin II receptor antagonist is selected from the group consisting of: candesartan cilexetil, eprosartan, irbesartan, losartan, tasosartan, telmisartan, valsartan, and 3-(2'-(tetrazol-5-yl)-1,1'-biphen-4-yl)methyl-5,7-dimethyl-2-ethyl-3H-imidazo[4,5-b]pyridine.

13. A method for reducing sudden cardiac death rates by administering to chronic symptomatic heart failure patients a therapeutically effective amount of an angiotensin II receptor antagonist of formula I

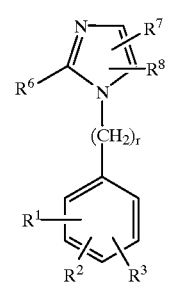

I wherein:

R¹ is:

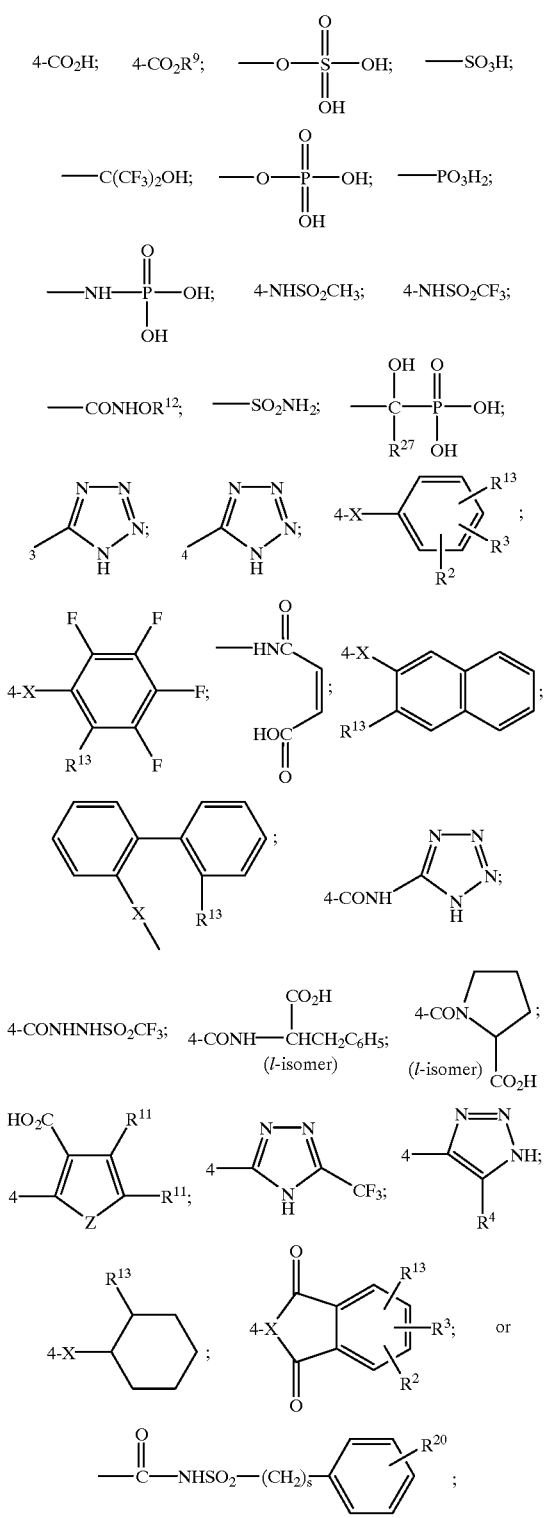

R² is H; Cl; Br; I; F; NO₂; CN; alkyl of 1 to 4 carbon atoms; acyloxy of 1 to 4 carbon atoms; alkoxy of 1 to 4 carbon atoms; $CO_2H$; $CO_2R^9$; $HNSO_2CH_3$; $NHSO_2CF_3$; $CONHOR^{12}$; $SO_2NH_2$, aryl; or furyl;

$R^3$ is H; Cl, Br, I or F; alkyl of 1 to 4 carbon atoms or alkoxy of 1 to 4 carbon atoms;

$R^4$ is CN, $NO_2$ or $CO_2R^{11}$;

$R^5$ is H, alkyl of 1 to 6 carbon atoms, cycloalkyl of 3 to 6 carbon atoms alkenyl or alkynyl of 2 to 4 carbon atoms;

$R^6$ is alkyl of 2 to 10 carbon atoms, alkenyl or alkynyl of 3 to 10 carbon atoms or the same groups substituted with F or $CO_2R^{14}$; cycloalkyl of 3 to 8 carbon atoms, cycloalkylalkyl, of 4 to 10 carbon atoms; cycloalkylalkenyl or cycloalkylalkynyl 5 to 10 carbon atoms; $(CH_2)_sZ(CH_2)_mR^5$ optionally substituted with F or $CO_2R^{14}$; benzyl substituted on the phenyl ring with 1 or 2 halogens, alkoxy of 1 to 4 carbon atoms, alkyl of 1 to 4 carbon atoms or nitro;

$R^7$ is H, F, Cl, Br, I, $NO_2$, $C_vF_{2v+1}$, where v=1–6, $C_6F_5$; CN;

$$-\overset{O}{\underset{\|}{C}}-R^{16};$$

straight or branched alkyl of 1 to 6 carbon atoms; phenyl or phenylalkyl, where alkyl is 1 to 3 carbon atoms; or substituted phenyl or substituted phenylalkyl, where alkyl is 1 to 3 carbon atoms, substituted with one or two substituents selected from alkyl of 1 to 4 carbon atoms, F, Cl, Br, OH, $OCH_3$, $CF_3$, or COOR, where R is H, alkyl of 1 to 4 carbon atoms, or phenyl;

$R^8$ is H, CN, alkyl of 1 to 10 carbon atoms, alkenyl of 3 to 10 carbon atoms, or the same groups substituted with F; phenylalkenyl wherein the aliphatic portion is 2 to 6 carbon atoms; —$(CH_2)_m$-imidazol-1-yl; —$(CH_2)_m$-1,2,3-triazolyl optionally substituted with one or two group selected from $CO_2CH_3$ or alkyl of 1 to 4 carbon atoms; —$(CH_2)_s$ tetrazolyl;

—$(CH_2)_{n-1}\underset{OR^{17}}{CH}$—$R^{11}$;  —$(CH_2)_n O\overset{O}{\underset{\|}{C}}R^{14}$;  —$(CH_2)_n SR^{15}$;

—CH=CH$(CH_2)_s\underset{R^{14}}{CH}OR^{15}$;  —CH=CH$(CH_2)_s\overset{O}{\underset{\|}{C}}R^{16}$;

—$\overset{O}{\underset{\|}{C}}R^{16}$;  —CH=CH$(CH_2)_s O\overset{}{\underset{\|}{C}}R^{11}$;

$(CH_2)_s$—CH—$COR^{16}$;
    |
    $CH_3$

—$(CH_2)_n\overset{O}{\underset{\|}{C}}R^{16}$;

—$(CH_2)_n O\overset{Y}{\underset{\|}{C}}NHR^{10}$;  —$(CH_2)_n NR^{11}\overset{Y}{\underset{\|}{C}}OR^{10}$;

—$(CH_2)_n NR^{11}\overset{O}{\underset{\|}{C}}NHR^{10}$;  —$(CH_2)_n NR^{11}SO_2R^{10}$;

-continued

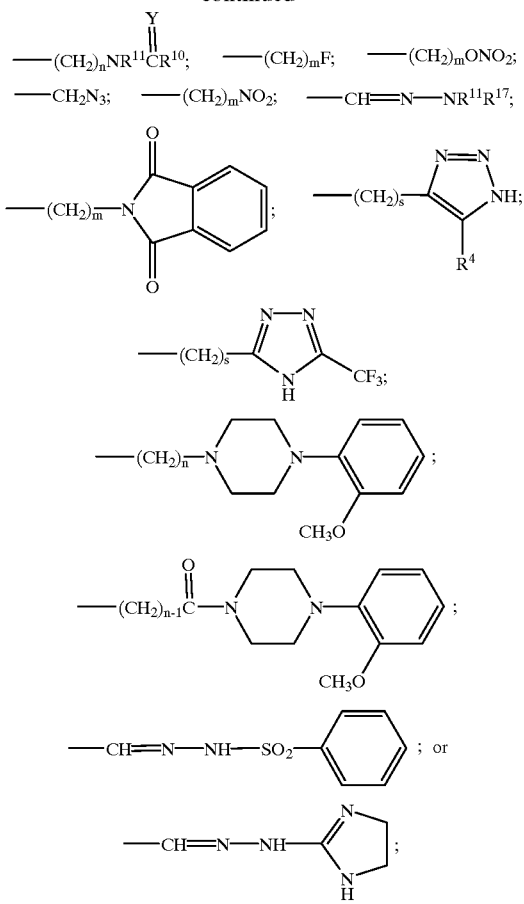

$R^9$ is:

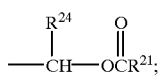

$R^{10}$ is alkyl of 1 to 6 carbon atoms or perfluoroalkyl of 1 to 6 carbon atoms, 1-adamantyl, 1-naphthyl, 1-(1-naphthyl)ethyl, or $(CH_2)_pC_6H_5$;

$R^{11}$ is H, alkyl of 1 to 6 carbon atoms, cycloalkyl of 3 to 6 carbon atoms, phenyl or benzyl;

$R^{12}$ is H, methyl or benzyl;

$R^{13}$ is

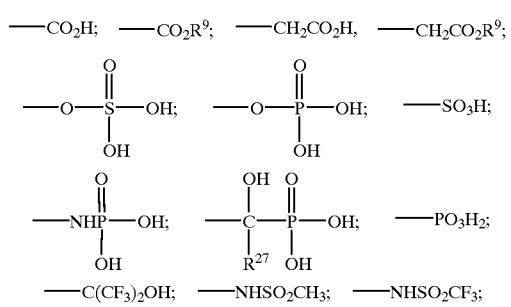

-continued

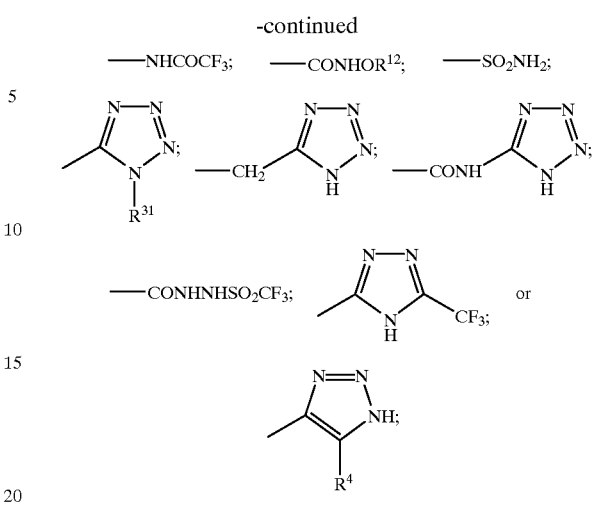

$R^{14}$ is H, alkyl or perfluoroalkyl of 1 to H carbon atoms, cycloalkyl of 3 to 6 carbon atoms, phenyl or benzyl;

$R^{15}$ is H, alkyl of 1 to 6 carbon atoms, cycloalkyl of 3 to 6 carbon atoms, phenyl, benzyl, acyl of 1 to 4 carbon atoms, or phenacyl;

$R^{16}$ is H, alkyl of 1 to 6 carbon atoms, cycloalkyl of 3 to 6 carbon atoms, $(CH_2)_pC_6H_5$, $OR^{17}$, or $NR^{18}R^{19}$;

$R^{17}$ is H, alkyl of 1 to 6 carbon atoms, cycloalkyl of 3 to 6 carbon atoms, phenyl or benzyl;

$R^{18}$ and $R^{19}$ independently are H, alkyl of 1 to 4 carbon atoms, phenyl, benzyl, a-methylbenzyl, or taken together with the nitrogen form a ring of the formula

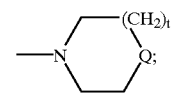

Q is $NR^{20}$, O or $CH_2$;

$R^{20}$ is H, alkyl of 1–4 carbon atoms, or phenyl;

$R^{21}$ is alkyl of 1 to 6 carbon atoms, $-NR^{22}R^{23}$, or

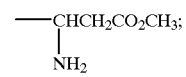

$R^{22}$ and $R^{23}$ independently are H, alkyl of 1 to 6 carbon atoms, benzyl, or are taken together as $(CH_2)_u$, where u is 3–6;

$R^{24}$ is H, $CH_3$ or $-C_6H_5$;

$R^{25}$ is $NR^{27}R^{28}$, $OR^{28}$, $NHCONH_2$, $NHCSNH_2$,

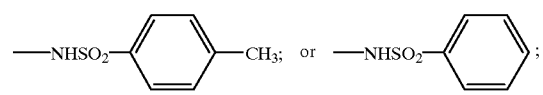

$R^{26}$ is hydrogen, alkyl with from 1 to 6 carbon atoms, benzyl, or allyl;

$R^{27}$ and $R^{28}$ are independently hydrogen, alkyl with from 1 to 5 carbon atoms, or phenyl;

$R^{29}$ and $R^{30}$ are independently alkyl of 1–4 carbon atoms or taken together are —$(CH_2)_q$—;

$R^{31}$ is H, alkyl or 1 to 4 carbon atoms, —$CH_2CH=CH_2$ or —$CH_2C_6H_4R^{32}$;

X is a carbon—carbon single bond,

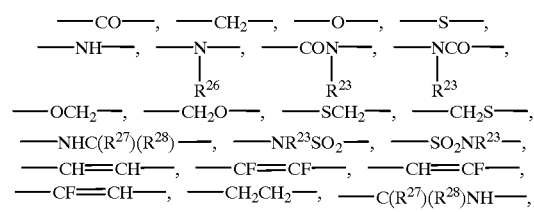

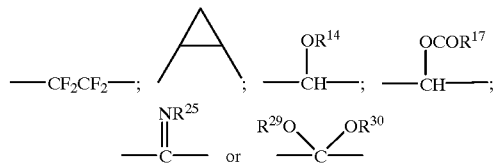

Y is O or S;

Z is O, $NR^{11}$, or S;

m is 1 to 5;

n is 1 to 10;

p is 0 to 3;

q is 2 to 3;

r is 0 to 2;

s is 0 to 5;

t is 0 or 1;

or pharmaceutically acceptable salts of these compounds; provided that:

(1) the $R^1$ group is not in the ortho position;

(2) when $R^1$ is

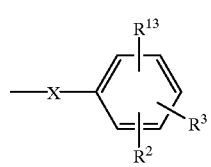

X is a single bond, and $R^{13}$ is $CO_2H$, or

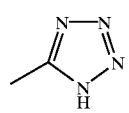

then $R^{13}$ must be in the ortho or meta position; or when $R^1$ and X are as above and $R^{13}$ is $NHSO_2CF_3$ or $NHSO_2CH_3$, $R^{13}$ must be ortho;

(3) when $R^1$ is

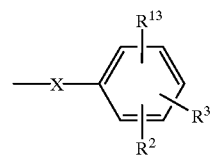

and X is other than a single bond, then $R^{13}$ must be ortho except when $X=NR_{23}CO$ and $R^{13}$ is $NHSO_2CF_3$ or $NHSO_2CH_3$, then $R^{13}$ must be ortho or meta;

(4) when $R^1$ is $4-CO_2H$ or ai salt thereof, $R^6$ cannot be S-alkyl;

(5) when $R^1$ is $4-CO_2H$ or a salt thereof, the substituent on the 4-position of the imidazole cannot be $CH_2OH$, $CH_2OCOCH_3$, or $CH_2CO_2H$;

(6) when $R^1$ is

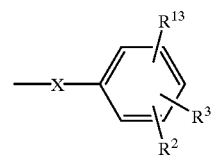

X is —$OCH_2$—, and $R^{13}$ is $2-CO_2H$, and $R^7$ is H then $R^6$ is not $C_2H_5S$;

(7) when $R^1$ is

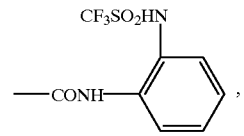

and $R^6$ is n-hexyl then $R^7$ and $R^8$ are not both hydrogen;

(8) when $R^1$ is

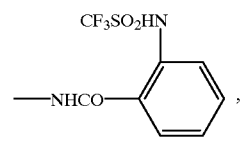

$R^6$ is not methoxybenzyl;

(9) the $R^6$ group is not

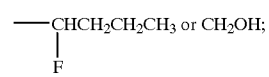

(10) when r=0, $R^1$ is

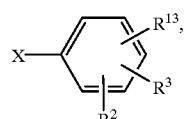

X is

$R^{13}$ is 2-NHSO$_2$CF$_3$, and $R^6$ is n-propyl, then $R^7$ and $R^8$ are not —CO$_2$CH$_3$;

(11) when r=0, $R^1$ is

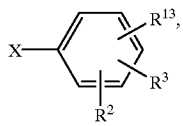

X is

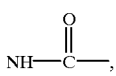

$R^{13}$ is 2-COOH, and $R^6$ is n-propyl, then $R^7$ and $R^8$ are not —CO$_2$CH$_3$;

(12) when r=1,

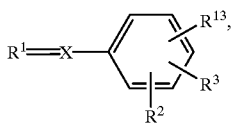

X is a single bond, $R^7$ is Cl, and $R^8$ is —CHO, then $R^{13}$ is not 3-(tetrazol-5-yl);

(13) when r=1,

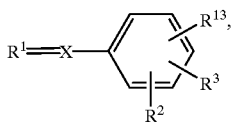

X is a single bond, $R^7$ is Cl, and $R^8$ is —CHO, then $R^{13}$ is not 4-(tetrazol-5-yl).

14. The method as recited in claim 13, wherein the angiotensin 11 receptor antagonist is losartan or EXP-3174, or a pharmaceutically acceptable salt thereof.

15. The method as recited in claim 14, wherein the symptomatic heart failure patient is 65 years of age or older.

16. A method for reducing mortality and sudden cardiac death rates by administering to chronic symptomatic heart failure patients a therapeutically effective amount of an angiotensin II receptor antagonist.

17. A method for reducing mortality and sudden cardiac death rates by administering to chronic symptomatic heart failure patients a therapeutically effective amount of an angiotensin II receptor antagonist selected from the group consisting of: candesartan cilexetil, eprosartan, irbesartan, losartan, tasosartan, telmisartan, valsartan, 3-(2'-(tetrazol-5-yl)-1,1'-biphen-4-yl)methyl-5,7-dimethyl-2-ethyl-3H-imidazo[4,5-b]pyridine, 4'2-ethyl-4-methyl-6-(5,6,7,8-tetrahydroimidazol[1,2-a]pyridin-2-yl)-benzimidazol-1-yl]-methyl]-1,1'-biphenyl]-2-carboxylic acid, 2-butyl-6-(1-methoxy-1-methylethyl)-2-[2'-(1H-tetrazol-5-yl)biphenyl-4-ylmethyl]guinazolin-4(3H)-one, 3-[(2'-carboxybiphenyl-4-yl)methyl]-2-cyclopropyl-7-methyl-3H-imidazo[4,5-b]pyridine, 2-butyl-4-chloro-1-[(2'-tetrazol-5-yl)biphenyl-4-yl)methyl]imidazole-carboxylic acid, 2-butyl-4-chloro-1-[[2'-(1H-tetrazol-5-yl)[1,1'-biphenyl]-4-yl]methyl]-1H-imidazole-5-carboxylic acid-1-(ethoxycarbonyl-oxy)ethyl ester potassium salt, dipotassium 2-butyl-4-(methylthio)-1-[[2-[[[(propylamino)carbonyl]amino]sulfonyl(1,1'-biphenyl)-4-yl]methyl]-1H-imidazole-5-carboxylate, methyl-2-[[4-butyl-2-methyl-6-oxo-5-[[2'-(1H-tetrazol-5-yl) -[1,1'-biphenyl]-4-yl]methyl]-1-(6H)-pyrimidinyl] methyl]-3-thiophencarboxylate, 5-[(3,5-dibutyl-1H-1,2,4-triazol-1-yl)methyl]-2-[2-(1H-tetrazol-5-ylphenyl)] pyridine, 6-butyl-2-(2-phenylethyl)-5-[[2'-(1H-tetrazol-5-yl)[1,1'-biphenyl]-4-methyl]pyrimidin-4-(3H)-one D,L lysine salt, 5-methyl-7-n-propyl-8-[[2'-(1H-tetrazol-5-yl)biphenyl-4-yl]methyl]-[1,2,4]-triazolo[1,5-c]pyrimidin-2 (3H)-one, 2,7-diethyl-5-[[2'-(5-tetrazolyl)biphenyl-4-yl]methyl]-5H-pyrazolo[1,5-b][1,2,4]triazole potassium salt, 2-[2-butyl-4,5-dihydro-4-oxo-3-[2'-(1H-tetrazol-5-yl)-4-biphenylmethyl]-3H-imidazol[4,5-c]pyridine-5-ylmethyl]-benzoic acid, ethyl ester, potassium salt, 3-methoxy-2,6-dimethyl-4-[[2'-(1H-tetrazol-5-yl)-1,1'-biphenyl-4-yl]methoxy]pyridine, 2-ethoxy-1-[[2'-(5-oxo-2,5-dihydro-1,2,4-oxadiazol-3-yl)biphenyl-4-yl]methyl]-1H-benzimidazole-7-carboxylic acid, 1-[N-(2'-(1H-tetrazol-5-yl)biphenyl-4-yl-methyl)-N-valerolylaminomethyl)cyclopentane-1-carboxylic acid, 7-methyl-2n-propyl-3-[[2'1H-tetrazol-5-yl)biphenyl-4-yl]methyl]-3H-imidazo[4,5-6]pyridine, 2-[5-[(2-ethyl-5,7-dimethyl-3H-imidazo[4,5-b]pyridine-3-yl)methyl]-2-quinolinyl]sodium benzoate, 2-butyl-6-chloro-4-hydroxymethyl-5-methyl-3-[[2'-(1H-tetrazol-5-yl)biphenyl-4-yl]methyl]pyridine, 2-[[[2-butyl-1-[(4-carboxyphenyl)methyl]-1H-imidazol-5-yl]methyl]amino]benzoic acid tetrazol-5-yl)biphenyl-4-yl]methyl]pyrimidin-6-one, 4(S)-[4-(carboxymethyl)phenoxy]-N-[2(R)-[4-(2-sulfobenzamido)imidazol-1-yl]octanoyl]-L-proline, 1-(2,6-dimethylphenyl)-4-butyl-1,3-dihydro-3-[[6-[2-(1H-tetrazol-5-yl)phenyl]-3-pyridinyl]methyl]-2H-imidazol-2-one, 5,8-ethano-5,8-dimethyl-2-n-propyl-5,6,7,8-tetrahydro-1-[[2'-(1H-tetrazol-5-yl)biphenyl-4-yl]methyl]-1H,4H-1,3,4a,8a-tetrazacyclopentanaphthalene-9-one, 4-[1--[2'-(1,2,3,4-tetrazol-5-yl)biphen-4-yl)methylamino]-5,6,7,8-tetrahydro-2-trifylquinazoline, 2-(2-chlorobenzoyl)imino-5-ethyl-3-[2'-(1H-tetrazole-5-yl)biphenyl-4-yl)methyl-1,3,4-thiadiazoline, 2-[5-ethyl-3-[2-(1H-tetrazole-5-yl)biphenyl-4-yl]methyl-1,3,4-thiazoline-2-ylidene]aminocarbonyl-1-cyclopentencarboxylic acid dipotassium salt, and 2-butyl-4-[N-methyl-N-(3-methylcrotonoyl)amino]-1-[[2'-(1H-tetrazol-5-yl)biphenyl-4-yl]methyl]-1H-imidazole-5-carboxylic acid 1-ethoxycarbonyloxyethyl ester.

18. The method as recited in claim 16, wherein the angiotensin II receptor antagonist is selected from the group consisting of: candesartan cilexetil, eprosartan, irbesartan, losartan, tasosartan, telmisartan, valsartan, and 3-(2'-(tetrazol-5-yl)-1,1'-biphen-4-yl)methyl-5,7-dimethyl-2-ethyl-3H-imidazo[4,5-b]pyridine.

19. A method for reducing sudden cardiac death rates by administering to chronic symptomatic heart failure patients a therapeutically effective amount of an angiotensin II antagonist formula I

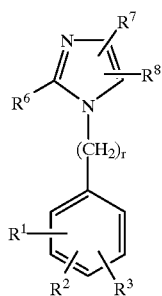

wherein:

R¹ is:

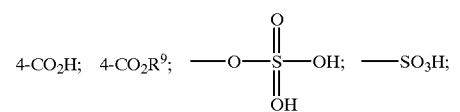

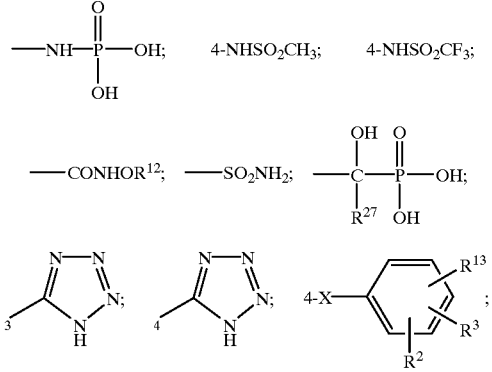

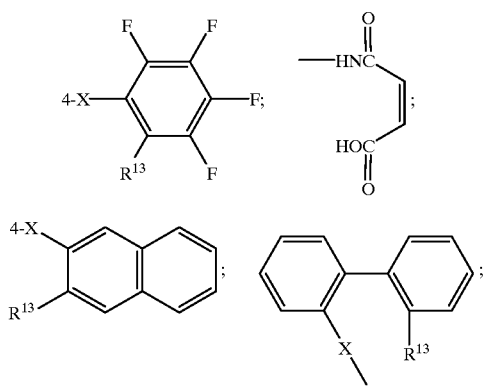

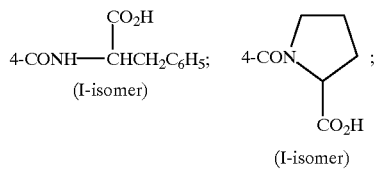

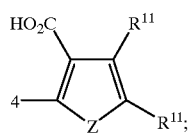 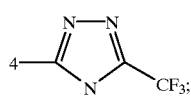

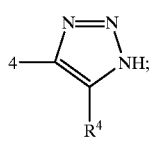 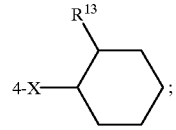

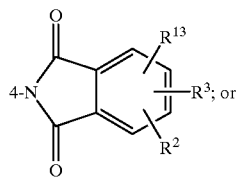

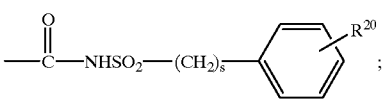

R² is H; Cl; Br; I; F; NO₂; CN; alkyl of 1 to 4 carbon atoms; acyloxy of 1 to 4 carbon atoms; alkoxy of 1 to 4 carbon atoms; $CO_2H$; $CO_2R^9$; $HNSO_2CH_3$; $NHSO_2CF_3$; $CONHOR^{12}$; $SO_2NH_2$;

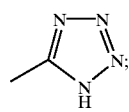

aryl; or furyl;

R³ is H; Cl, Br, I or F; alkyl of 1 to 4 carbon atoms or alkoxy of 1 to 4 carbon atoms;

R⁴ is CN, NO₂ or $CO_2R^{11}$;

R⁵ is H, alkyl of 1 to 6 carbon atoms, cycloalkyl of 3 to 6 carbon atoms alkenyl or alkynyl of 2 to 4 carbon atoms;

R⁶ is alkyl of 2 to 10 carbon atoms, alkenyl or alkynyl of 3 to 10 carbon atoms or the same groups substituted with F or $CO_2R^{14}$; cycloalkyl of 3 to 9 carbon atoms, cycloalkylalkyl, of 4 to 10 carbon atoms; cycloalkylalkenyl or cycloalkylalkynyl 5 to 10 carbon atoms; $(CH_2)_sZ(CH_2)_mR^5$ optionally substituted with F or $CO_2R^{14}$; benzyl substituted on the phenyl ring with 1 or 2 halogens, alkoxy of 1 to 4 carbon atoms, alkyl of 1 to 4 carbon atoms or nitro;

R⁷ is H, F, Cl, Br, I, NO₂, $C_vF_{2v+1}$, where v=1–6, $C_6F_5$; CN;

$$-\overset{O}{\underset{}{C}}-R^{16};$$

straight or branched alkyl of 1 to 6 carbon atoms; phenyl or phenylalkyl, where alkyl is 1 to 3 carbon atoms; or substituted phenyl or substituted phenylalkyl, where alkyl is 1 to 3 carbon atoms, substituted with one or two substituents selected from alkyl of 1 to 4 carbon atoms, F, Cl, Br, OH, OCH$_3$, CF$_3$, or COOR, where R is H, alkyl of 1 to 4 carbon atoms, or phenyl;

$R^8$ is H, CN, alkyl of 1 to 10 carbon atoms, alkenyl of 3 to 10 carbon atoms, or the same groups substituted with F; phenylalkenyl wherein the aliphatic portion is 2 to 6 carbon atoms; —(CH$_2$)$_m$-imidazol-1-yl; —(CH$_2$)$_m$-1,2,3-triazolyl optionally substituted with one or two group selected from CO$_2$CH$_3$ or alkyl of 1 to 4 carbon atoms; —(CH$_2$)$_s$ tetrazolyl;

—(CH$_2$)$_{n-1}$CH(OR$^{17}$)—R$^{11}$;   —(CH$_2$)$_n$OCR$^{14}$(=O);   —(CH$_2$)$_n$SR$^{15}$;

—CH=CH(CH$_2$)$_s$CHOR$^{15}$(R$^{14}$);   —CH=CH(CH$_2$)$_s$CR$^{16}$(=O);

—CR$^{16}$(=O);   —CH=CH(CH$_2$)$_s$OCR$^{11}$(=O);

(CH$_2$)$_s$—CH(CH$_3$)—COR$^{16}$;   —(CH$_2$)$_n$CR$^{16}$(=O);

—(CH$_2$)$_n$OC(Y)NHR$^{10}$;   —(CH$_2$)$_n$NR$^{11}$C(Y)OR$^{10}$;

—(CH$_2$)$_n$NR$^{11}$C(=O)NHR$^{10}$;   —(CH$_2$)$_n$NR$^{11}$SO$_2$R$^{10}$;

—(CH$_2$)$_n$NR$^{11}$C(Y)R$^{10}$;   —(CH$_2$)$_m$F;   —(CH$_2$)$_m$ONO$_2$;

—CH$_2$N$_3$;   —(CH$_2$)$_m$NO$_2$;   —CH=N—NR$^{11}$R$^{17}$;

—(CH$_2$)$_m$-N-phthalimidoyl;   —(CH$_2$)$_s$-triazolyl(R$^4$)NH;

—(CH$_2$)$_s$-triazolyl(CF$_3$)NH;

—(CH$_2$)$_n$-N-piperazinyl(2-methoxyphenyl);

-continued

—(CH$_2$)$_{n-1}$C(=O)-N-piperazinyl(2-methoxyphenyl);

—CH=N—NH—SO$_2$-phenyl; or

—CH=N—NH-imidazolin-2-yl;

$R^9$ is:

$$-\underset{R^{24}}{\underset{|}{CH}}-OCR^{21}(=O);$$

$R^{10}$ is alkyl of 1 to 6 carbon atoms or perfluoroalkyl of 1 to 6 carbon atoms, 1-adamantyl, 1-naphthyl, 1-(1-naphthyl)ethyl, or (CH$_2$)$_p$C$_6$H$_5$;

$R^{11}$ is H, alkyl of 1 to 6 carbon atoms, cycloalkyl of 3 to 6 carbon atoms, phenyl or benzyl;

$R^{12}$ is H, methyl or benzyl;

$R^{13}$ is

—CO$_2$H;   —CO$_2$R$^9$;   —CH$_2$CO$_2$H;   —CH$_2$CO$_2$R$^9$;

—O—S(=O)(OH)—OH;   —O—P(=O)(OH)—OH;   —SO$_3$H;

—NHP(=O)(OH)—OH;   —C(R$^{27}$)(OH)—P(=O)(OH)—OH;   —PO$_3$H$_2$;

—C(CF$_3$)$_2$OH;   —NHSO$_2$CH$_3$;   —NHSO$_2$CF$_3$;

—NHCOCF$_3$;   —CONHOR$^{12}$;   —SO$_2$NH$_2$;

—tetrazolyl(R$^{31}$);   —CH$_2$-tetrazolyl-H;   —CONH-tetrazolyl-H;

—CONHNHSO$_2$CF$_3$;   —triazolyl(CF$_3$)H;   or   —triazolyl(R$^4$)methyl-NH;

$R^{14}$ is H, alkyl or perfluoroalkyl of 1 to 8 carbon atoms, cycloalkyl of 3 to 6 carbon atoms, phenyl or benzyl;

$R^{15}$ is H, alkyl of 1 to 6 carbon atoms, cycloalkyl of 3 to 6 carbon atoms, phenyl, benzyl, acyl of 1 to 4 carbon atoms, or phenacyl;

$R^{16}$ is H, alkyl of 1 to 6 carbon atoms, cycloalkyl of 3 to 6 carbon atoms, $(CH_2)_pC_6H_5$, $OR^{17}$, or $NR^{18}R^{19}$;

$R^{17}$ is H, alkyl of 1 to 6 carbon atoms, cycloalkyl of 3 to 6 carbon atoms, phenyl or benzyl;

$R^{18}$ and $R^{19}$ independently are H, alkyl of 1 to 4 carbon atoms, phenyl, benzyl, α-methylbenzyl, or taken together with the nitrogen form a ring of the formula

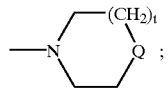

Q is $NR^{20}$, O or $CH_2$;

$R^{20}$ is H, alkyl of 1–4 carbon atoms, or phenyl;

$R^{21}$ is alkyl of 1 to 6 carbon atoms, $NR^{22}R^{23}$, or

$R^{22}$ and $R^{23}$ independently are H, alkyl of 1 to 6 carbon atoms, benzyl, or are taken together as $(CH_2)_u$, where u is 3–6;

$R^{24}$ is H, $CH_3$ or $—C_6H_5$;

$R^{25}$ is $NR^{27}R^{28}$, $OR^{28}$, $NHCONH_2$, $NHCSNH_2$,

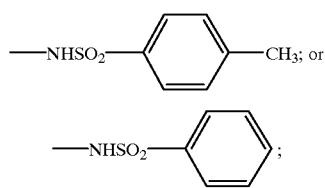

$R^{26}$ is hydrogen, alkyl with from 1 to 6 carbon atoms, benzyl, or allyl;

$R^{27}$ and $R^{28}$ are independently hydrogen, alkyl with from 1 to 5 carbon atoms, or phenyl;

$R^{29}$ and $R^{30}$ are independently alkyl of 1–4 carbon atoms or taken together are $—(CH_2)_q—$;

$R^{31}$ is H, alkyl or 1 to 4 carbon atoms, $—CH_2CH=CH_2$ or $—CH_2C_6H_4R^{32}$;

X is a carbon—carbon single bond,

—CO—, —CH$_2$—, —O—, —S—,

—NH—, —N(R$^{26}$)—, —CON(R$^{23}$)—, —NCO(R$^{23}$)—,

—OCH$_2$—, —CH$_2$O—, —SCH$_2$—, —CH$_2$S—,

—NHC(R$^{27}$)(R$^{28}$)—, —NR$^{23}$SO$_2$—, —SO$_2$NR$^{23}$—,

—CH=CH—, —CF=CF—, —CH=CF—,

—CF=CH—, —CH$_2$CH$_2$—, —C(R$^{27}$)(R$^{28}$)NH—,

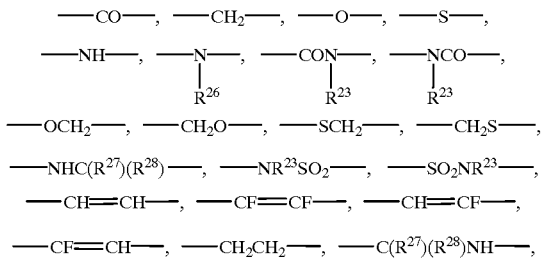

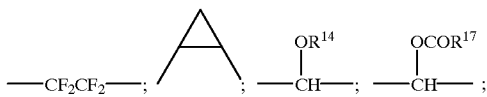

-continued

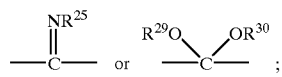

Y is O or S;

Z is O, $NR^{11}$, or S;

m is 1 to 5;

n is 1 to 10;

p is 0 to 3;

q is 2 to 3;

r is 0 to 2;

s is 0 to 5;

t is 0 or 1;

or pharmaceutically acceptable salts of these compounds; provided that:

(1) the $R^1$ group is not in the ortho position;

(2) when $R^1$ is

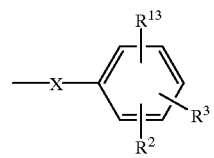

X is a single bond, and $R^{13}$ is $CO_2H$, or

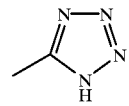

then $R^{13}$ must be in the ortho or meta position; or when $R^1$ and X are as above and $R^{13}$ is $NHSO_2CF_3$ or $NHSO_2CH_3$, $R^{13}$ must be ortho;

(3) when $R^1$ is

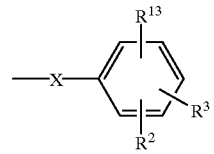

and X is other than a single bond, then $R^{13}$ must be ortho except when $X=NR^{23}CO$ and $R^{13}$ is $NHSO_2CF_3$ or $NHSO_2CH_3$, then $R^{13}$ must be ortho or meta;

(4) when $R^1$ is 4-$CO_2H$ or it salt thereof, $R^6$ cannot be S-alkyl;

(5) when $R^1$ is 4-$CO_2H$ or a salt thereof, the substituent on the 4-position of the imidazole cannot be $CH_2OH$, $CH_2OCOCH_3$, or $CH_2CO_2H$;

(6) when $R^1$ is

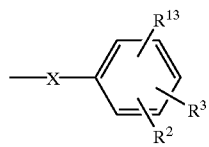

X is —OCH$_2$—, and $R^{13}$ is 2-CO$_2$H, and $R^7$ is H then $R^6$ is not C$_2$H$_5$S;

(7) when $R^1$ is

and $R^6$ is n-hexyl then $R^7$ and $R^8$ are not both hydrogen;

(8) when $R^1$ is

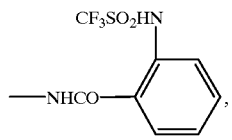

$R^6$ is not methoxybenzyl;

(9) the $R^6$ group is not

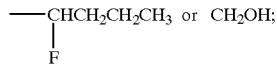

(10) when r=0, $R^1$ is

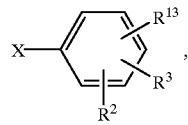

X is

$R^{13}$ is 2-NHSO$_2$CF$_3$, and $R^6$ is n-propyl, then $R^7$ and $R^8$ are not —CO$_2$CH$_3$;

(11) when r=0, $R^1$ is

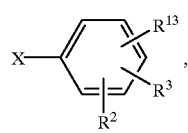

X is

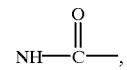

$R^{13}$ is 2-COOH, and $R^6$ is n-propyl, then $R^7$ and $R^8$ are not —CO$_2$CH$_3$;

(12) when r=1,

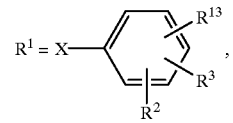

X is a single bond, $R^7$ is Cl, and $R^8$ is —CHO, then $R^{13}$ is not 3-(tetrazol-5-yl);

(13) when r=1,

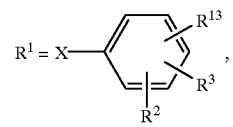

X is a single bond, $R^7$ is Cl, and $R^8$ is —CHO, then $R^{13}$ is not 4-(tetrazol-5-yl).

20. The method as recited in claim 19, wherein the angiotensin II receptor antagonist is losartan or EXP-3174 or its pharmaceutically acceptable salt thereof.

21. The method as recited in claim 20, wherein the symptomatic heart failure patient is 65 years of age or older.

22. A method for reducing the risk of sudden cardiac death by administering to chronic symptomatic heart failure patient a therapeutically effective amount of an angiotensin II receptor antagonist.

23. A method for reducing the risk of sudden cardiac death by administering to chronic symptomatic heart failure patient a therapeutically effective amount of an angiotensin II receptor antagonist selected from the group consisting of: candesartan cilexetil, eprosartan, irbesartan, losartan, tasosartan, telmisartan, valsartan, 3-(2'-(tetrazol-5-yl)-1,1'-biphen-4-yl)methyl-5,7-dimethyl-2-ethyl-3H-imidazo[4,5-b]pyridine, 4'[2-ethyl-4-methyl-6-(5,6,7,8-tetrahydroimidazo[1,2-a]pyridin-2-yl)-benzimidazol-1-yl]-methyl]-1,1'-biphenyl]-2-carboxylic acid, 2-butyl-6-(1-methoxy-1-methylethyl)-2-[2'-(1H-tetrazol-5-yl)biphenyl-4-ylmethyl]guinazolin-4(3H)-one, 3-[(2'-carboxybiphenyl-4-yl)methyl]-2-cyclopropyl-7-methyl-3H-imidazo[4,5-b]pyridine, 2-butyl-4-chloro-1-[(2'-tetrazol-5-yl)biphenyl-4-yl)methyl]imidazole-carboxylic acid, 2-butyl-4-chloro-1-[[2'-(1H-tetrazol-5-yl)[1,1'-biphenyl]-4-yl]methyl]-1H-imidazole-5-carboxylic acid-1-(ethoxycarbonyl-oxy)ethyl ester potassium salt, dipotassium 2-butyl-4-(methylthio)-1-[[2-[[[(propylamino)carbonyl]amino]-sulfonyl](1,1'-biphenyl)-4-yl]methyl]-1H-imidazole-5-carboxylate, methyl-2-[[4-butyl-2-methyl-6-oxo-5-[[2'-(1H-tetrazol-5-yl)-[1,1'-binhenyl]-4-yl]methyl]-1-(6H)-pyrimidinyl] methyl]-3-thiophencarboxylate, 5-[(3,5-dibutyl-1H-1,2,4-triazol-1-yl)methyl]-2-[2-(1H-tetrazol-5-ylphenyl)] pyridine, 6-butyl-2-(2-phenylethyl)-5-[[2'-(1H-tetrazol-5-yl)[1,1'-biphenyl]-4-methyl]pyrimidin-4-(3H)-one D,L lysine salt, 5-methyl-7-n-propyl-8-[[2'-(1H-tetrazol-5-yl) biphenyl-4-yl]methyl]-[1,2,4]-triazolo[5-c]pyrimidin-2 (3H)-one, 2,7-diethyl-5-[[2'-(5-tetrazolyl)biphenyl-4-yl]

methyl]-5H-pyrazolo[1,5-b][1,2,4]triazole potassium salt, 2-[2-butyl-4,5-dihydro-4-oxo-3-[2'-(1H-tetrazol-5-yl)-4-biphenylmethyl]-3H-imidazol[4,5-c]pyridine-5-ylmethyl]-benzoic acid, ethyl ester, potassium salt, 3-methoxy-2,6-dimethyl-4-[[2'-(1H-tetrazol-5-yl)-1,1'-biphenyl-4-yl]methoxy]pyridine, 2-ethoxy-1-[[2'-(5-oxo-2,5-dihydro-1,2,4-oxadiazol-3-yl)biphenyl-4-yl]methyl]-1H-benzimidazole-7-carboxylic acid, 1-[N-(2'-(1H-tetrazol-5-yl)biphenyl-4-ylmethyl)-N-valerolylaminomethyl)cyclopentane-1-carboxylic acid, 7-methyl-2n-propyl-3-[[2'1H-tetrazol-5-yl) biphenyl-4-yl]methyl]-3H-imidazo[4,5-6]pyridine, 2-[5-[(2-ethyl-5,7-dimethyl-3H-imidazo[4,5-b]pyridine-3-yl) methyl]-2-quinolinyl]sodium benzoate, 2-butyl-6-chloro-4-hydroxymethyl-5-methyl-3-[[2'-(1H-tetrazol-5-yl)biphenyl-4-yl]methyl]pyridine, 2-[[[2-butyl-1-[(4-carboxyphenyl) methyl]-1H-imidazol-5-yl]methyl]amino]benzoic acid tetrazol-5-yl)biphenyl-4-yl]methyl]pyrimidin-6-one, 4(S)-[4-(carboxymethyl)phenoxy]-N-[2(R)-[4-(2-sulfobenzamido)imidazol-1-yl]octanoyl]-L-proline, 1-(2,6-dimethylphenyl)-4-butyl-1,3-dihydro-3-[[6-[2-(1H-tetrazol-5-yl)phenyl]-3-pyridinyl]methyl]-2H-imidazol-2-one, 5,8-ethano-5,8-dimethyl-2-n-propyl-5,6,7,8-tetrahydro-1-[[2'-(1H-tetrazol-5-yl)biphenyl-4-yl]methyl]-1H,4H-1,3,4a,8a-tetrazacyclopentanaphthalene-9-one, 4-[1-[2'-(1,2,3,4-tetrazol-5-yl)biphen-4-yl)methylamino]-5,6,7,8-tetrahydro-2-trifylquinazoline, 2-(2-chlorobenzoyl)imino-5-ethyl-3-[2'-(1H-tetrazole-5-yl)biphenyl-4-yl)methyl-1,3,4-thiadiazoline, 2-[5-ethyl-3-[2-(1H-tetrazole-5-yl)biphenyl-4-yl]methyl-1,3,4-thiazoline-2-ylidene]aminocarbonyl-1-cyclopentencarboxylic acid dipotassium salt, and 2-butyl-4-[N-methyl-N-(3-methylcrotonoyl)amino]-1-[[2'-(1H-tetrazol-5-yl)biphenyl-4-yl]methyl]-1H-imidazole-5-carboxylic acid 1-ethoxycarbonyloxyethyl ester.

24. The method as recited in claim 23, wherein the angiotensin II receptor antagonist is selected from the group consisting of: candesartan cilexetil, eprosartan, irbesartan, losartan, tasosartan, telmisartan, valsartan, and 3-(2'-(tetrazol-5-yl)-1,1'-biphen-4-yl)methyl-5,7-dimethyl-2-ethyl-3H-imidazo[4,5-b]pyridine.

25. A method for reducing the risk of sudden cardiac death by administering to chronic symptomatic heart failure patient a therapeutically effective amount of an angiotensin II receptor antagonist of formula I

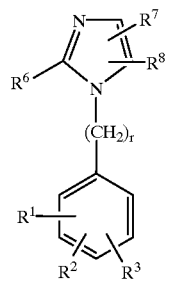

wherein:

$R^1$ is:

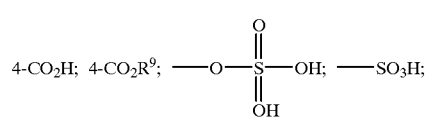

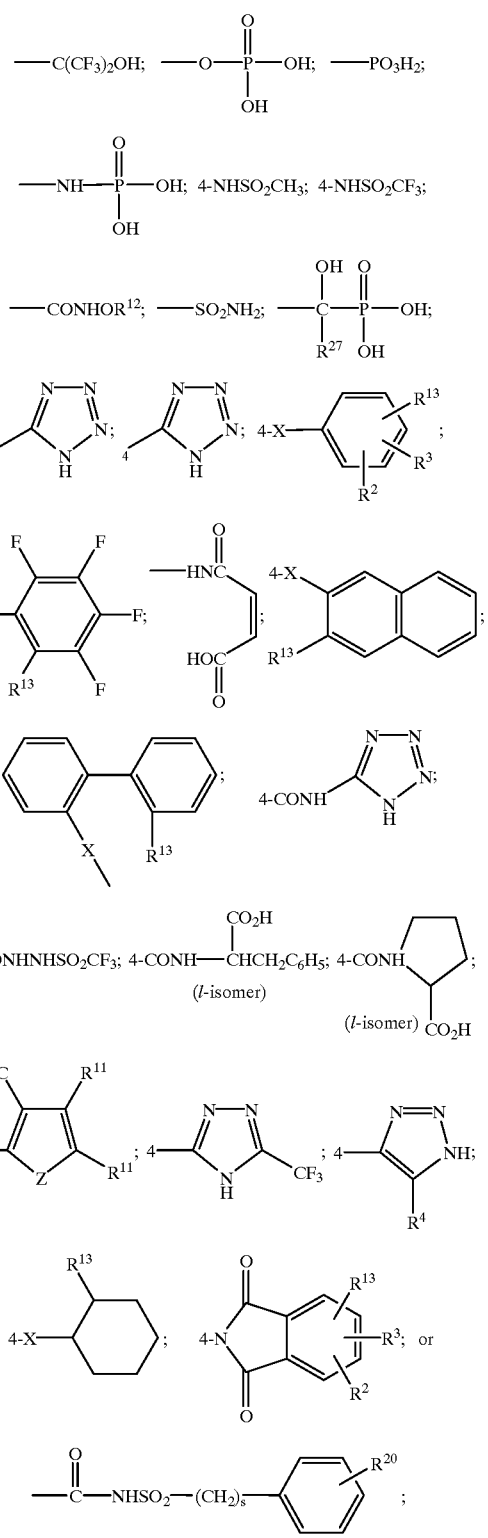

$R^2$ is H; Cl; Br; I; F; $NO_2$; CN; alkyl of 1 to 4 carbon atoms;

acyloxy of 1 to 4 carbon atoms; alkoxy of 1 to 4 carbon atoms; $CO_2H$; $CO_2R^9$; $HNSO_2CH_3$; $NHSO_2CF_3$; $CONHOR^{12}$; $SO_2NH_2$;

[structure: 5-methyl-1H-tetrazole]

aryl; or furyl;

R$^3$ is H; Cl, Br, I or F; alkyl of 1 to 4 carbon atoms or alkoxy of 1 to 4 carbon atoms;

R$^4$ is CN, NO$_2$ or CO$_2$R$^{11}$;

R$^5$ is H, alkyl of 1 to 6 carbon atoms, cycloalkyl of 3 to 6 carbon atoms alkenyl or alkynyl of 2 to 4 carbon atoms;

R$^6$ is alkyl of 2 to 10 carbon atoms, alkenyl or alkynyl of 3 to 10 carbon atoms or the same groups substituted with F or CO$_2$R$^{14}$; cycloalkyl of 3 to 9 carbon atoms, cycloalkylalkyl, of 4 to 10 carbon atoms; cycloalkylalkenyl or cycloalkylalkynyl 5 to 10 carbon atoms; (CH$_2$)$_s$Z(CH$_2$)$_m$R$^5$ optionally substituted with F or CO$_2$R$^{14}$; benzyl substituted on the phenyl ring with 1 or 2 halogens, alkoxy of 1 to 4 carbon atoms, alkyl of 1 to 4 carbon atoms or nitro;

R$^7$ is H, F, Cl, Br, I, NO$_2$, C$_v$F$_{2v+1}$, where v=1–6, C$_6$F$_5$; CN;

—C(=O)—R$^{16}$;

straight or branched alkyl of 1 to 6 carbon atoms; phenyl or phenylalkyl, where alkyl is 1 to 3 carbon atoms; or substituted phenyl or substituted phenylalkyl, where alkyl is 1 to 3 carbon atoms, substituted with one or two substituents selected from alkyl of 1 to 4 carbon atoms, F, Cl, Br, OH, OCH$_3$, CF$_3$, or COOR, where R is H, alkyl of 1 to 4 carbon atoms, or phenyl;

R$^8$ is H, CN, alkyl of 1 to 10 carbon atoms, alkenyl of 3 to 10 carbon atoms, or the same groups substituted with F; phenylalkenyl wherein the aliphatic portion is 2 to 6 carbon atoms; —(CH$_2$)imidazol-1-yl; —(CH$_2$)$_m$-1,2,3-triazolyl optionally substituted with one or two group selected from CO$_2$CH$_3$ or alkyl of 1 to 4 carbon atoms; —(CH$_2$)$_s$tetrazolyl;

—(CH$_2$)$_{n-1}$CH(OR$^{17}$)—R$^{11}$;  —(CH$_2$)$_n$OC(=O)R$^{14}$;  —(CH$_2$)$_n$SR$^{15}$;

—CH=CH(CH$_2$)$_s$CH(R$^{14}$)OR$^{15}$;  —CH=CH(CH$_2$)$_s$C(=O)R$^{16}$;

—C(=O)R$^{16}$;  —CH=CH(CH$_2$)$_s$OC(=O)R$^{11}$;  (CH$_2$)$_s$—CH(CH$_3$)—COR$^{16}$;

—(CH$_2$)$_n$C(=O)R$^{16}$;  —(CH$_2$)$_n$OC(=Y)NHR$^{10}$;  —(CH$_2$)$_n$NR$^{11}$C(=Y)OR$^{10}$;

—(CH$_2$)$_n$NR$^{11}$C(=O)NHR$^{10}$;  —(CH$_2$)$_n$NR$^{11}$SO$_2$R$^{10}$;

—(CH$_2$)$_n$NR$^{11}$C(=Y)R$^{10}$;  —(CH$_2$)$_m$F;  —(CH$_2$)$_m$ONO$_2$;

—CH$_2$N$_3$;  —(CH$_2$)$_m$NO$_2$;  —CH=N—NR$^{11}$R$^{17}$;

—(CH$_2$)$_m$-phthalimidyl;  —(CH$_2$)$_s$-(1,2,3-triazol-4-yl)-R$^4$;

—(CH$_2$)$_s$-(5-CF$_3$-1,2,4-triazol-3-yl);

—(CH$_2$)$_n$-[4-(2-methoxyphenyl)piperazin-1-yl];

—(CH$_2$)$_{n-1}$C(=O)-[4-(2-methoxyphenyl)piperazin-1-yl];

—CH=N—NH—SO$_2$-phenyl;  or

—CH=N—NH-(4,5-dihydroimidazol-2-yl);

R$^9$ is:

—CH(R$^{24}$)—OC(=O)R$^{21}$;

R$^{10}$ is alkyl of 1 to 6 carbon atoms or perfluoroalkyl of 1 to 6 carbon atoms, 1-adamantyl, 1-naphthyl, 1-(1-naphthyl)ethyl, or (CH$_2$)$_p$C$_6$H$_5$;

R$^{11}$ is H, alkyl of 1 to 6 carbon atoms, cycloalkyl of 3 to 6 carbon atoms, phenyl or benzyl;

R$^{12}$ is H, methyl or benzyl;

R$^{13}$ is

—CO$_2$H;  —CO$_2$R$^9$;  —CH$_2$CO$_2$H,  —CH$_2$CO$_2$R$^9$;

—O—S(=O)(OH)—OH;  —O—P(=O)(OH)—OH;  —SO$_3$H;

—NHP(=O)(OH)—OH;  —C(OH)(R$^{27}$)—P(=O)(OH)—OH;  —PO$_3$H$_2$;

—C(CF$_3$)$_2$OH;  —NHSO$_2$CH$_3$;  —NHSO$_2$CF$_3$;

—NHCOCF$_3$;  —CONHOR$^{12}$;  —SO$_2$NH$_2$;

-continued

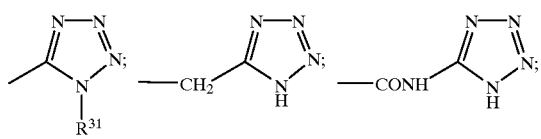

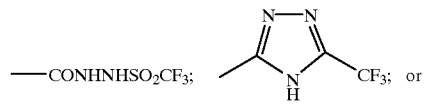

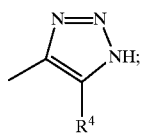

$R^{14}$ is H, alkyl or perfluoroalkyl of 1 to 8 carbon atoms, cycloalkyl of 3 to 6 carbon atoms, phenyl or benzyl;

$R^{15}$ is H, alkyl of 1 to 6 carbon atoms, cycloalkyl of 3 to 6 carbon atoms, phenyl, benzyl, acyl of 1 to 4 carbon atoms, or phenacyl;

$R^{16}$ is H, alkyl of 1 to 6 carbon atoms, cycloalkyl of 3 to 6 carbon atoms, $(CH_2)_pC_6H_5$, $OR^{17}$, or $NR^{18}R^{19}$;

$R^{17}$ is H, alkyl of 1 to 6 carbon atoms, cycloalkyl of 3 to 6 carbon atoms, phenyl or benzyl;

$R^{18}$ and $R^{19}$ independently are H, alkyl of 1 to 4 carbon atoms, phenyl, benzyl, α-methylbenzyl, or taken together with the nitrogen form a ring of the formula

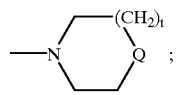

Q is $NR^{20}$, O or $CH_2$;

$R^{20}$ is H, alkyl of 1–4 carbon atoms, or phenyl;

$R^{21}$ is alkyl of 1 to 6 carbon atoms, $-NR^{22}R^{23}$, or

$R^{22}$ and $R^{23}$ independently are H, alkyl of 1 to 6 carbon atoms, benzyl, or are taken together as $(CH_2)_u$, where u is 3–6;

$R^{24}$ is H, $CH_3$ or $-C_6H_5$;

$R^{25}$ is $NR^{27}R^{28}$, $OR^{28}$, $NHCONH_2$, $NHCSNH_2$,

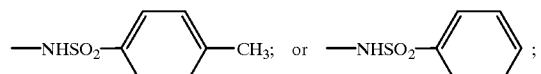

$R^{26}$ is hydrogen, alkyl with from 1 to 6 carbon atoms, benzyl, or allyl;

$R^{27}$ and $R^{28}$ are independently hydrogen, alkyl with from 1 to 5 carbon atoms, or phenyl;

$R^{29}$ and $R^{30}$ are independently alkyl of 1–4 carbon atoms or taken together are $-(CH_2)_q-$;

$R^{31}$ is H, alkyl or 1 to 4 carbon atoms, $-CH_2CH=CH_2$ or $-CH_2C_6H_4R^{32}$;

X is a carbon—carbon single bond,

Y is O or S;

Z is O, $NR^{11}$, or S;

m is 1 to 5;

n is 1 to 10;

p is 0 to 3;

q is 2 to 3;

r is 0 to 2;

s is 0 to 5;

t is 0 or 1;

or pharmaceutically acceptable salts of these compounds; provided that:

(1) the $R^1$ group is not in the ortho position;

(2) when $R^1$ is

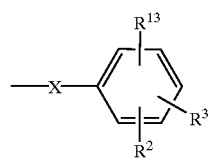

X is a single bond, and $R^{13}$ is $CO_2H$, or

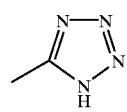

then $R^{13}$ must be in the ortho or meta position; or when $R^1$ and X are as above and $R^{13}$ is $NHSO_2CF_3$ or $NHSO_2CH_3$, $R^{13}$ must be ortho;

(3) when $R^1$ is

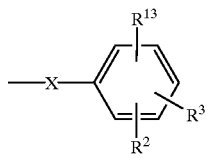

and X is other than a single bond, then $R^{13}$ must be ortho except when $X=NR^{23}CO$ and $R^{13}$ is $NHSO_2CF_3$ or $NHSO_2CH_3$, then $R^{13}$ must be ortho or meta;

(4) when $R^1$ is 4-$CO_2H$ or a salt thereof, $R^6$ cannot be S-alkyl;

(5) when $R^1$ is 4-$CO_2H$ or a salt thereof, the substituent on the 4-position of the imidazole cannot be $CH_2OH$, $CH_2OCOCH_3$, or $CH_2CO_2H$;

(6) when $R^1$ is

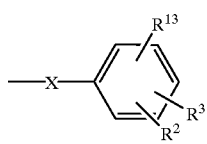

X is —$OCH_2$—, and $R^{13}$ is 2-$CO_2H$, and $R^7$ is H then $R^6$ is not $C_2H_5S$;

(7) when $R^1$ is

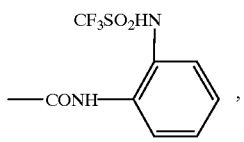

and $R^6$ is n-hexyl then $R^7$ and $R^8$ are not both hydrogen;

(8) when $R^1$ is

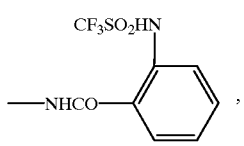

$R^6$ is not methoxybenzyl;

(9) the $R^6$ group is not

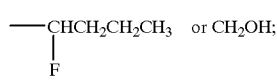

(10) when r=0, $R^1$ is

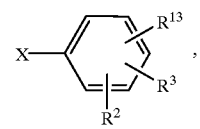

X is

$R^{13}$ is 2-$NHSO_2CF_3$, and $R^6$ is n-propyl, then $R^7$ and $R^8$ are not —$CO_2CH_3$;

(11) when r=0, $R^1$ is

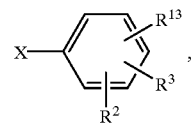

X is

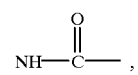

$R^{13}$ is 2-COOH, and $R^6$ is n-propyl, then $R^7$ and $R^8$ are not —$CO_2CH_3$;

(12) when r=1,

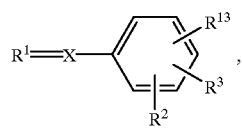

X is a single bond, $R^7$ is Cl, and $R^8$ is —CHO, then $R^{13}$ is not 3-(tetrazol-5-yl);

(13) when r=1,

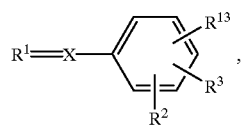

X is a single bond, $R^7$ is Cl, and $R^8$ is —CHO, then $R^{13}$ is not 4-(tetrazol-5-yl).

26. The method its recited in claim 25, wherein the angiotensin II receptor antagonist is losartan or EXP-3174, or a pharmaceutically acceptable thereof.

27. The method is recited in claim 26, wherein the symptomatic heart failure patient is 65 years of age or older.

28. A method for reducing hospitalization rates by administering to chronic symptomatic heart failure patients a therapeutically effective amount of an angiotensin II receptor antagonist.

29. A method for reducing hospitalization rates by administering to chronic symptomatic heart failure patients a therapeutically effective amount of an angiotensin II receptor antagonist selected from the group consisting of: candesartan cilexetil, eprosartan, irbesartan, losartan, tasosartan, telmisartan, valsartan, 3-(2'-(tetrazol-5-yl)-1,1'-biphen-4-yl) methyl-5,7-dimethyl-2-ethyl-3H-imidazo[4,5-b]pyridine, 4'2-ethyl-4-methyl-6-(5,6,7,8-tetrahydroimidazo[1,2-a] pyridin-2-yl]-benzimidazol-1-yl]-methyl]-1,1'-biphenyl]-2-carboxylic acid, 2-butyl-6-(1-methoxy-1-methylethyl)-2-[2'-(1H-tetrazol-5-yl)biphenyl-4-ylmethyl]guinazolin-4(3H)-one, 3-[(2'-carboxybiphenyl-4-yl)methyl]-2- cyclopropyl-7-methyl-3H-imidazo[4,5-b]pyridine, 2-butyl-4-chloro-1-[(2'-tetrazol-5-yl)biphenyl-4-yl)methyl]imidazole-carboxylic acid, 2-butyl-4-chloro-1-[[2'-(1H-tetrazol-5-yl)[1,1'-biphenyl]-4-yl]methyl]-1H-imidazole-5-carboxylic acid-1-(ethoxycarbonyl-oxy)ethyl ester potassium salt, dipotassium 2-butyl-4-(methylthio)-1-[[2-[[[(propylamino)carbonyl]amino]sulfonyl](1,1'-biphenyl)-4-yl]methyl]-1H-imidazole-5-carboxylate, methyl-2-[[4-butyl-2-methyl-6-oxo-5-[[2'-(1H-tetrazol-5-yl)-[1,1'-biphenyl]-4-yl]methyl]-1-(6H)-pyrimidinyl]methyl[-3-thiophencarboxylate, 5-[(3,5-dibutyl-1H-1,2,4-triazol-1-yl)methyl]-2-[2-(1H-tetrazol-5-ylphenyl)]pyridine, 6buty-2-(2-phenylethyl)-5-[[2'-(1H-tetrazol-5-yl)[1,1'-biphenyl]-4-methyl]pyrimidin-4-(3H)-one D,L lysine salt, 5-methyl-7-n-propyl-8-[[2'-(1H-tetrazol-5-yl)biphenyl-4-yl]methyl]-[1,2,4]-triazolo[1,5-c]pyrimidin-2(3H)-one, 2,7-diethyl-5-[[2'-(5-tetrazolyl)biphenyl-4-yl]methyl]-5H-pyrazolo[1,5-b][1,2,4]triazole potassium salt, 2-[2-butyl-4,5-dihydro-4-oxo-3-[2'-(1H-tetrazol-5-yl)-4-biphenylmethyl]-3H-imidazol[4,5-c]pyridine-5-ylmethyl]-benzoic acid, ethyl ester, potassium salt, 3-methoxy-2,6-dimethyl-4-[[2'-(1H-tetrazol-5-yl)-1,1'-biphenyl-4-yl]methoxy]pyridine, 2-ethoxy-1-[[2'-(5-oxo-2,5-dihydro-1,2,4-oxadiazol-3-yl)biphenyl-4-yl]methyl]-1H-benzimidazole-7-carboxylic acid, 1-[N-(2'-(1H-tetrazol-5-yl)biphenyl-4-yl-methyl)-N-valerolylaminomethyl)cyclopentane-1-carboxylic acid, 7-methyl-2n-propyl-3-[[2'1H-tetrazol-5-yl)biphenyl-4-yl]methyl]-3H-imidazo[4,5-6]pyridine, 2-[5-[(2-ethyl-5,7-dimethyl-3H-imidazo[4,5-b]pyridine-3-yl)methyl]-2-quinolinyl]sodium benzoate, 2-butyl-6-chloro-4-hydroxymethyl-5-methyl-3-[[2'-(1H-tetrazol-5-yl)biphenyl-4-yl]methyl]pyridine, 2-[[[2-butyl-1-[(4-carboxyphenyl)methyl]-1H-imidazol-5-yl]methyl]amino]benzoic acid tetrazol-5-yl)biphenyl-4-yl]methyl]pyrimidin-6-one, 4(S)-[4-(carboxymethyl)phenoxy]-N-[2(R)-[4-(2-sulfobenzamido)imidazol-1-yl]octanoyl]-L-proline, 1-(2,6-dimethylphenyl)-4-butyl-1,3-dihydro-3-[[6-[2-(1H-tetrazol-5-yl)phenyl]-3-pyridinyl]methyl]-2H-imidazol-2-one, 5,8-ethano-5,8-dimethyl-2-n-propyl-5,6,7,8-tetrahydro-1-[[2'-(1H-tetrazol-5-yl)biphenyl-4-yl]methyl]-1H,4H-1,3,4a,8a-tetrazacyclopentanaphthalene-9-one, 4-[1-[2'-(1,2,3,4-tetrazol-5-yl)biphen-4-yl)methylamino]-5,6,7,8-tetrahydro-2-trifylquinazoline, 2-(2-chlorobenzoyl)imino-5-ethyl-3-[2'-(1H-tetrazole-5-yl)biphenyl-4-yl)methyl-1,3,4-thiadiazoline, 2-[5-ethyl-3-[2-(1H-tetrazole-5-yl)biphenyl-4-yl]methyl-1,3,4-thiazoline-2-ylidene]aminocarbonyl-1-cyclopentencarboxylic acid dipotassium salt, and 2-butyl-4-[N-methyl-N-(3-methylcrotonoyl)amino]-1-[[2'-(1H-tetrazol-5-yl)biphenyl-4-yl]methyl]-1H-imidazole-5-carboxylic acid 1-ethoxycarbonyloxyethyl ester.

30. The method as recited in claim 29, wherein the angiotensin II receptor antagonist is selected from the group consisting of: candesartan cilexetil, eprosartan, irbesartan, losartan, tasosartan, telmisartan, valsartan, and 3-(2'-(tetrazol-5-yl)-1,1'-biphen-4-yl)methyl-5,7-dimethyl-2-ethyl-3H-imidazo[4,5-b]pyridine.

31. A method for reducing hospitalization rates by administering to chronic symptomatic heart failure patients a therapeutically effective amount of an angiotensin II receptor antagonist of formula I

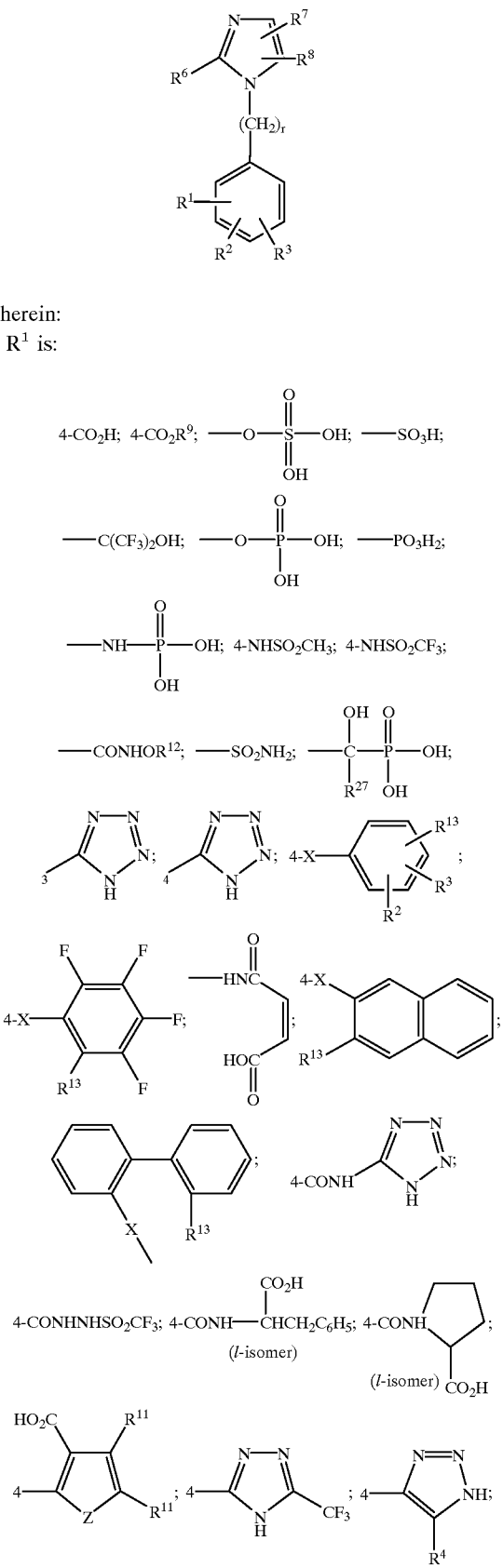

wherein:
$R^1$ is:

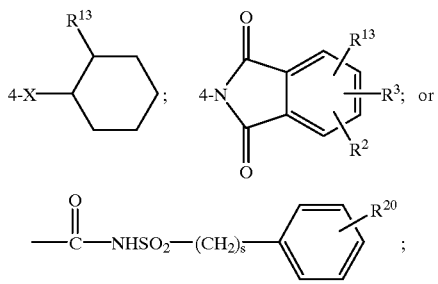

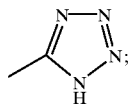

$R^2$ is H; Cl; Br; I; F; $NO_2$; CN; alkyl of 1 to 4 carbon atoms; acyloxy of 1 to 4 carbon atoms; alkoxy of 1 to 4 carbon atoms; $CO_2H$; $CO_2R^9$; $HNSO_2CH_3$; $NHSO_2CF_3$; $CONHOR^{12}$; $SO_2NH_2$;

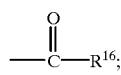

aryl; or furyl;

$R^3$ is H; Cl, Br, I or F; alkyl of 1 to 4 carbon atoms or alkoxy of 1 to 4 carbon atoms;

$R^4$ is CN, $NO_2$ or $CO_2R^{11}$;

$R^5$ is H, alkyl of 1 to 6 carbon atoms, cycloalkyl of 3 to 6 carbon atoms alkenyl or alkynyl of 2 to 4 carbon atoms;

$R^6$ is alkyl of 2 to 10 carbon atoms, alkenyl or alkynyl of 3 to 10 carbon atoms or the same groups substituted with F or $CO_2R^{14}$; cycloalkyl of 3 to 8 carbon atoms, cycloalkylalkyl, of 4 to 10 carbon atoms; cycloalkylalkenyl or cycloalkylalkynyl 5 to 10 carbon atoms; $(CH_2)_sZ(CH_2)_mR^5$ optionally substituted with F or $CO_2R^{14}$; benzyl substituted on the phenyl ring with 1 or 2 halogens, alkoxy of 1 to 4 carbon atoms, alkyl of 1 to 4 carbon atoms or nitro;

$R^7$ is H, F, Cl, Br, I, $NO_2$, $C_vF_{2v+1}$, where v=1–6, $C_6F_5$; CN;

—C(O)—$R^{16}$;

straight or branched alkyl of 1 to 6 carbon atoms; phenyl or phenylalkyl, where alkyl is 1 to 3 carbon atoms; or substituted phenyl or substituted phenylalkyl, where alkyl is 1 to 3 carbon atoms, substituted with one or two substituents selected from alkyl of 1 to 4 carbon atoms, F, Cl, Br, OH, $OCH_3$, $CF_3$, or COOR, where R is H, alkyl of 1 to 4 carbon atoms, or phenyl;

$R^8$ is H, CN, alkyl of 1 to 10 carbon atoms, alkenyl of 3 to 10 carbon atoms, or the same groups substituted with F; phenylalkenyl wherein the aliphatic portion is 2 to 6 carbon atoms; —$(CH_2)_m$-imidazol-1-yl; —$(CH_2)_m$-1,2,3-triazolyl optionally substituted with one or two group selected from $CO_2CH_3$ or alkyl of 1 to 4 carbon atoms; —$(CH_2)_s$ tetrazolyl;

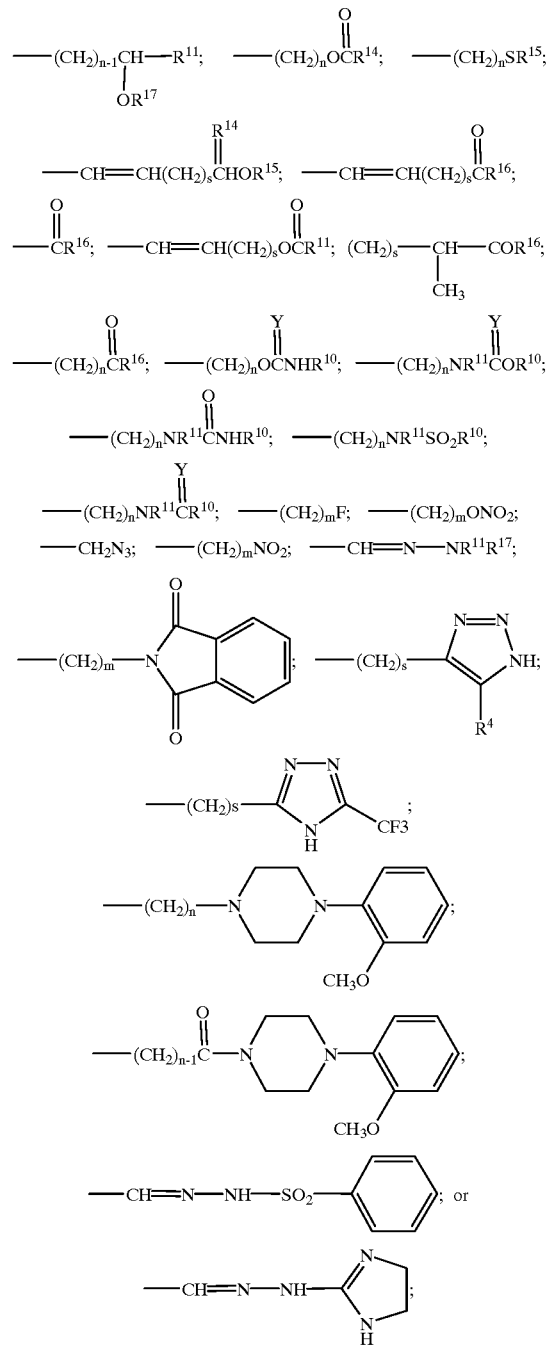

$R^9$ is:

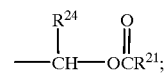

$R^{10}$ is alkyl of 1 to 6 carbon atoms or perfluoroalkyl of 1 to 6 carbon atoms, 1-adamantyl, 1-naphthyl, 1-(1-naphthyl)ethyl, or $(CH_2)_pC_6H_5$;

$R^{11}$ is H, alkyl of 1 to 6 carbon atoms, cycloalkyl of 3 to 6 carbon atoms, phenyl or benzyl;

$R^{12}$ is H, methyl or benzyl;

$R^{13}$ is

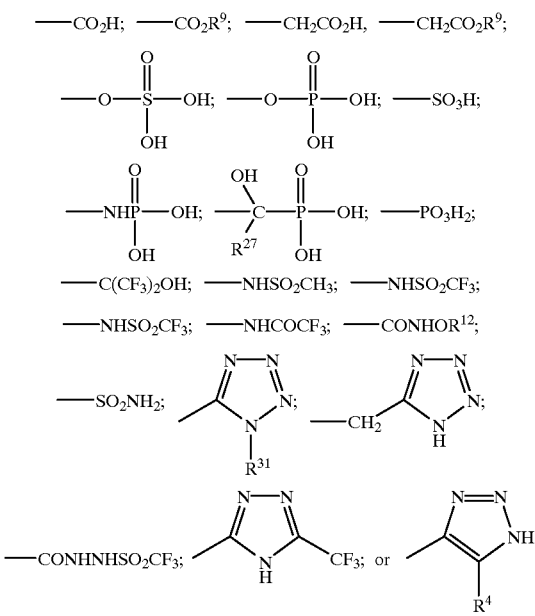

$R^{14}$ is H, alkyl or perfluoroalkyl of 1 to 8 carbon atoms, cycloalkyl of 3 to 6 carbon atoms, phenyl or benzyl;

$R^{15}$ is H, alkyl of 1 to 6 carbon atoms, cycloalkyl of 3 to 6 carbon atoms, phenyl, benzyl, acyl of 1 to 4 carbon atoms, or phenacyl;

$R^{16}$ is H, alkyl of 1 to 6 carbon atoms, cycloalkyl of 3 to 6 carbon atoms, $(CH_2)_p C_6 H_5$, $OR^{17}$, or $NR^{18}R^{19}$;

$R^{17}$ is H, alkyl of 1 to 6 carbon atoms, cycloalkyl of 3 to 6 carbon atoms, phenyl or benzyl;

$R^{18}$ and $R^{19}$ independently are H, alkyl of 1 to 4 carbon atoms, phenyl, benzyl, α-methylbenzyl, or taken together with the nitrogen form a ring of the formula

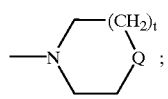

Q is $NR^{20}$, O or $CH_2$;

$R^{20}$ is H, alkyl of 1–4 carbon atoms, or phenyl;

$R^{21}$ is alkyl of 1 to 6 carbon atoms, $—NR^{22}R^{23}$, or

$R^{22}$ and $R^{23}$ independently are H, alkyl of 1 to 6 carbon atoms, benzyl, or are taken together as $(CH_2)_u$, where u is 3–6;

$R^{24}$ is H, $CH_3$ or $—C_6H_5$;

$R^{25}$ is $NR^{27}R^{28}$, $OR^{28}$, $NHCONH_2$, $NHCSNH_2$,

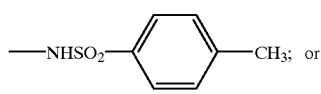

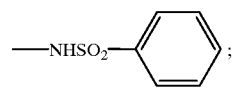

$R^{26}$ is hydrogen, alkyl with from 1 to 6 carbon atoms, benzyl, or allyl;

$R^{27}$ and $R^{28}$ are independently hydrogen, alkyl with from 1 to 5 carbon atoms, or phenyl;

$R^{29}$ and $R^{30}$ are independently alkyl of 1–4 carbon atoms or taken together are $—(CH_2)—$;

$R^{31}$ is H, alkyl or 1 to 4 carbon atoms, $—CH_2CH=CH_2$ or $—CH_2C_6H_4R^{32}$;

X is a carbon—carbon single bond,

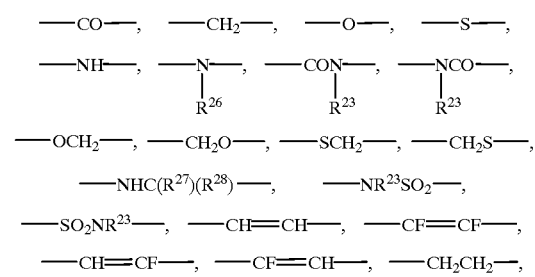

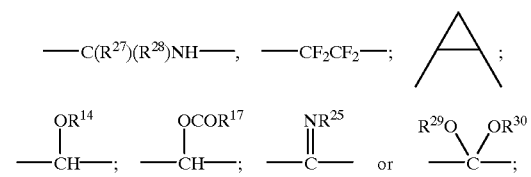

Y is O or S;
Z is O, $NR^{11}$, or S;
m is 1 to 5;
n is 1 to 10;
p is 0 to 3;
q is 2 to 3;
r is 0 to 2;
s is 0 to 5;
t is 0 or 1;
or pharmaceutically acceptable salts of these compounds; provided that:
(1) the $R^1$ group is not in the ortho position;
(2) when $R^1$ is

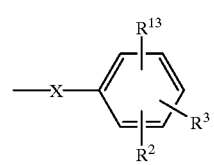

X is a single bond, and $R^{13}$ is $CO_2H$, or

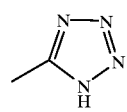

then $R^{13}$ must be in the ortho or meta position; or when $R^1$ and X are is above and $R^{13}$ is $NHSO_2CF_3$ or $NHSO_2CH_3$, $R^{13}$ must be ortho;

(3) when $R^1$ is

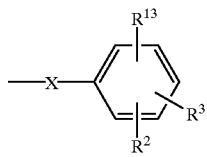

and X is other than a single bond, then $R^{13}$ must be ortho except when $X=NR^{23}CO$ and $R^{13}$ is $NHSO_2CF_3$ or $NHSO_2CH_3$, then $R^{13}$ must be ortho or meta;

(4) when $R^1$ is 4-$CO_2H$ or a salt thereof, $R^6$ cannot be S-alkyl;

(5) when $R^1$ is 4-$CO_2H$ or a salt thereof, the substituent on the 4-position of the imidazole cannot be $CH_2OH$, $CH_2OCOCH_3$, or $CH_2CO_2H$;

(6) when $R^1$ is

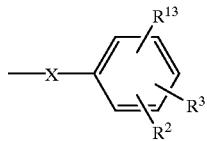

X is —$OCH_2$—, and $R^{13}$ is 2-$CO_2H$, and $R^7$ is H then $R^6$ is not $C_2H_5S$;

(7) when $R^1$ is

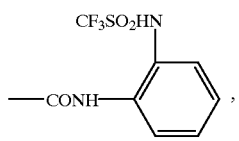

and $R^6$ is n-hexyl then $R^7$ and $R^8$ are not both hydrogen;

(8) when $R^1$ is

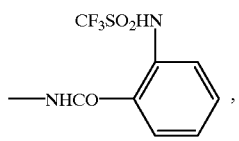

$R^6$ is not methoxybenzyl;

(9) the $R^6$ group is not

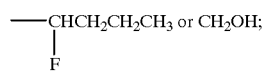

(10) when r=0, $R^1$ is

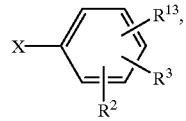

X is

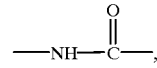

$R^{13}$ is 2-$NHSO_2CF_3$, and $R^6$ is n-propyl, then $R^7$ and $R^8$ are not —$CO_2CH_3$;

(11) when r=0, $R^1$ is

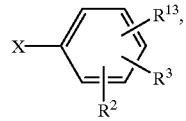

X is

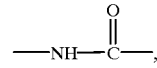

$R^{13}$ is 2-COOH, and $R^6$ is n-propyl, then $R^7$ and $R^8$ are not —$CO_2CH_3$;

(12) when r=1,

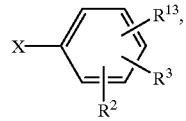

X is a single bond, $R^7$ is Cl, and $R^8$ is —CHO, then $R^{13}$ is not 3-(tetrazol-5-yl);

(13) when r=1,

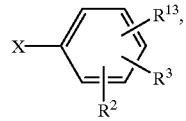

X is a single bond, $R^7$ is Cl, and $R^8$ is —CHO, then $R^{13}$ is not 4-(tetrazol-5-yl).

32. The method is recited in claim 31, wherein the angiotensin II receptor antagonist is losartan or EXP-3174, or its pharmaceutically acceptable salt thereof.

33. The method as recited in claim 32, wherein the symptomatic heart failure patient is 65 years of age or older.

* * * * *

UNITED STATES PATENT AND TRADEMARK OFFICE
CERTIFICATE OF CORRECTION

PATENT NO. : 6,201,002 B1
DATED : March 13, 2001
INVENTOR(S) : Polly A. Beere, Paul I. Chang, Bertram Pitt, Eva J. Rucinska, Robert Segal, Divakar Sharma and Duane B. Snavely It is certified that error appears in the above-identified patent and that said Letters Patent is hereby corrected as shown below:

Column 49,
Lines 17 through 19, should read:
-- pyrimidin-6-one, 1-(2,6-dimethylphenyl)-4-butyl-1,3-dihydro-3-[[6- --.
Line 42, should read:
-- to chronic symptomatic heart failure patients a therapeuti- --.

Column 50,
Lines 51 through 57, the structures should read:
--

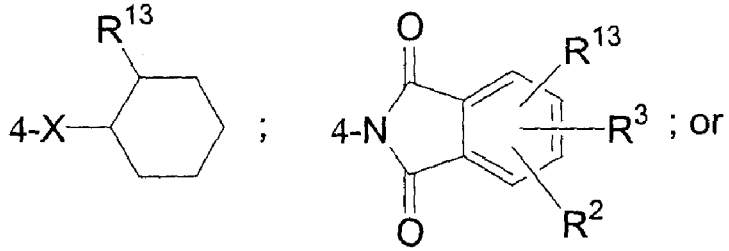

--.

Column 51,
Lines 57 through 60, should read:
--

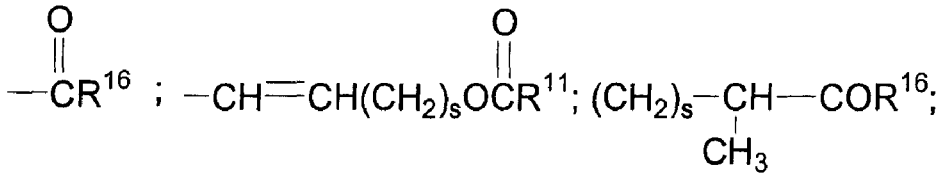

--.

Column 53,
Line 29, should read:
-- atoms, phenyl, benzyl, α-methylbenzyl, or taken --.

UNITED STATES PATENT AND TRADEMARK OFFICE
CERTIFICATE OF CORRECTION

PATENT NO. : 6,201,002 B1
DATED : March 13, 2001
INVENTOR(S) : Polly A. Beere, Paul I. Chang, Bertram Pitt, Eva J. Rucinska, Robert Segal, Divakar Sharma and Duane B. Snavely It is certified that error appears in the above-identified patent and that said Letters Patent is Column 58,
Lines 52 through 67, should read:
-- 2-Butyl-4-chloro-l-[(2'-(1H-tetrazol-5-yl)biphenyl-4-yl)
methyl]-5-(hydroxymethyl)imidazole,
2-Butyl-4-chloro-1-[(2' -carboxybiphenyl-4-yl)methyl]-5-
(hydroxymethyl)imidazole,
2-Butyl-4-chloro-1-[(2'-carboxybiphenyl-4-yl)methyl]-5-
[(methoxycarbonyl)aminomethyl]imidazole,
2-Butyl-4-chloro-1-[2'carboxybiphenyl-4-yl)methyl]-5-
[(propoxycarbonyl)aminomethyl]imidazole,
2-Butyl-4-chloro-1-[(2'-carboxybiphenyl-4-yl)methyl]
imidazole-5-carboxaldehyde,
2-Butyl-1-[(2'carboxybiphenyl-4-yl)methyl]-imidazole-5-
carboxaldehyde,
2-(1E-Butenyl)-4-chloro-1-[(2'-carboxybiphenyl-4-yl)
methyl]-5-(hydroxymethyl)imidazole,
2-(1E-Butenyl)-4-chloro-1-[(2'-carboxybiphenyl-4-yl)
methyl]-imidazole-5-carboxaldehyde, --

Column 59,
Lines 1 through 31, should read:
-- 2-Propyl-4-chloro-l-[(2'-(1H-tetrazol-5-yl)biphenyl-4-yl)
methyl]-5-(hydroxymethyl)imidazole,
2-Propyl-4-chloro-1-[(2'-(1H-tetrazol-5-yl)biphenyl-4-yl)
methyl]-imidazole-5-carboxaldehyde,
2-Butyl-4-chloro- 1 -[(2'-(1H-tetrazol-5-yl)biphenyl-4-yl)
methyl]-imidazole-5-carboxaldehyde,
2-(1E-Butenyl)-4-chloro-1-[(2'-(1H-tetrazol-5-yl)biphenyl-
4-yl)methyl]-5-hydroxymethyl)imidazole,
2-(1E-Butenyl)-4-chloro-1-[(2'-(1H-tetrazol-5-yl)biphenyl-
4-yl)methyl]imidazole-5-carboxaldehyde,
2-Butyl-4-chloro-1-[(2'-(1H-tetrazol-5-yl)-biphenyl-4-yl)
methyl]-imidazole-5-carboxylic acid,
2-Propyl-4-chloro-1-[(2' (1H-tetrazol-5-yl)-biphenyl-4-yl)
methyl]-imidazole-5-carboxylic acid,
2-Propyl-4-trifluoromethyl-1-[(2' -(1H-tetrazol-5-yl)
biphenyl-4-yl)methyl]imidazole-5-carboxylic acid,
2-Propyl-4-trifluoromethyl-1-[(2' -(1H-tetrazol-5-yl)
biphenyl-4-yl)methyl]-5-(hydroxylmethyl)imidazole,

UNITED STATES PATENT AND TRADEMARK OFFICE
CERTIFICATE OF CORRECTION

PATENT NO.    : 6,201,002 B1
DATED         : March 13, 2001
INVENTOR(S)   : Polly A. Beere, Paul I. Chang, Bertram Pitt, Eva J. Rucinska, Robert Segal, Divakar Sharma and Duane B. Snavely It is certified that error appears in the above-identified patent and that said Letters Patent is Column 59 (continued),
2-Butyl-4-trifluoromethyl-l-[(2'-(1H-tetrazol-5-yl)
biphenyl-4-yl)methyl]imidazole-5-carboxylic acid,
2-Propyl-4-trifluoromethyl-l-[(2'-(carboxybiphenyl-4-yl)
methyl]-imidazole-5-carboxaldehyde,
2-Propyl-4-pentafluoroethyl-l-[(2'-(1H-tetrazol-5-yl)
biphenyl-4-yl)methyl]-5-(hydroxymethyl)imidazole,
2-Propyl-1-[(2'-(1H-tetrazol-5-yl)biphenyl-4-yl)methyl]
imidazole-4,5,-dicarboxylic acid,
2-Propyl-4-pentafluoroethyl-1-[(2'-(1H-tetrazol-5-yl)
biphenyl-4-yl)methyl]imidazole-5-carboxylic acid, and
2-Propyl-4-pentafluoroethyl-[(2' (1H-tetrazol-5-yl)
biphenyl-4-yl)methyl]imidazole-5-carboxaldehyde,
or a pharmaceutically acceptable sale thereof. --

Column 60,
Line 8, should read:
-- methyl]-5H-pyrazolo[1,5-b][1,2,4]triazole potassium salt, --.
Line 39, should read:
-- [N-methyl-N-(3-methylcrotonoyl)amino]-1-[[2'-(1H- --.

Column 61,
Lines 9 through 13, should read:
--

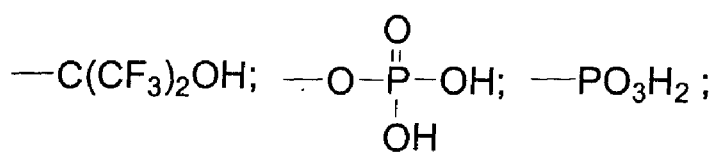

--.

Lines 52 through 57, should read:
--

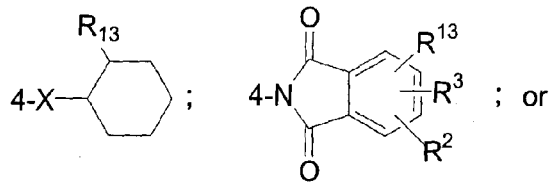

--.

UNITED STATES PATENT AND TRADEMARK OFFICE
CERTIFICATE OF CORRECTION

PATENT NO. : 6,201,002 B1
DATED : March 13, 2001
INVENTOR(S) : Polly A. Beere, Paul I. Chang, Bertram Pitt, Eva J. Rucinska, Robert Segal, Divakar Sharma and Duane B. Snavely It is certified that error appears in the above-identified patent and that said Letters Patent is Column 64,
Line 23, should read:
-- $R^{14}$ is H, alkyl or perfluoroalkyl of 1 to 8 carbon atoms, --.

Column 66,
Line 12, should read:
-- ortho except when X=$NR^{23}$CO and $R^{13}$ is $NHSO_2CF_3$ --.

Column 67,
Line 49 should read:
-- angiotensin II receptor antagonist is losartan or EXP-3174 --.
Line 64 should read:
-- imidazo[4,5-b]pyridine, 4'[2-ethyl-4-methyl-6-(5,6,7,8- --.

Column 68,
Line 8, should read:
-- [[2-[[[(propylamino)carbonyl]amino]sulfonyl](1,1'- --.
Lines 22 through 24, should read:
-- 3-methoxy-2,6- --.

Column 70,
Line 58, should read:
-- with F or $CO_2R^{14}$; cycloalkyl of 3 to 8 carbon atoms, --.

Column 76,
Line 66, should read:
-- biphenyl-4-yl]methyl]-[1,2,4]-triazolo[1,5-c]pyrimidin-2 --.

Column 79,
Line 18, should read:
-- with F or $CO_2R^{14}$; cycloalkyl of 3 to 8 carbon atoms, --.
Line 42, should read:
-- carbon atoms; -$(CH_2)_m$-imidazol-1-yl; $(CH_2)_m$ -1,2,3- --.

Column 85,
Line 11, should read:
-- biphenyl]-4-yl]methyl]-1-(6H)-pyrimidinyl]methyl]-3- --.
Line 13, should read:
-- methyl]-2-[2-(1H-tetrazol-5-ylphenyl)]pyridine, 6-butyl-2- --.

UNITED STATES PATENT AND TRADEMARK OFFICE
CERTIFICATE OF CORRECTION

PATENT NO. : 6,201,002 B1
DATED : March 13, 2001
INVENTOR(S) : Polly A. Beere, Paul I. Chang, Bertram Pitt, Eva J. Rucinska, Robert Segal, Divakar Sharma and Duane B. Snavely It is certified that error appears in the above-identified patent and that said Letters Patent is Column 86,
Lines 54 through 59, should read:
--

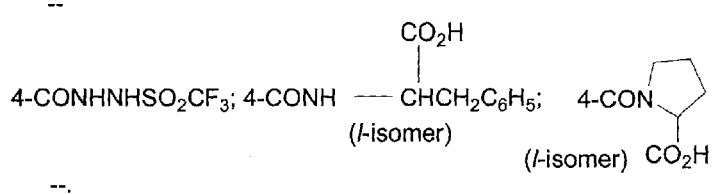

--.

Column 90,
Line 12, should read:
-- or taken together are $-(CH_2)q-$; --.
Line 66, should read:
-- $R^1$ and X are as above and $R^{13}$ is $NHSO_2CF_3$ or --.

Signed and Sealed this

Twenty-fifth Day of June, 2002

Attest:

*Attesting Officer*

JAMES E. ROGAN
*Director of the United States Patent and Trademark Office*